(12) United States Patent
Boveja et al.

(10) Patent No.: US 9,918,792 B1
(45) Date of Patent: Mar. 20, 2018

(54) METHODS AND SYSTEM FOR ATRIAL FIBRILLATION ABLATION USING A FLUOROSCOPY AND/OR MEDICAL IMAGES BASED CARDIAC MAPPING SYSTEM WITH OPTIONAL ESOPHAGEAL TEMPERATURE MONITORING

(71) Applicants: Birinder R. Boveja, Greenfield, WI (US); Angely Widhany, Greenfield, WI (US)

(72) Inventors: Birinder R. Boveja, Greenfield, WI (US); Angely Widhany, Greenfield, WI (US)

(73) Assignee: AMERICAN MEDICAL TECHNOLOGIES, LLC, Wauwatosa, WI (US)

( * ) Notice: Subject to any disclaimer, the term of this patent is extended or adjusted under 35 U.S.C. 154(b) by 0 days.

(21) Appl. No.: 15/433,767

(22) Filed: Feb. 15, 2017

Related U.S. Application Data

(63) Continuation-in-part of application No. 15/209,265, filed on Jul. 13, 2016, now Pat. No. 9,820,802.
(Continued)

(51) Int. Cl.
*A61B 18/04* (2006.01)
*A61B 18/14* (2006.01)
(Continued)

(52) U.S. Cl.
CPC .......... *A61B 18/1492* (2013.01); *A61B 6/481* (2013.01); *A61B 18/02* (2013.01); *A61B 18/16* (2013.01); *A61B 18/24* (2013.01); *G06T 5/007* (2013.01); *G06T 7/0012* (2013.01); *G06T 11/60* (2013.01); *A61B 2018/0022* (2013.01); *A61B 2018/00029* (2013.01); *A61B 2018/00351* (2013.01); *A61B 2018/00577* (2013.01); *A61B 2018/00648* (2013.01); *A61B 2018/00815* (2013.01); *A61B 2018/00821* (2013.01); *A61B 2018/00839* (2013.01);
(Continued)

(58) Field of Classification Search
CPC . A61B 5/7285; A61B 6/5247; A61B 18/1492; A61B 6/481; A61B 18/02; A61B 18/24; A61B 2018/0022; A61B 2018/00577; A61B 2018/00551; G06T 7/0012
See application file for complete search history.

(56) References Cited

U.S. PATENT DOCUMENTS

| | | |
|---|---|---|
| 5,348,554 A | 9/1994 | Imran et al. |
| 6,052,618 A | 4/2000 | Dahlke et al. |

(Continued)

*Primary Examiner* — Robert N Wieland

(57) ABSTRACT

A method and system for atrial fibrillation ablations utilizing a fluoroscopy and/or medical image(s) based cardiac mapping system adapted for balloon based catheters including cryoballoon catheter. The method and system incorporates overlaying two or more sets of images on top of each other where the transparency between the images can be adjusted as an aid in the optimal placement of the balloon based catheters. Further, tags and markers are also placed on fluoroscopic and/or other medical images indicative of where the tissue that has been ablated. The method and system also comprises the ability to monitor esophageal temperature, and to activate alarms and/or energy delivery interrupt based on pre-determined esophageal temperature parameters.

14 Claims, 37 Drawing Sheets

Related U.S. Application Data

(60) Provisional application No. 62/343,745, filed on May 31, 2016, provisional application No. 62/346,539, filed on Jun. 6, 2016, provisional application No. 62/429,691, filed on Dec. 2, 2016.

(51) Int. Cl.

| | | |
|---|---|---|
| *A61B 18/16* | (2006.01) | |
| *A61B 18/02* | (2006.01) | |
| *A61B 18/24* | (2006.01) | |
| *A61B 6/00* | (2006.01) | |
| *G06T 7/00* | (2017.01) | |
| *G06T 11/60* | (2006.01) | |
| *G06T 5/00* | (2006.01) | |
| *A61B 18/00* | (2006.01) | |

(52) U.S. Cl.
CPC ............ *A61B 2018/00898* (2013.01); *A61B 2018/00982* (2013.01); *A61B 2018/0212* (2013.01); *G06T 2207/10081* (2013.01); *G06T 2207/10088* (2013.01); *G06T 2207/10121* (2013.01); *G06T 2207/10132* (2013.01); *G06T 2207/30048* (2013.01)

(56) References Cited

U.S. PATENT DOCUMENTS

| | | |
|---|---|---|
| 7,819,817 B2 | 10/2010 | Rahn |
| 8,224,422 B2 | 7/2012 | Mottola |
| 8,271,095 B2 | 9/2012 | O'Sullivan |
| 8,273,016 B2 | 9/2012 | O'Sullivan |
| 8,303,505 B2 | 11/2012 | Webler et al. |
| 8,355,801 B2 | 1/2013 | O'Sullivan |
| 9,078,567 B2 * | 7/2015 | Fuimaono ............ A61B 5/055 |
| 9,147,289 B2 | 9/2015 | Bourier et al. |
| 9,439,735 B2 | 9/2016 | Guttman et al. |
| 9,468,485 B2 | 10/2016 | Wittenberger et al. |
| 2014/0012155 A1 | 1/2014 | Flaherty et al. |
| 2016/0143522 A1 * | 5/2016 | Ransbury ............ A61B 1/3137 600/317 |

* cited by examiner

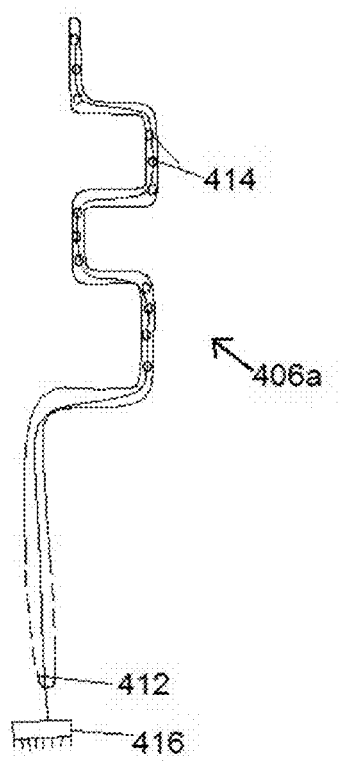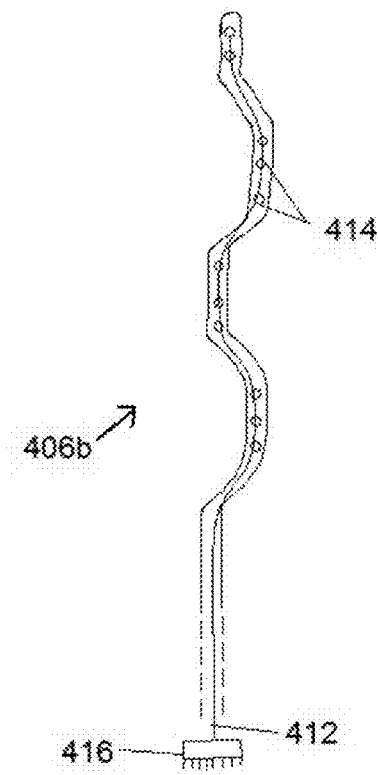
FIG. 17A    FIG. 17B
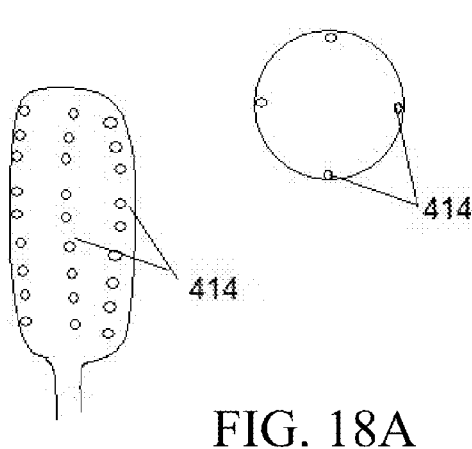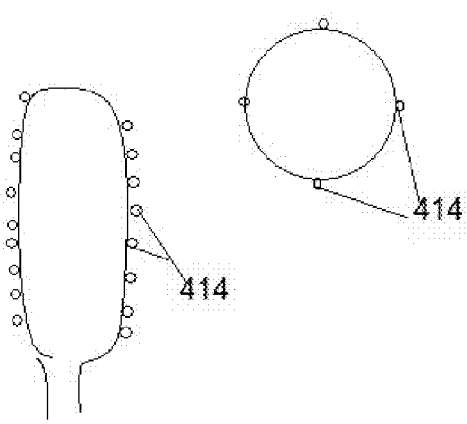
FIG. 18A    FIG. 18B Live and Recorded Images in high resolution Live and Recorded Images in high resolution

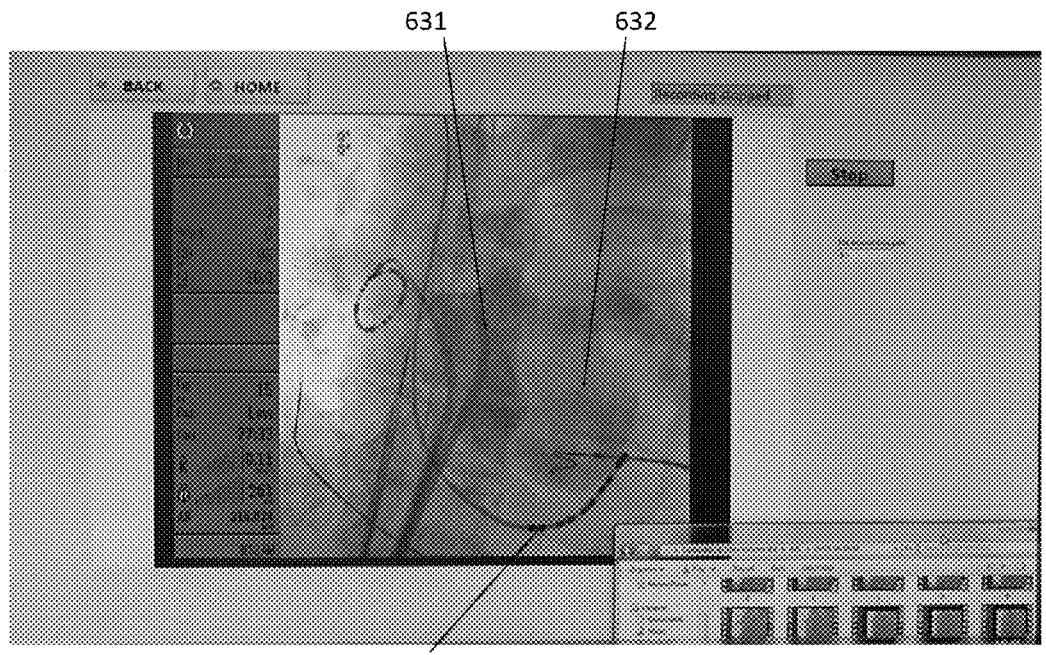
FIG. 45  629  2nd Recorded "dye" injection
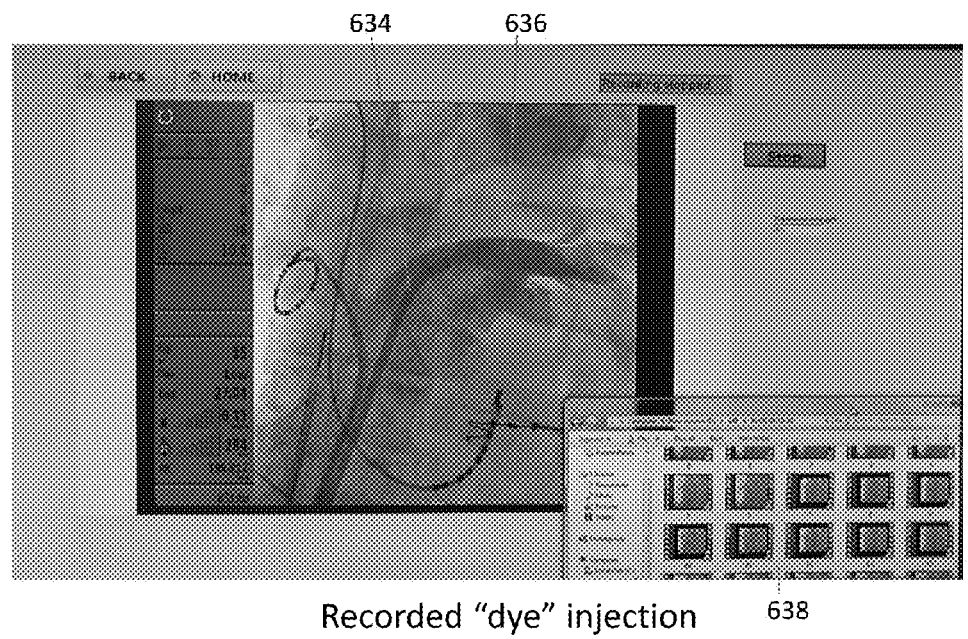
Recorded "dye" injection  638
FIG. 46

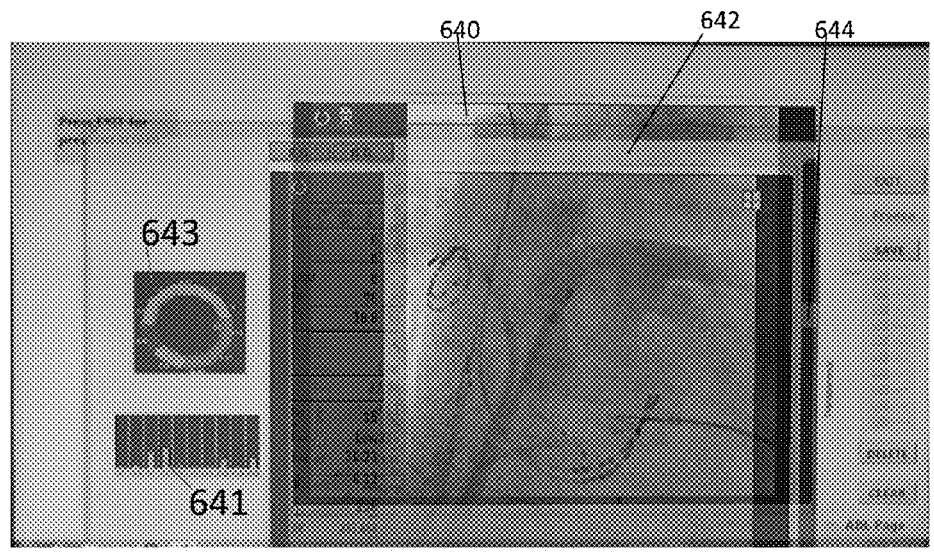
Live fluoroscopy overlaid on recorded dye injection image with signals from circular catheter
FIG 47
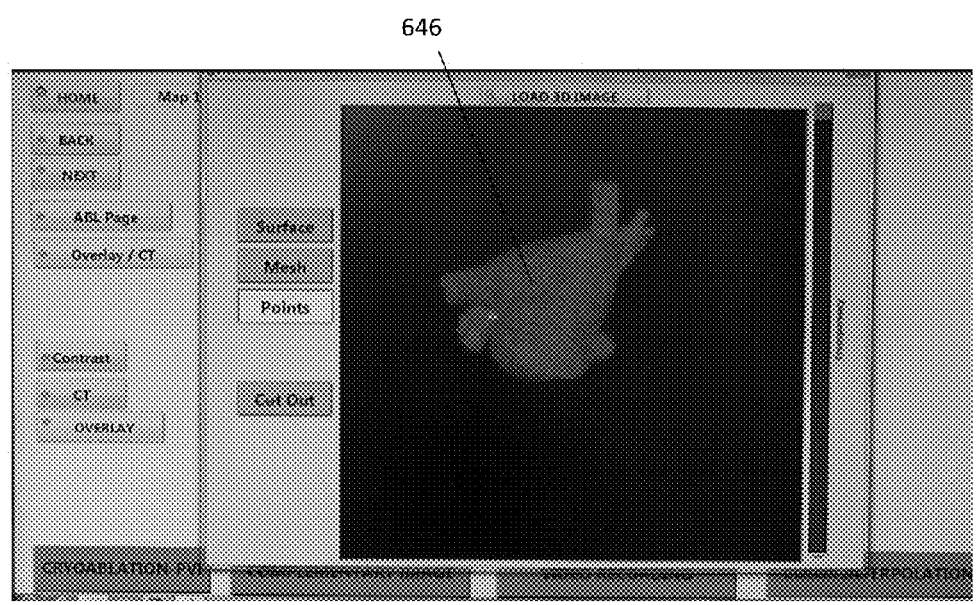
FIG 48    Patient's CT CT overlaid on contrast image CT overlaid on contrast image with live fluoro overlayed and signals from circ. Catheter (contrast + CT+ live fluoro + signals)

METHODS AND SYSTEM FOR ATRIAL FIBRILLATION ABLATION USING A FLUOROSCOPY AND/OR MEDICAL IMAGES BASED CARDIAC MAPPING SYSTEM WITH OPTIONAL ESOPHAGEAL TEMPERATURE MONITORING

This application is a Continuation-in-part (CIP) of U.S. application Ser. No. 15/209,265 filed Jul. 13, 2016. This application also claims priority of the following provisional patent applications.
FLUOROSCOPY AND CARDIAC IMAGE(S) BASED MAPPING SYSTEM FOR GUIDING CRYOBALLOON ABLATIONS FOR ATRIAL FIBRILLATION—Application No. 62/343,745 filed May 31, 2016
FLUOROSCOPY AND CARDIAC IMAGE(S) BASED MAPPING SYSTEM FOR GUIDING CRYOBALLOON ABLATIONS FOR ATRIAL FIBRILLATION WITH AUTOMATIC FLUOROSCOPIC RECORDING MECHANISM—Application No. 62/346,539 filed Jun. 6, 2016
MAPPING METHOD AND SYSTEM FOR CRYOBALLOON ABLATION FOR ATRIAL FIBRILLATION—Application No. 62/429,691 filed Dec. 2, 2016

FIELD OF DISCLOSURE

The present disclosure relates to atrial fibrillation ablations, more specifically to method and system of mapping for atrial fibrillation ablations utilizing a balloon based catheter, and esophageal temperature monitoring utilizing a fluoroscopy and/or medical images based cardiac mapping system.

BACKGROUND

General Background of Atrial Fibrillation

Atrial fibrillation (AF) is the most prevalent cardiac arrhythmia. It affects 1% to 2% of the general population with an important increase in incidence with age. In the United States it is estimated that over 5 million people have atrial fibrillation, and because of our aging population the prevalence of this arrhythmia will increase significantly over the next decade.

Atrial fibrillation is associated with increased morbidity and mortality, and in particular, a general decrease in quality of life for those afflicted with atrial fibrillation. AF can also cause tachycardia mediated cardiomyopathy or worsening of pre-existing heart failure. Moreover, AF is known to increase the mortality risk 1.5-2 fold with the risk for stroke increasing five-fold. Patients are at an increased risk of stroke unless they are treated adequately with anticoagulants. Anticoagulant treatment however, increases the patient's risk of bleeding, which carries with it is own set of dangers. Medications currently available for treating atrial fibrillation have proven to be only moderately effective in decreasing the incidence of recurrent atrial fibrillation, and these medications do not decrease the patient's risk of having a stroke.

One method of treating atrial fibrillation has been to perform ablation of selected areas of the left atrium. There is strong evidence to suggest that ablating these areas of the left atrium serves to cure or prevent further incidences of atrial fibrillation, which thereby has shown to reduce the risk of stroke and reduce the necessity of anticoagulant therapy. Typically, ablation of this type is carried out via an intravascular catheter using radiofrequency or microwave energy to cause thermal changes to the selected parts of the left atrial tissue.

Besides having a good safety profile, catheter ablation therapy for AF has proved effective in establishing and maintaining sinus rhythm. Ablation for atrial fibrillation is now the most commonly performed procedure in most laboratories.

It is well known that pulmonary vein isolation (PVI) is an accepted treatment modality for paroxysmal atrial fibrillation. Since pulmonary veins are the dominant initiating source of atrial fibrillation, the source of atrial fibrillation can be abolished by pulmonary vein isolation (PVI). Pulmonary vein isolation (PVI) involves rendering the tissue between pulmonary veins and the left atrium (LA) to be electrically inactive by an ablation procedure, for all the pulmonary veins. There are normally four pulmonary veins (PV), but many times there are variations in the pulmonary vein anatomy. Generally, the aim is to electrically isolate all the pulmonary veins (i.e. create bidirectional block) such that any triggers arising in the pulmonary veins are not conducted to the left atrium (LA).

Frequently these ablation procedures are performed using cryo ablations or radiofrequency (RF) ablations. Cryo ablations are performed utilizing a cryoballoon catheter, such as one available from Medtronic Inc. The ultimate purpose of cryoablation is to freeze tissue in a discrete and focused fashion to destroy cells in a precisely targeted area. Generally in cryo ablations tissue hypothermia causes cardiomyocytes to become less fluidic as metabolism slows, the ion pumps to lose transport capabilities, and the intracellular pH to become more acidic.

In addition to cryoballoon catheters, other balloon based catheters are also utilized. In one type of balloon based catheter, a laser energy is delivered from inside the balloon for point-by-point pulmonary vein isolation. In another type of balloon catheter, heating is applied for pulmonary vein isolation instead of freezing as with the Arctic Front® cryoballoon catheter.

In the method and system of this disclosure, any of these balloon based catheter may be used for atrial fibrillation ablation utilizing a fluoroscopy and/or medical images based cardiac mapping system of the current invention.

Other forms of ablation energy are also sometimes used, though currently they are not as common. These include, microwave energy ablations, laser ablation, and high frequency ultrasound (HIFU) ablations among others, and their us is within the scope of this disclosure. Even though the cardiac image mapping system disclosed here is described in conjunction with cryoablations, it can be used for other energy forms of ablation, such as RF, Microwave, HIFU, hot balloon and laser ablations.

For RF ablations, a contact force catheter is frequently utilized. Also, for RF ablations a non-fluoroscopic mapping system is frequently utilized. Generally, non-fluoroscopic mapping systems may be impedance based such as St Jude's Navix/Velocity system, or magnetic based such as Biosense Webster Carto mapping system.

For a non-fluoroscopic 3-D mapping system to have utility, the catheters must have sensors which communicate with and which can be registered with the image generated by the mapping system, especially the ablation catheters.

Cryoballoon ablations is one type of ablation procedure whose popularity is increasing rapidly due to many advantages that it offers over RF ablations. One big advantage of cryoballoon ablations is that the whole pulmonary vein is ablated at once, instead of point by point ablations when performed with RF energy catheters.

Cryoballoon catheters do not have sensors for registering to impedance or magnetic based 3D mapping system.

A cryoballoon catheter generally consists of a hollow shaft with a closed distal end containing a cooling electrode tip, integrated thermocouple device and three proximal ring electrodes for recording and pacing. A console that contains the cryorefrigerant fluid. The cooling liquid travels through the inner delivery lumen to the catheter tip, where the cryorefrigerant is pressurized and released. This accelerated liquid-to-gas phase results in rapid cooling of the distal tip. The gas is then conducted away from the catheter tip through a second coaxial return lumen maintained under vacuum and evacuated in the hospital medical gas disposal system.

The console allows the operator two different modes of operation. The first is the cryomapping mode in which the tip is cooled to a temperature not lower than −30 C for a maximum of 80 seconds so as to prevent irreversible tissue damage. The second mode is cryoablation, which results in cooling of the catheter tip to at least −50 C for a programmable period (nominally 4 minutes), producing the permanent lesion. The cryomapping mode can be used for an indefinite number of times before cryoablation. Cryoablation may be initiated at any time during a cryomapping application or, from the onset, if the operator wishes to forego the cryomapping function.

Advantages of cryo ablations include:

Catheter Stability

Hyperthermia generated at the distal cooling electrode, the trial catheter adheres to tissue affording greater catheter stability. The operator may let go of the catheter once it is adhered onto the endocardial surface. The programmed electrical stimulation may be performed during cryoablation without concern for catheter dislodgement. Moreover brushing effects that occurred during beat-to-beat rocketing heart motions and with respiratory variations are eliminated

Minimal Risk of Thromboembolism

To compare the propensity for RF and cryo ablation to produce hot thrombus on the surface of the ablation lesion, a randomize preclinical study was conducted involving 197 ablation lesions in 22 dogs at right atrial, right front, left ventricular sites RF energy was five times more thermogenic than cryoablation, as confirmed by results of historical morphometric analysis seven days after ablation moreover, thrombus volume was significantly greater with RF compared with cryoablation. Interestingly, the extent of IPO thermic injury was positively correlated with thrombus spoke. This was unlike bioenergy, in which lesion that mentions are not predictive of thrombus ice.

Moreover, cryothermal ablation lesions are associated with a lesser degree of platelet and coagulation cascade activation when compared with RF ablation.

Minimal Risk to Vascular Structures

Concerns have been raised regarding RF ablation adjacent to or within coronary venous system or TVs, with venous injury (including acute perforation and Tampanode, and/or delayed fibrosis/stenosis), acute or sub acute and/or luminal venous thrombosis, and collateral damage to the esophagus and/or adjacent coronary arteries being reported. Perforation, or not, and coronary artery stenosis are potential complications. The circumflex and/or coronary artery may course in close proximity to the arrhythmia substrate. Moreover, the AV nodal artery passes near the mouth of the coronary sinus, the ablation may conceivably damage this vessel. Preclinical studies suggest a lower incidence of coronary artery stenosis following cryoablation compared with RF ablation.

Painless Ablation

RF ablation may be painful to the patient under conscious sedation through direct stimulation of cardiac sensory nerves or pericardial or collateral Whisler visceral irritation, particularly when ablating your thin-walled or venous structures such as posterior left atrium, coronary sinus, or posterior cable tricuspid Isthmus. In contrast to our FCA, several studies have noted that again perception, as assessed by standard Likert scale, is significantly less with cryoablation. This first select procedures associated with substantial patient discomfort, the use of cryoablation may theoretically result in lower anesthetic and analgesic requirements. This is especially relevant for electrophysiology laboratories that do not use general anesthesia. However, it should be noted that in the case of AF ablation, a rare incidence of transient ice cream headache has been described during ablation.

Visualization by Ultrasound

The ability to visualize formation of ice ball by ultrasonic means was likewise demonstrated in preclinical transcatheter cryoablation studies. This feature of cryoablation has proved helpful in defining optimal freezing parameters.

GENERAL DISCLOSURE

In the methods and system of this disclosure, a computer based cardiac mapping/EP tools system is disclosed along with the methodology for monitoring esophageal temperature, as well as, a fluoroscopy (or medical images) based mapping for Cryoballoon ablation (or Pulmonary vein isolation PVI). The method and system may also be used for cryoballoon, hot balloon, laser or radiofrequency (RF) atrial fibrillation ablations. It can also be used for any balloon based catheter utilized for atrial fibrillation ablations.

The overall concept of this disclosure is shown in conjunction with FIGS. 1A, 1B, and 1C. Shown in FIG. 1A, a patient's surface and intracardiac signals 566 are brought into the mapping system/computer workstation 550 via interface electronics (not shown). The interface electronics circuitry includes signal amplification, signal conditioning and analog to digital (A/D) conversion. The patient's 552 medical images 557 are also brought into the mapping system/computer workstation 550. The medical images may include a combination of live, real-time images (e.g. fluoroscopy) and stored images (e.g. 3D CT images). The medical images may include fluoroscopy 558, ICE Ultrasound 560, CT images 562, MRI 564 images and others 565. Other images 565 may include computer model of a chamber created with the use of sensors, or with ultrasound based catheters.

The mapping system/computer workstation 550 is configured and programmed to process and manipulate the various images and electrical signals and display them in a manner that is useful to the physician 554, while performing the procedure. Such procedures include ablations for atrial fibrillation and other arrhythmias.

The patient's 552 esophageal temperature may also be monitored 503, and based on pre-determined levels, alarms and/or automatic interrupt may also be activated in the method and system of this disclosure.

As shown in FIG. 1B, various images that are brought into the mapping system/computer workstation 550 are processed. In some cases the images are overlaid or stacked 505 on top of each other in layers. The images (when stacked and overlaid) may also be moved so that they are aligned properly. This may be for two images or more images. In some cases more than two images are stacked 505. The system is configured such that two or more layers of images can be overlaid on top 505 of each other and the transparency of the images can be adjusted by an operator, to provide useful information regarding anatomy, and especially for the placement of a catheter in an appropriate position such as appropriate position in the left atrium, pulmonary vein os or other appropriate structures.

Also disclosed are methods and system for tagging or marking on the images, such as marking ablation sites for cryoballoon ablations, and storing images (shown in conjunction with FIG. 1C). The ablation tags marked for cryoballoon ablations may be displayed in a review screen to aid in ablations performed with any balloon catheter, for example a cryoballoon catheter for pulmonary vein isolation for atrial fibrillation ablations. Same can be done with other balloon based catheters The general methodology for the system is described in conjunction with the flow diagram in FIG. 1D for cryoballoon ablations and FIG. 1E for radiofrequency ablations.

For cryoballoon ablations, as shown in conjunction with FIG. 1D, at the beginning of the procedure (step 450), the patient is connected to the fluoroscopy based mapping step 452. Also, an esophageal probe is placed at the appropriate level of the esophagus for measuring esophageal temperature (steps 454 & 456) and connected to the mapping system 458.

In the setup of the Mapping System 458, fluoroscopy and/or medical images (e.g. intracardiac echo or ICE) are acquired into the mapping system (step 464), as well as, patient's electrical signals (both intracardiac and surface EKG) as shown in step 460. Esophageal temperature is also acquired into the Mapping System 458, and temperature based alarms and/or automatic shutoff is programmed in the computer at the beginning of the case, based on change from the baseline temperature.

The role of the mapping system is to help place the cryoballoon catheter in the appropriate location with the left atrium and pulmonary veins. To this end, high resolution images are recorded in the system with contrast medium ("dye") injections. The recordings may be done manually by the operator who manually starts and stop the recordings, or may be done in an automatic fashion utilizing optical character recognition (OCR) as a switch, described later in this disclosure.

Once the detailed images of the pulmonary veins are recorded, (step 466) the live fluoroscopy images are superimposed on the "enhanced" images of the pulmonary veins (obtained with "dye" injections), as shown in step 468 and described later in this application. Once the two images are superimposed, a transparency factor between the live image and recorded image is adjusted (step 470) to guide the physician in placing the cryoballoon in the appropriate position, step 472. Once the cryoballoon is placed appropriately, freezing or cryoablation is started at physician's orders.

Advantageously, in this procedure the system not only guides in the optimal visual placement of the cryoballoon, but also monitors the esophageal temperature (optional), and the system acts to activate alarms and/or cut-off the ablation energy delivery based on pre-determined criteria as was set in step 462.

As well known in the art, atrial fibrillation ablations may be performed utilizing radiofrequency (RF) ablation or cryoablations (or other forms of energy). The system described in this disclosure may be used for RF or cryoablations (or other forms of energy). The flowchart in FIG. 1E describes similar steps for RF ablations. These are steps 480 from beginning of procedure to step 508 to the end of the procedure. Even though the methodology for sequence of events is similar, radiofrequency ablations is generally a much more lengthier procedure as the ablation lesions are performed point by point via a much smaller catheter, typically also containing means for contact force sensing.

The posterior wall of the left atrium is particularly targeted for ablation because the pulmonary veins enter the atrium at this area of the left atrium, encircling the pulmonary veins with continuous rings of lesions in this procedure. The esophagus may however be, in a position so as to overlie one or more of these circles, thereby making the desired encirclement difficult or impossible.

A significant and lethal complication of atrial fibrillation ablation is the accidental creation of an atrial esophageal fistula following the development of lesions on the posterior wall of the left atrium. Because the esophagus is generally in close position to the posterior wall of the left atrial, thermal injury may be communicated to the esophageal wall resulting in disruption of the wall and formation of the atrial esophageal fistula. Thermal esophageal lesions are believed to be precursors of fistula formation. Post ablation esophageal wall changes (erosion or ulceration) are reported to occur in up to 47% of patients. Real time temperature monitoring can detect rapid esophageal heating during radiofrequency ablation.

Although the pathophysiology of left atrial-esophageal (LA-Eso) fistula formation is not fully understood, it is clear that thermal injury to the esophagus during ablation of the LA posterior wall plays a crucial role in triggering the cascade of events that eventually result in the development of LA-Eso fistula.

Currently, the most commonly used clinical strategy to minimize esophageal thermal injury during AF ablation involves limiting the magnitude of power 25 to 35 W, as well as the duration (<30 s), of RF applications placed along the posterior wall of the LA. A major limitation of this approach is that it fails to account for the variability in the thickness of the posterior LA wall and the presence of peri-esophageal connective tissue—important determinants of esophageal heating. Thus, empirically limiting the power and duration of RF applications may be insufficient to prevent esophageal thermal injury in all patients. RF power delivery during AF ablation, guided by luminal esophageal temperature (LET) monitoring is associated with less frequent esophageal injury compared with a strategy of power limitation alone.

Also, it is known that successful atrial fibrillation ablation may require the introduction of lesions near the location of the inferior right pulmonary vein, which is located in close proximity to the phrenic nerve. Thus, it has become more common for accidental injury to the phrenic nerve to occur. The phrenic nerve is responsible for operation of the diaphragm, and thus, injury to the phrenic nerve can be quite catastrophic.

Luminal esophageal temperature (LET) monitoring is the most common strategy to minimize esophageal injury during atrial fibrillation (AF) ablation procedures. The esophageal probe may have one thermistor, or the esophageal probe may have multiple sensors on the body of the probe for measuring temperature from a length of the esophagus.

In addition to the foregoing, fractionated electrograms and vagal plexi are also frequently present on the posterior wall of the left atrium. These are also common targets of atrial fibrillation ablation. Again, the location of the esophagus may hinder application of this sufficient energy to successfully ablate enough energy of the left atrium to prevent recurrence of atrial fibrillation.

Since esophageal injury during RF ablation in the left atrium is thermal injury, and because of the need for preventing injury to the esophagus, there is a real need for a method and system for,
a) activating various levels of alarms based on esophageal temperature monitoring,
b) cooling the esophagus, and/or
c) automatically interrupting the energy delivery of the ablation circuit, whenever the esophageal temperature reaches a predetermined critical level.

SUMMARY OF THE DISCLOSURE

The current disclosure discloses methods and system for atrial fibrillation ablations utilizing a fluoroscopy and/or medical image(s) based cardiac mapping system adapted for balloon based catheters including cryoballoon catheter. The method and system incorporates overlaying two or more sets of images on top of each other where the transparency between the images can be adjusted as an aid in the optimal placement of the balloon based catheters. Further, tags and markers are also placed on fluoroscopic and/or other medical images indicative of where the tissue that has been ablated. The method and system also comprises the ability to monitor esophageal temperature, and to activate alarms and/or energy delivery interrupt based on pre-determined esophageal temperature parameters.

Accordingly, one objective of the disclosure is for a computer based system to overlay fluoroscopic and other medical images to aid in placing a balloon based catheter in the appropriate location with left atrial chamber or around pulmonary vein for performing pulmonary vein isolations for treatment of atrial fibrillation.

In another aspect of the disclosure, the cardiac system is a combination system comprising of a fluoroscope or medical images based cardiac mapping system and a temperature control system.

In another aspect of the disclosure, the fluoroscope or medical images based cardiac mapping system provides guidance to the physician for proper placement of cryoballoon catheter for cryoablation.

In another aspect of the disclosure, the fluoroscope or medical images based cardiac mapping system provides guidance to the physician for proper placement of a circular catheter for radiofrequency (RF) ablations.

In another aspect of the disclosure, the fluoroscope or medical images based cardiac mapping system utilizes fluoroscopy for electroanatomical mapping.

In another aspect of the disclosure, the fluoroscope or medical images based cardiac mapping system utilizes intra-cardiac echo (ICE) for electroanatomical mapping.

In another aspect of the disclosure, the fluoroscope or medical images based cardiac mapping system utilizes a combination of fluoroscopy and intra-cardiac echo (ICE) for electroanatomical mapping.

In another aspect of the disclosure, the fluoroscope or medical images based cardiac mapping system utilizes computed tomography (CT) for electroanatomical mapping.

In another aspect of the disclosure, the fluoroscope or medical images based cardiac mapping system utilizes magnetic resonance imaging (MRI) for electroanatomical mapping.

In another aspect of the disclosure, the fluoroscope or medical images based cardiac mapping system utilizes a combination of different type of imaging modality for electroanatomical mapping.

In another aspect of the disclosure, the fluoroscope or medical images based cardiac mapping system utilizes a combination of recorded high resolution fluoroscopy and live fluoroscopy for electroanatomical mapping.

In another aspect of the disclosure, the mapping system is intended for aiding the physician perform atrial fibrillation procedures utilizing balloon based catheters.

In another aspect of the disclosure, the balloon based catheter is for cryoballoon ablations.

In another aspect of the disclosure, the balloon based catheter may be for laser ablation of pulmonary veins.

In another aspect of the disclosure, the balloon based catheter may be for heating ablation for pulmonary vein isolation.

In another aspect of the disclosure, the medical images utilized are one or more from a group comprising of, stored fluoroscopy image, stored fluoroscopy video, recorded high resolution fluoroscopy with contrast medium (dye) injection, CT images, MRI images, ultrasound images, 3D fluoroscopy models, electrical impedance based computer image model, magnetic system based computer model, impedance and magnetic based computer model, or ultrasound catheter based image model.

In another aspect of the disclosure, two or more types of images may be overlaid on top of each other, where the operator can adjust a transparency factor between the images to take advantage of more detailed anatomy for a guide in placement of the catheter.

In another aspect of the disclosure, the overlaying of two or more sets of images includes a recorded fluoroscopy image(s) with contrast medium injection and a live fluoroscopy image(s).

In another aspect of the disclosure, the overlaying of two or more sets of images includes a recorded fluoroscopy image(s) with contrast medium injection and a CT image model.

In another aspect of the disclosure, a CT image (model) is displayed next to two layers of fluoroscopy images on top of each other.

In another aspect of the disclosure, the overlaying of two or more sets of images includes a recorded fluoroscopy image(s) with contrast medium injection, a CT image model, live fluoroscopy image(s).

In another aspect of the disclosure, the coding may utilize software which is one from a group comprising LAB WINDOWS/CVI, LABVIEW (National Instruments Corp.), C, C+, Microsoft Visual C++, Dot Net framework, MATLAB, and Microsoft Visual Basic, or any functional equivalent software language.

In another aspect of the disclosure, the markers or tags are placed on fluoroscopy and/or medical image(s) which are indicative of where tissue ablation was performed.

In another aspect of the disclosure, the markers or tags may be on a two dimensional images(s) or three dimensional models.

The current disclosure also discloses novel methods and system for increasing safety of atrial fibrillation ablations by monitoring and interrupting energy delivery of ablation procedure, based on increases in the esophageal temperature.

The method and system of this disclosure also comprises a computer with software configured and programmed to set one or more alarms and/or computer based interrupt (shut-off) based on pre-selected levels during a cardiac ablation procedure, more specifically an atrial fibrillation procedure. Such levels can be, but not limited to, elevation in temperature level(s), or time duration of such elevation of temperature levels. The physician may select the level(s) or settings of one or more variables to suit individual patient needs. The method is configured to either set off alarm(s) or shut off the energy for the procedure or both. The baseline temperature, elevation in temperature level(s), or time duration or delay of such elevation of temperature levels have a range for the physician to select from. The range for duration may be from milli-seconds to several seconds In one aspect of the disclosure, when esophageal temperature increases above a first level predetermined threshold, an audio alarm is activated.

In another aspect of the disclosure, when esophageal temperature increases above a first level of predetermined threshold, an audio and visual alarm is activated.

In another aspect of the disclosure, when esophageal temperature increases above a second level predetermined threshold, a higher level of audio alarm is activated.

In another aspect of the disclosure, the predetermined event may be an increased level of esophageal temperature.

In another aspect of the disclosure, the predetermined event may be the rate of change of esophageal temperature.

In another aspect of the disclosure, the esophageal probe may comprise ten temperature sensors.

In another aspect of the disclosure, the esophageal probe may comprise 12 temperature sensors.

In another aspect of the disclosure, the esophageal probe may comprise one temperature sensor.

In another aspect of the disclosure, the esophageal probe may comprise any number of temperature sensors.

In another aspect of the disclosure, the esophageal probe may comprise thermistor sensors.

In another aspect of the disclosure, the esophageal probe may comprise thermocouple sensors.

In another aspect of the disclosure, the esophageal probe may have a body which straight in shape.

In another aspect of the disclosure, the esophageal probe may have a body which has a preformed shape.

In another aspect of the disclosure, the esophageal probe may have a body which has a preformed shape and can be straightened with a straight stylet.

In another aspect of the disclosure, when esophageal temperature increases above a second level predetermined threshold, a higher level of audio and visual alarm is activated.

In another aspect of the disclosure, when esophageal temperature increases above a first level of predetermined threshold, a siren is activated.

In another aspect of the disclosure, when esophageal temperature increases above a second level predetermined threshold, a higher level of a siren is activated.

In another aspect of the disclosure, when esophageal temperature increases above a predetermined threshold, the ablation energy to the heart tissue is interrupted.

In another aspect of the disclosure, the ablation energy to the heart tissue is interrupted based on increase in temperature and time duration of elevated temperature.

In another embodiment, the computer logic for esophageal temperature monitoring and corresponding alarms and interrupt logic and circuitry is incorporated within the ablation generator system.

In another aspect of the procedure, a method of eliminating/minimizing esophageal temperature related injury during atrial fibrillation cardiac ablation procedure is provided.

In another aspect of the disclosure, esophageal injury during ablation is minimized by cooling the esophagus, if the esophageal temperature increases.

In another aspect of the disclosure, the esophagus is cooled by cold saline which is brought into a balloon adapted to in the esophagus.

In another aspect of the disclosure, the cooling of the esophagus is done using gases.

In another aspect of the disclosure, cooling of the esophagus is done with in combination with alarms.

In another aspect of the disclosure, cooling of the esophagus is done with in combination with ablation energy interrupt.

In one embodiment, the computer logic for esophageal temperature monitoring and corresponding alarms and interrupt logic is in a stand-alone computer in parallel to the patient monitoring system.

In another embodiment, the computer logic for esophageal temperature monitoring and corresponding alarms and/or interrupt logic is in a stand-alone computer where the esophageal signals to the stand-alone computer are obtained from the patient monitoring system.

In another embodiment, the computer logic for esophageal temperature monitoring and corresponding alarms and interrupt logic is in a stand-alone computer used independently of the patient monitoring system.

In another embodiment, the computer logic for esophageal temperature monitoring and corresponding alarms and interrupt logic and circuitry is incorporated within the patient monitoring system.

In another embodiment, the computer logic for esophageal temperature monitoring and corresponding alarms and interrupt logic and circuitry is incorporated within a 2-D or 3-D mapping system.

In another embodiment, the computer logic for esophageal temperature monitoring and corresponding alarms and interrupt logic and circuitry is incorporated within a fluoroscopy or medical images based cardiac mapping system.

Various other features, objects and advantages of the disclosure will be made apparent from the following description taken together with the drawings.

BRIEF DESCRIPTION OF THE DRAWINGS

For the purpose of illustrating this disclosure, there are shown in accompanying drawing forms which are presently preferred, it being understood that the disclosure is not intended to be limited to the precise arrangement and instrumentalities shown.

FIGS. 17A and 17B shows embodiments of esophageal probe that that are pre-formed.

FIGS. 18A and 18B show two embodiments where multiple sensors are on a inflatable apparatus. In FIG. 18A, the sensors are covered in a sheath or membrane. In FIG. 18B the sensors on an inflatable apparatus are exposed

FIG. 28 is a flow diagram showing the steps for automatically recording multiple video loops from fluoroscopy, while the fluoroscopy is on.

FIG. 38 is a block diagram depicting CT images overlaid on top of recorded fluoroscopy images and live fluoroscopy overlaid on top of that.

FIG. 42 is a block diagram depicting MRI imaging overlaid on recorded fluoroscopy, and live fluoroscopy overlaid on top of that.

FIG. 45 is a diagram showing a recording of fluoroscopy with contrast medium ("dye") injection.

FIG. 46 is a diagram showing a recording of fluoroscopy with contrast medium ("dye") injection close to left superior vein.

FIG. 47 is a diagram showing an example of one implementation where live fluoroscopy and recorded are overlaid on top of each other and the transparency between the two images has been adjusted. Further, electrical signals are also displayed on the top image.

FIG. 48 is a diagram showing an example of a CT image with volume rendering which can be combined with fluoroscopy and/or other types of medical images.

DETAILED DESCRIPTION OF THE DISCLOSURE

The following description is of the best mode presently contemplated for carrying out the disclosure. This description is not to be taken in a limiting sense, but is made merely for the purpose of describing the general principles of the disclosure. The scope of the disclosure should be determined with reference to the claims.

Figure 1A:
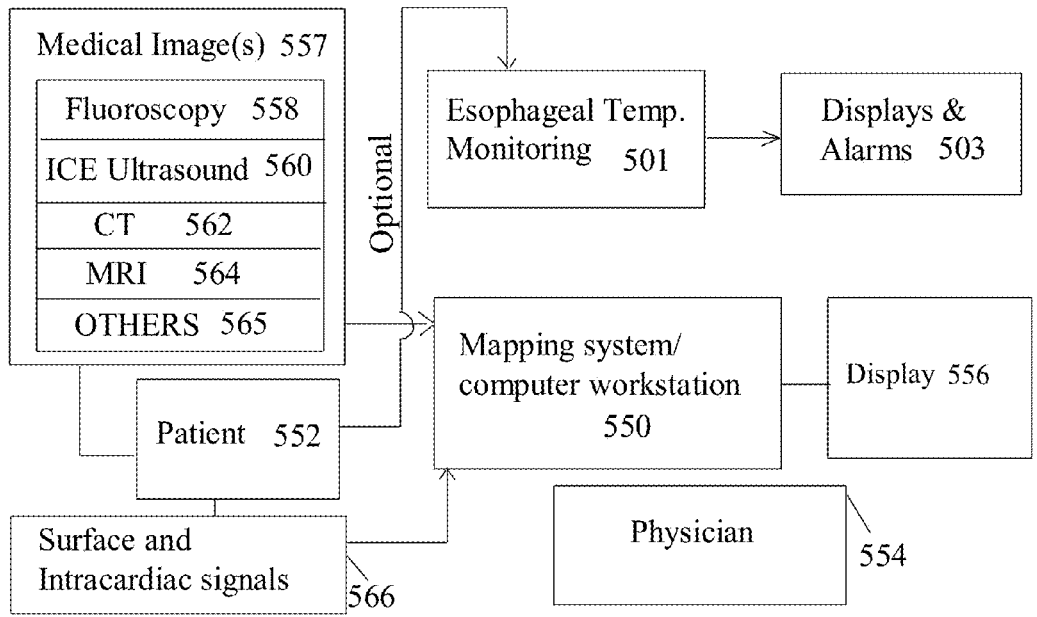
FIG. 1A is a block diagram showing overall concept of medical imaging based mapping system and temperature monitoring.
Figure 1B:
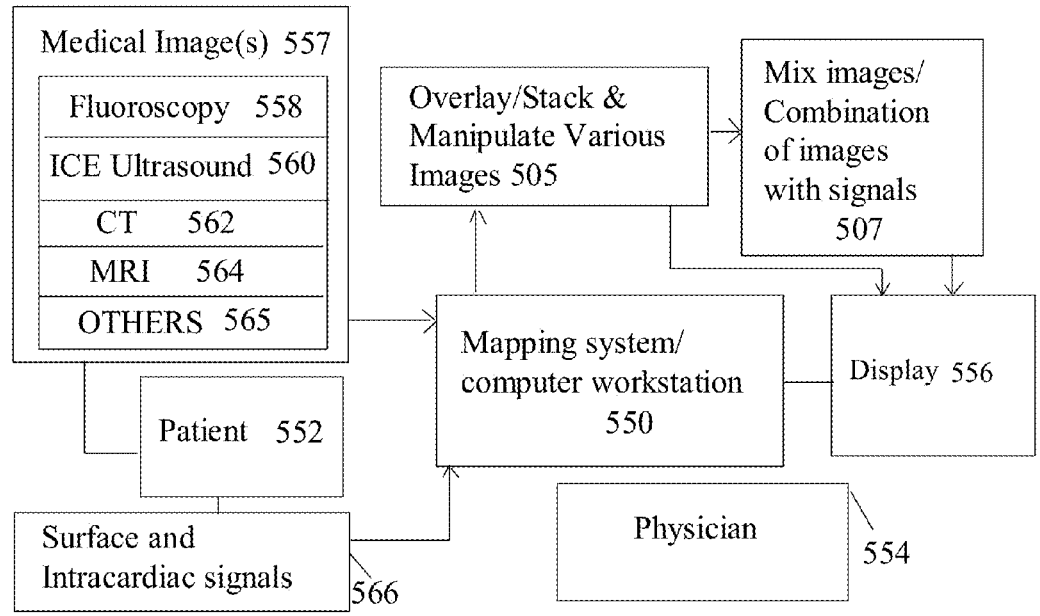
FIG. 1B is a block diagram showing the concept of the mapping system including overlaying/stacking of various images and combining various images with signals.
Figure 1C:
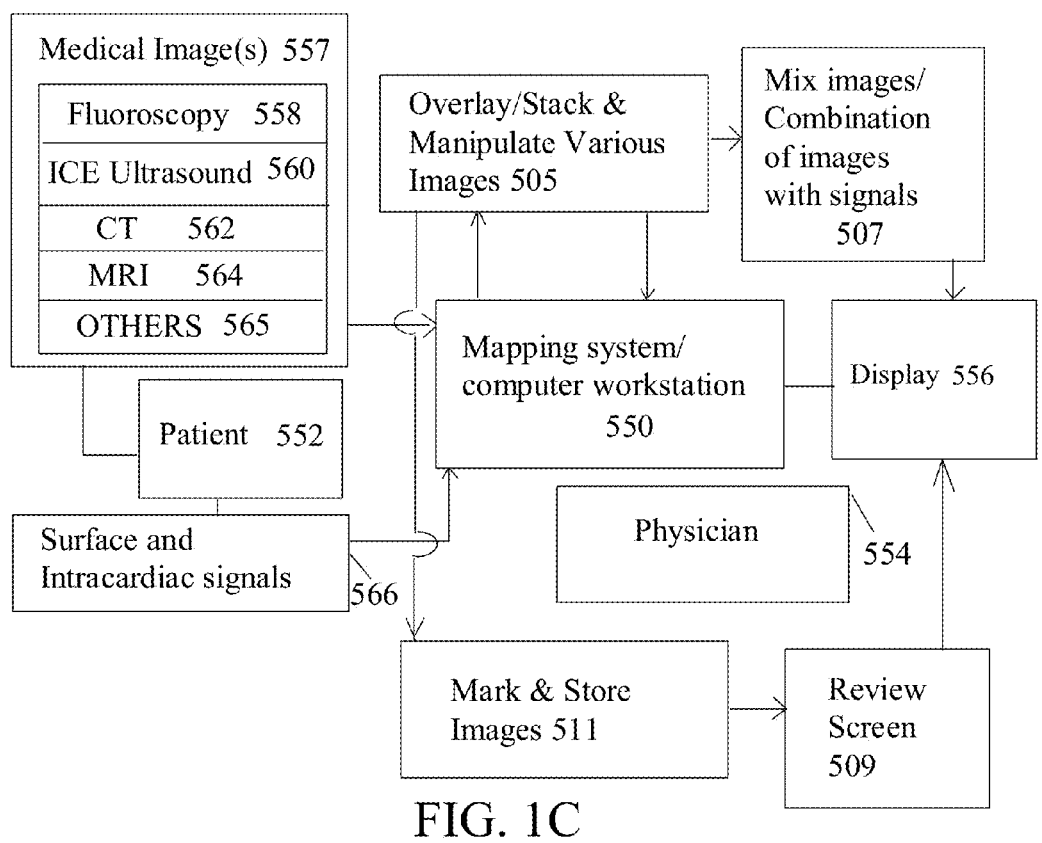
FIG. 1C is a block diagram showing the concept of the mapping system including overlaying/stacking of various images and marking and storing images.
Figure 1D:
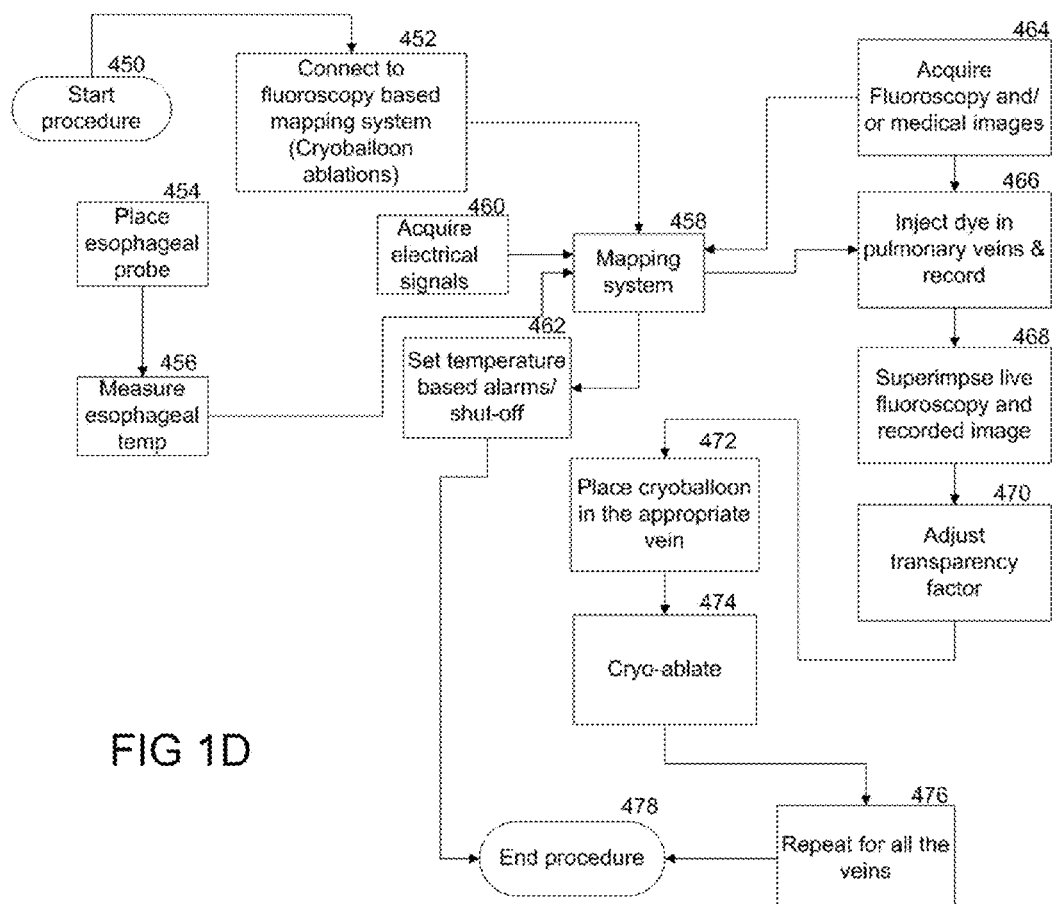
FIG. 1D is a flow diagram detailing connecting and operating temperature monitoring system and mapping system for cryoballoon ablations.
Figure 1:
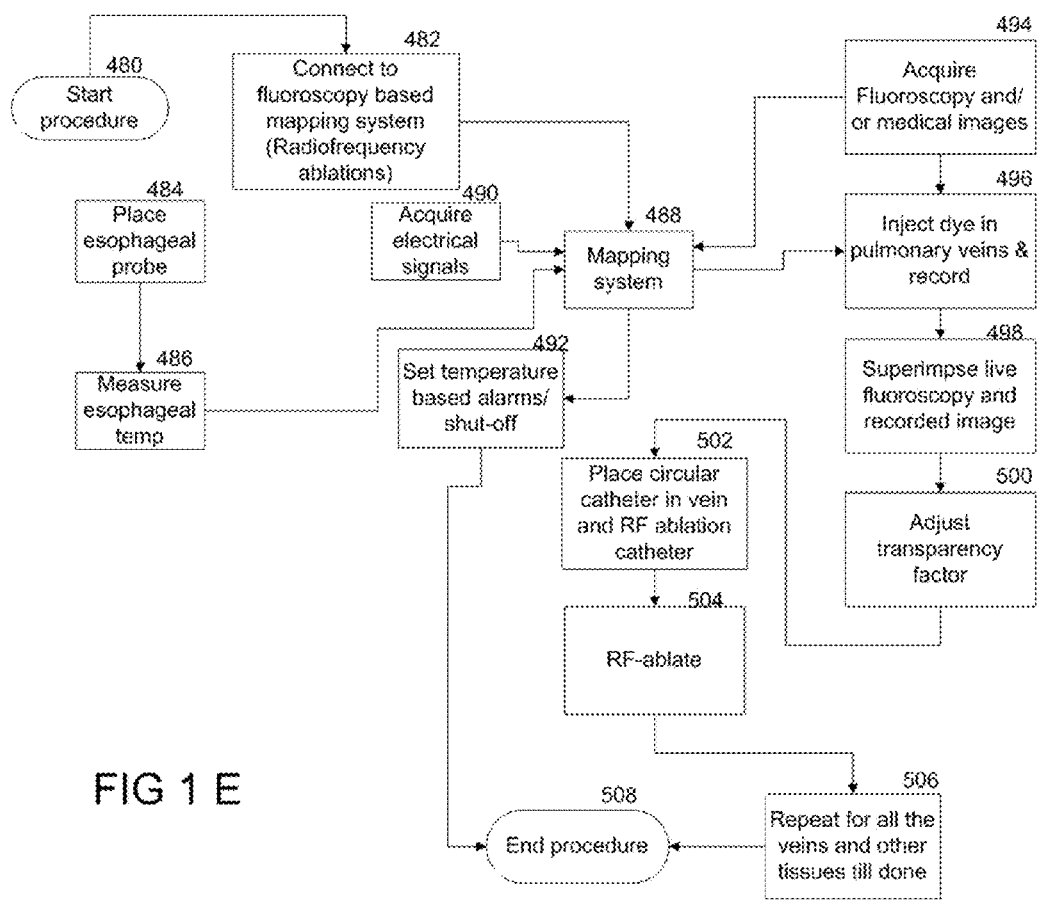
FIG. 1E is a flow diagram detailing connecting and operating temperature monitoring system and mapping system for radiofrequency (RF) ablations.
FIG. 1F is a block diagram of the concept of alarms and computer controlled interrupt based on esophageal temperature for atrial fibrillation ablations.
Figure 1F:
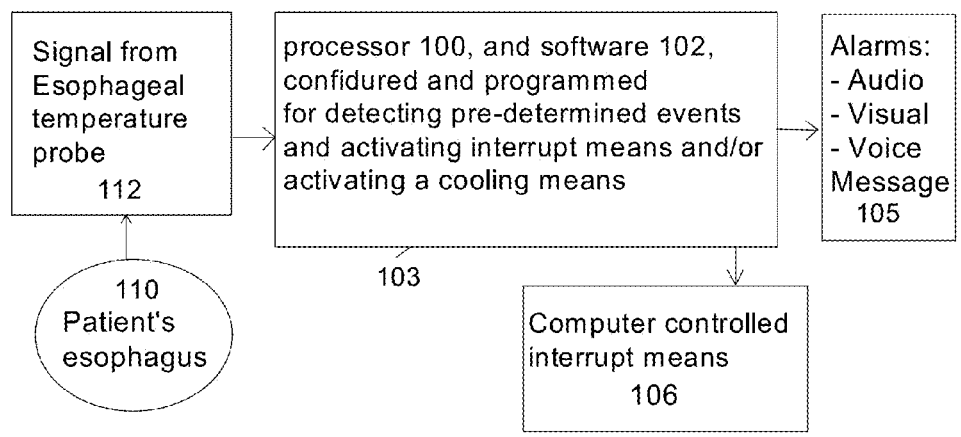

This disclosure is targeted to preventing or minimizing thermal injury to the esophagus or the vagus nerve(s) during ablation in the atrium, for treatment of atrial fibrillation. Accordingly, as shown in conjunction with FIG. 1F signals are typically and routinely recorded from an esophageal temperature probe 112 which is in a patient's esophagus 110.

The temperature probe may comprise a single or multiple thermisters. The multiple thermister probe may comprise any number of thermisters. In one preferred embodiment, the temperature probe may have ten thermistors. In other embodiments the probe the probe may have any number of thermisters. The goal is to cover the whole esophageal region, which could correspond to the left atrium. Another goal is that the coverage is large enough so the physician shouldn't have to move the esophageal probe during the procedure.

The temperature information is typically processed by a computer 103 comprising a processor 100 with algorithms 102 for pre-determined events, and displayed on a patient monitor which may be a stand-alone patient monitor or part of an anesthesia monitoring setup, or a cardiac recoding/monitoring system. During an atrial fibrillation ablation procedure this monitoring is typically done by an anesthesiologist, a nurse or an electrophysiologist performing this procedure. In the method and system of this disclosure, various levels of alarms and controls are incorporated within the monitoring system, such that at a programmable level there is an alarm indication that the temperature on the esophageal probe 112 has increased by a pre-determined level selected by the physician. This is shown in blocks 103 and 105 in FIG. 1F. A second level(s) of alarms may also be established, indicating a further level of increase at the esophageal temperature probe. Finally, upon reaching a higher predetermined level of temperature increase, the computer may activate an interrupt means which may be a relay switch 106 or any other types of circuit breakers without limitation, which interrupts the energy delivery to the ablation circuit. At that point the physician either re-positions the catheter to another position in the atrium which is further away from the esophagus or waits for the temperature in the esophageal probe to come back down before resuming the ablation at that point.

Figure 2A:
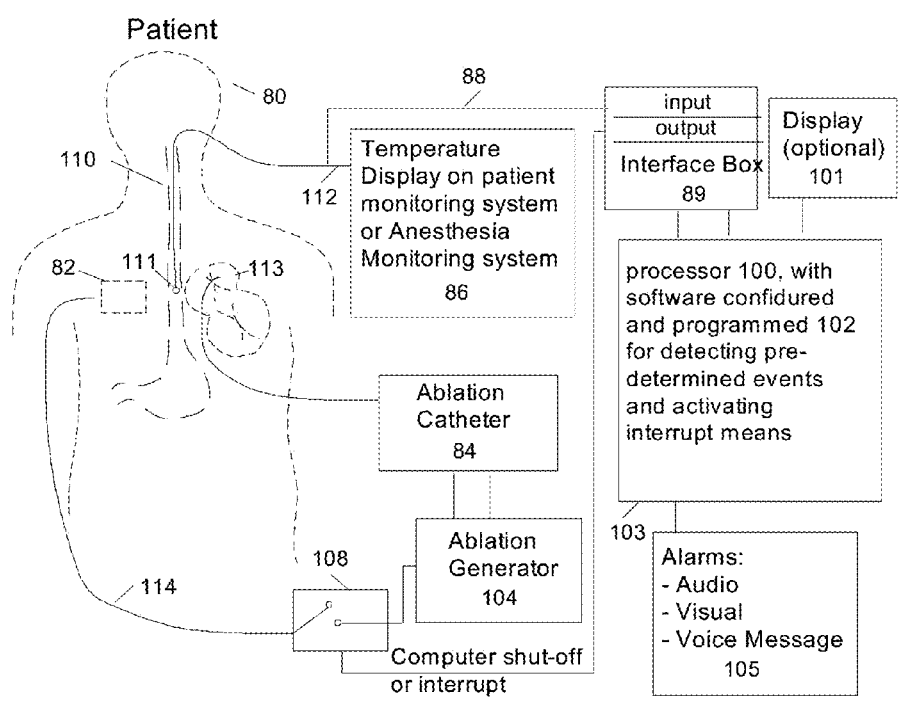
FIG. 2A depicts a general setup of the concept where the esophageal signals from the patient are split and slaved into another computer for monitoring, analyzing and interrupting atrial fibrillation ablation procedure.

This concept and various embodiments are described below in conjunction with FIGS. 2A-7. Shown in FIG. 2A is a schematic block diagram of one preferred embodiment of the disclosure. As shown in the figure an esophageal probe 112 is placed in the patient 80, such that the temperature probe 111 (usually a thermistor or a thermocouple) is in the esophagus 110 at the level of the left atrium 113, preferably at the level of the tip of the ablation catheter, and generally close to the ablation catheter which is in the left atrium 113.

In one embodiment the signal from the esophageal probe 112 is spilt or the signal is slaved 88 into an interface box 89 such that the information can be analyzed by a computer of the patient monitoring system 86, which is typically observed and monitored visually by the anesthesiologist or a nurse, and an additional computer 103 comprising processor 100 and algorithms 102 (software which is configured and programmed as described in the disclosure). In this disclosure, software and algorithms may be used interchangeably.

In one preferred embodiment, the signals from the probe are brought into a computer based system. The computer based system may be a cardiac mapping system, a cardiac monitoring/recording system, or a stand-alone system.

Figure 8A:
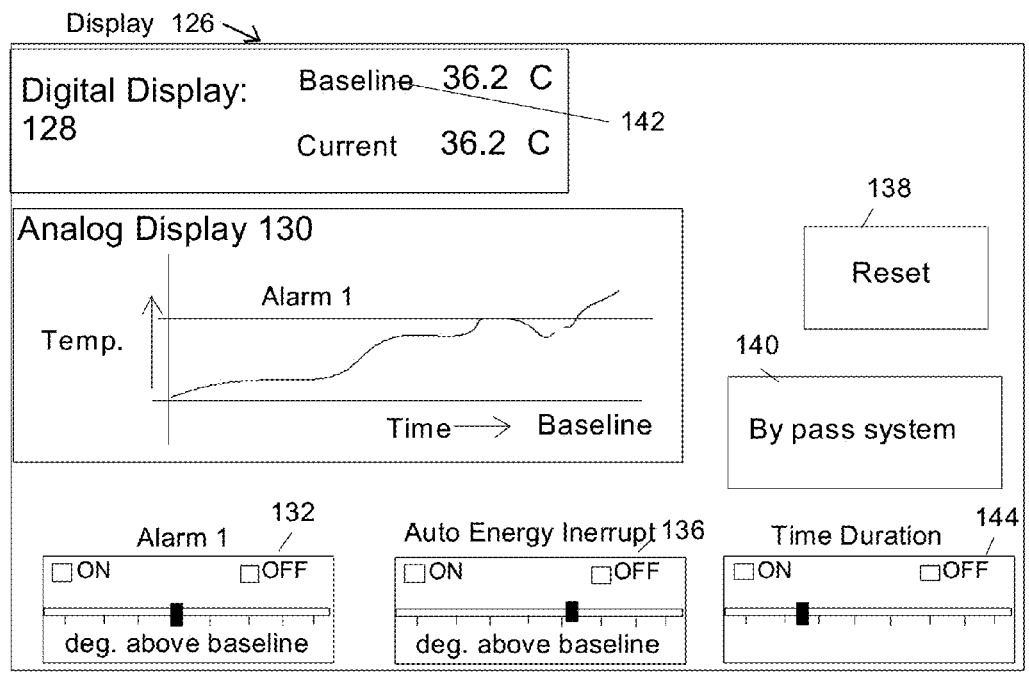
FIG. 8A shows an example of graphical display and graphical interface of the concept.

The slaved signals 88 which are brought into the separate computer 103 (via the interface box 89) are analyzed and displayed 101. The display is both in the form of graphs and digital readout of temperature, and is described later in conjunction with FIGS. 8A, 8B, 9D. The computer 103 comprises software which is configured and programmed to monitor temperature levels, and trigger one or more level(s) of alarm(s) and/or activate ablation interrupt, when predetermined threshold limits are reached. In one aspect, at the start of the ablation procedure the baseline temperature of the patient is set into the computer by the operator. This value acts as the baseline for any increase in temperature as the ablation procedure progresses, and various lesions are delivered. Typically numerous lesions are delivered during the course of the ablation procedure. Without limitation in one embodiment, there are two levels of alarms, after which an automatic interrupt takes over computer controlled by a relay switch or other interrupt means. In another embodiment, there are more than two levels of alarms.

The following description is meant to be illustrative and not limiting. In one embodiment the first alarm is set to a first value, which is a threshold value that can be easily entered or adjusted on the graphical interface of the computer (shown later in conjunction with FIG. 8A, 8B, 9D). When the first level of alarm is reached there is both sound warning and an optional light warning coming from the interface box (or the computer). When the second level of alarm is reached, both the audio and visual levels get stronger (or more intense). Finally, when the temperature reaches the next level, which is pre-determined or pre-defined by the healthcare operator, there is a computer controlled temporary interrupt or shut-off of the energy delivery from the ablation generator 104. As shown in conjunction with FIG. 2A, upon detection of the limit by the software the computer 103 gives a command signal via the interface box 89, such that the relay switch 108 (as one example of interrupt means) which is placed in the ablation circuit is opened and the energy delivery is interrupted. At this point, the physician either repositions the catheter to a site further away from the esophagus 110, or waits for the temperature to come back down. The ablation energy delivery can be re-started at any time by simply re-setting the switch using either a software or a hardware switch.

In the example of the above embodiment, say the physician has the first alarm set to a level of 0.25° C., the second alarm set to a level of 0.50° C., and the third alarm set to a level of 1.0° C. When the temperature increases to above 0.25° C. of the baseline, a beep or buzzer sound is activated along with the flashing light. At this point the physician may steer the catheter to a site which is further away from the esophagus 110 or may hold off on the energy delivery, or may finish the current burn being aware that this is the first alarm. If the temperature continues going up, and reaches the pre-determined threshold for the second level of alarm, the physician may more readily interrupt the ablation burn, unless at a critical point or seconds away from finishing the current burn. If at any time, the temperature reaches the threshold for automatic interrupt or shut-off, a command signal from the computer 103 via the output side of the interface box 89, opens the relay switch 108 interrupting the ablation circuit, and stopping the energy delivery to the tissues. At this point the physician or the operator resets the circuit. Again the physician may keep ablating after moving the catheter to a site which is further away from the esophagus 110 or wait until the temperature drops back down to a normal level before ablating again.

An example of first alarm may be a buzzer, a tone, or intermittent beeps. In such a case the second alarm may be a higher level of buzzer, tone, or more frequent beeps indicating a higher level of concern than the first alarm. In the case of a flashing light or LED, the second level of alarm may be more rapid and more intense flashing or higher frequency of LED flashing. There may also be an additional voice message also reciting the values of the temperature measurement. The above are examples only, and are not meant to be limiting. In the case of an automatic computer based interrupt or shut-off, the software may be configured and programmed such that as the temperature drops back to a pre-determined normal level, the system switch will reset itself.

Since sustained elevated temperatures may be related to thermal injury, in one embodiment the automated shut-off may be a combination of higher than baseline temperature and time duration. For example the elevated temperatures stay at a higher level for an adjustable and programmable period of time. Therefore in this embodiment the auto shut-off is based on increases in temperature and time duration of elevated temperature.

Figure 2B:
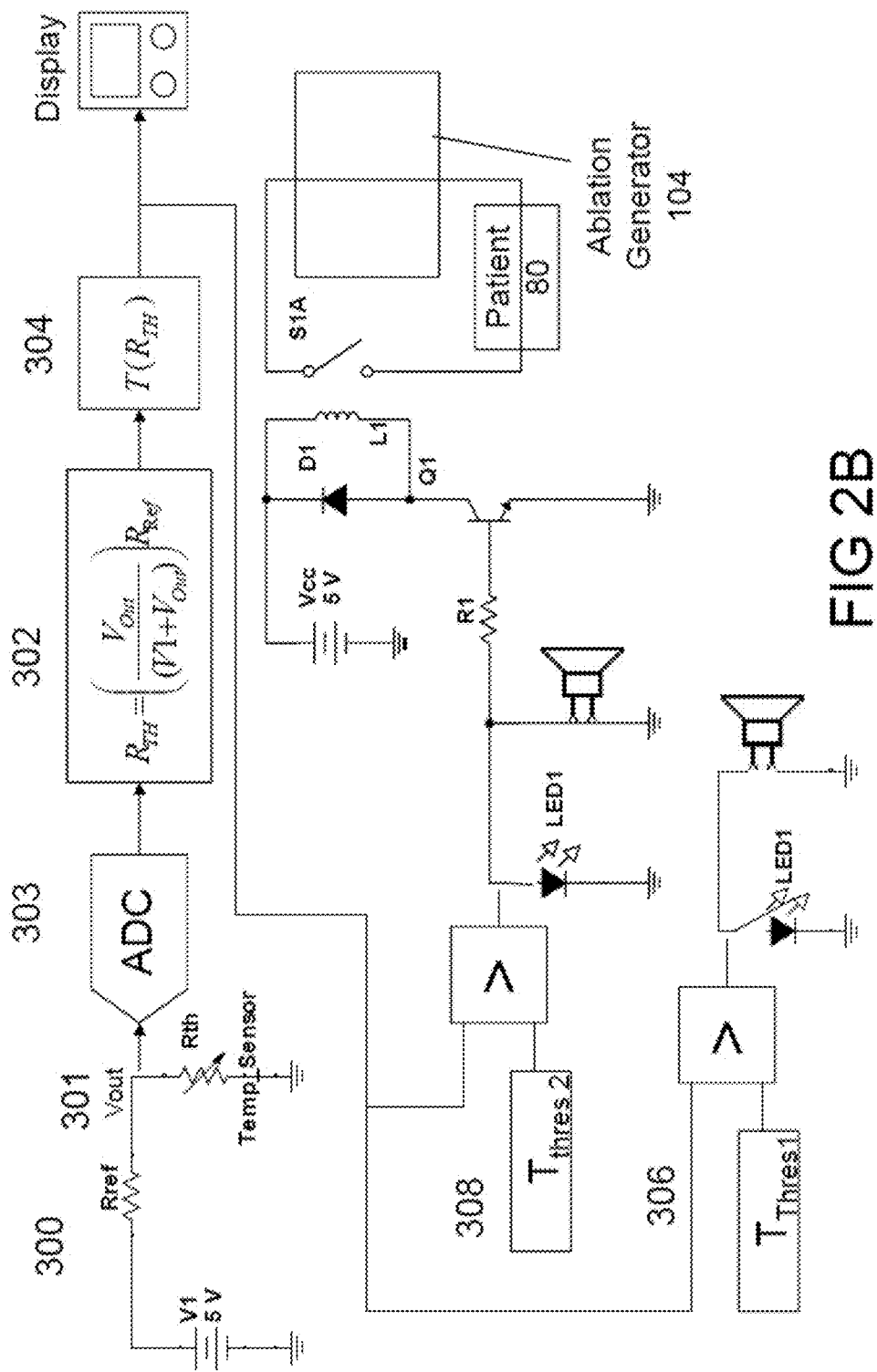
FIG. 2B depicts one implementation of the system and method.

Shown in FIG. 2B is a block and circuit diagram for one implementation of this disclosure. Other functionally equivalent circuitry can also be used. The temperature sensor setup in block 300 outputs a voltage that varies with temperature 301, in a thermister based system. The analog voltage signal is converted to digital signal by the ADC 303 and transformed to an impedance change 302 where $R_{Ref}$ is a reference resistor chosen close to operating impedance of the temperature sensor. Shown in block 304, the impedance is converted to a temperature change using sensor specifications.

The temperature is compared to the first threshold 306 and if it's greater, an LED 307 and sound alarm 309 are activated. As shown in 308, if the temperature exceeds the second threshold, a relay is also activated that switches off the ablation generator 104 or interrupts the energy delivery. Using similar methodology, more than one level of alarm may be used (not shown in the figure).

It will be clear to one of ordinary skill in the art, that the above concept can be practiced in various ways. For example, as shown in conjunction with FIG. 3, instead of splitting or slaving the temperature signal into both the patient monitor and another computer 103, the second set of signals to computer 103 may be gotten directly from the patient monitoring system 86 into the interface box. This simplifies the connections, providing that there is an output available from the patient monitoring system 86.

In one embodiment, the concept may be practiced independent of the patient monitoring system or anesthesia monitoring system. In this embodiment, as shown in conjunction with FIG. 4, the esophageal temperature probe 112 is connected directly to the interface box 89, which sends signals to the computer 103 which has the processor 100 with software configured and programmed with algorithms 102 capable of detecting pre-determined events. In this embodiment the anesthesiologist is relieved of the burden of monitoring esophageal temperature.

In one embodiment, the algorithms for detection of esophageal temperature alarm 102, limits and logic for automatic computer shut-off or interrupt 106 may be incorporated into the computer of a patient monitoring system 86. This embodiment is shown schematically in conjunction with FIG. 5. The esophageal probe 112 is connected to the monitoring system or anesthesia monitoring system 86 in the usual manner. In this embodiment, the software with algorithms 102 of the system 116 is configured and programmed to incorporate the algorithms for detection of out of range limits. Further, under conditions where an automatic interrupt or shut-off is warranted, an interface unit 117 connects to the relay switch 108 (or other interrupt means) for the shut-off or interrupt. In this embodiment, the patient monitoring system 116 is also configured with audio alarms, visual alarms, and voice messages 105. The advantage of this embodiment is that a second parallel computer is not required.

Figure 6:
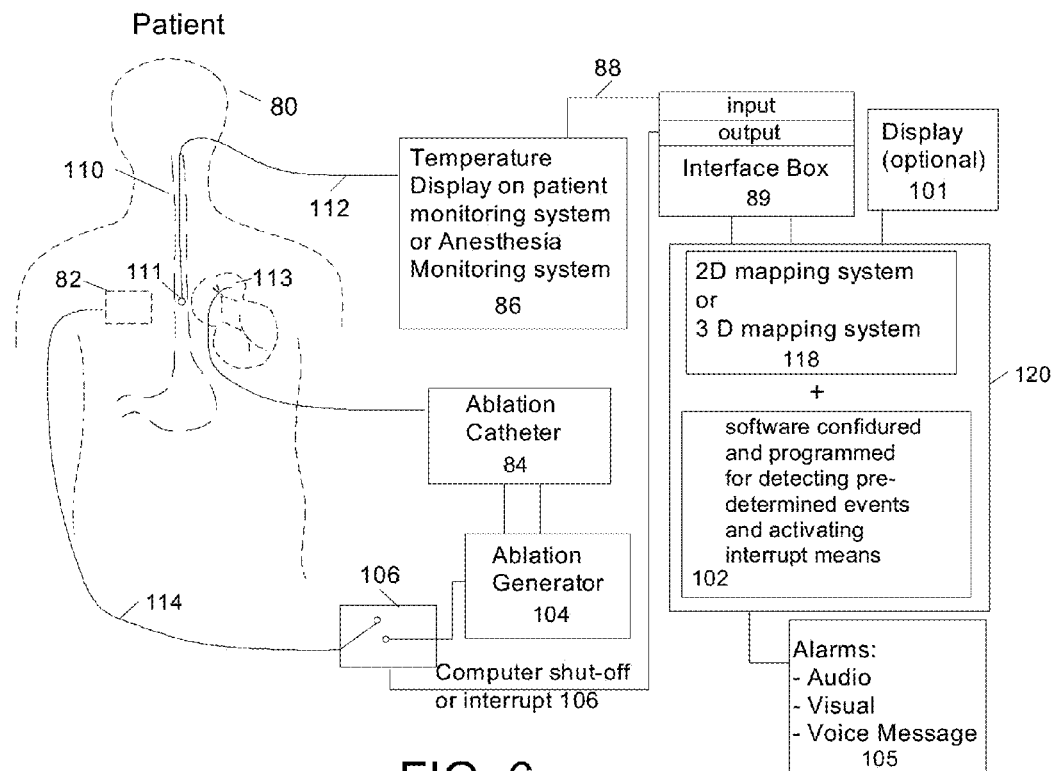
FIG. 6 depicts a general setup of the concept where the esophageal signals from the patient are split and slaved into a 2-D or 3-D mapping system, and where the logic for alarms and automatic interrupt is incorporated within the 2-D or 3-D mapping system.

In another embodiment, the software algorithms for esophageal temperature monitoring and out-of-range limit alarms may be incorporated into a 2-D cardiac electrophysiology recording or monitoring system, or a 3-D cardiac mapping system. This is shown in conjunction with FIG. 6. Examples of 2-D cardiac electrophysiology systems include, the CardioLab™ system of GE Healthcare, CR Bard's recording system, and electrophysiology recording system marketed by St. Jude Medical. Examples of 3-D mapping systems include Biosense Webster's Carto® mapping system, St Jude's Navix™ mapping system, and a mapping system by Boston Scientific's Rhythmia Medical's mapping system. In this embodiment, as shown in conjunction with FIG. 6, the esophageal probe 112 signal is either slaved 88 into the electrophysiology monitoring or recording system 118 via an interface box 89 or directly connected to cardiac recording or mapping system (not shown). In this embodiment, the software of the monitoring system or mapping system 120 is configured and programmed such that the algorithms for detection of out of range limits for esophageal temperature are incorporated. As shown in FIG. 6, the system 120 also controls the automatic shut-off or interrupt and the audio, visual and voice messages 105.

Figure 7:
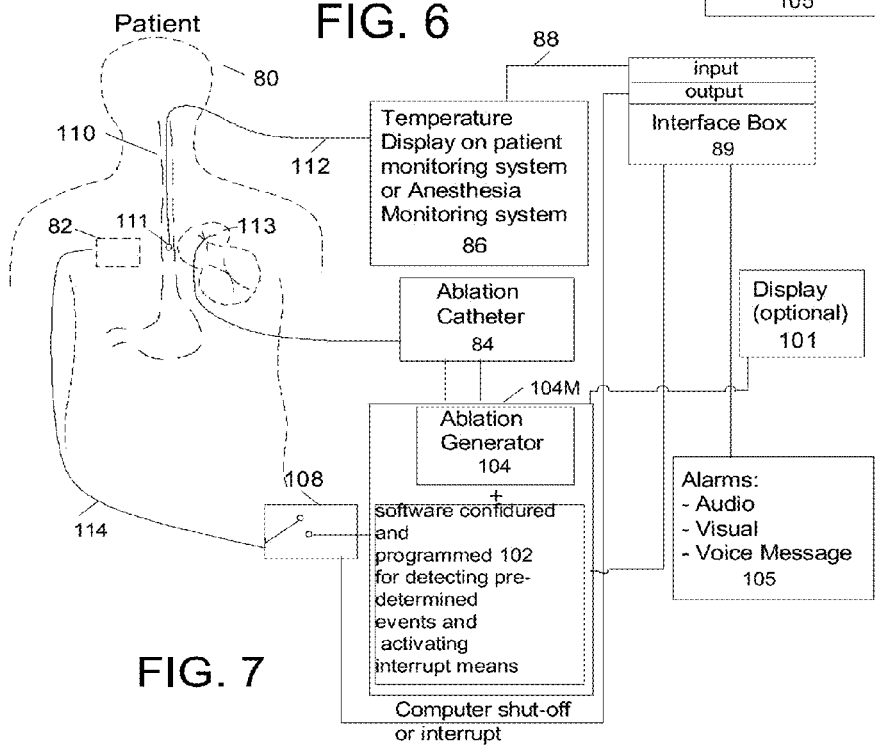
FIG. 7 depicts a general setup of the concept where the esophageal signals from the patient are split and slaved into the ablation generator, and the logic for alarms and automatic interrupt is incorporated into the ablation generator system.

In another embodiment, the algorithms for temperature monitoring and out of range limit alarms may be incorporated in the ablation generator system 104M. This is shown in conjunction with FIG. 7. In this embodiment, the standard ablation generator 104 is modified such that the controller in the modified ablation generator 104M comprises software which is configured and programmed to handle the algorithms for temperature monitoring from the esophagus 110, and implement out of range limit alarms 105 and computer shut-off or interrupt 106. As shown in FIG. 7, in this embodiment, the temperature probe signals are slaved and are connected to the modified ablation generator 104M via an interface box 89. The logic functions of alarms 105 and interrupt 106 are now configured and programmed 102 within the ablation generator 104M.

Figure 3:
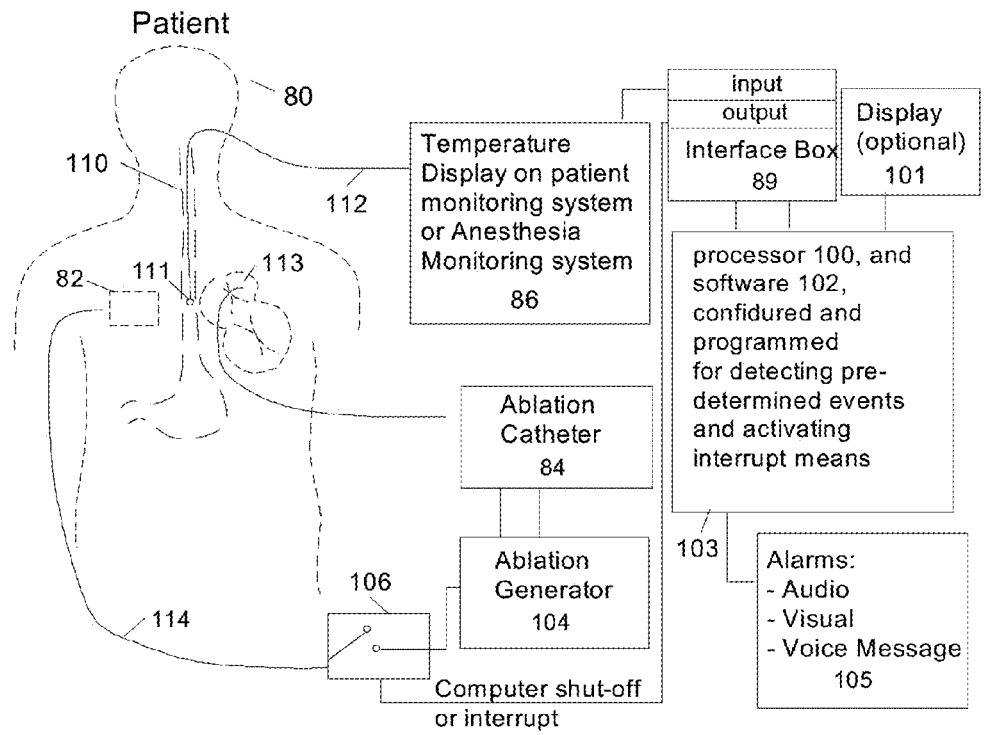
FIG. 3 depicts a general setup of the concept where the esophageal signals from the patient are brought into another computer from the patient monitoring system.
Figure 4:
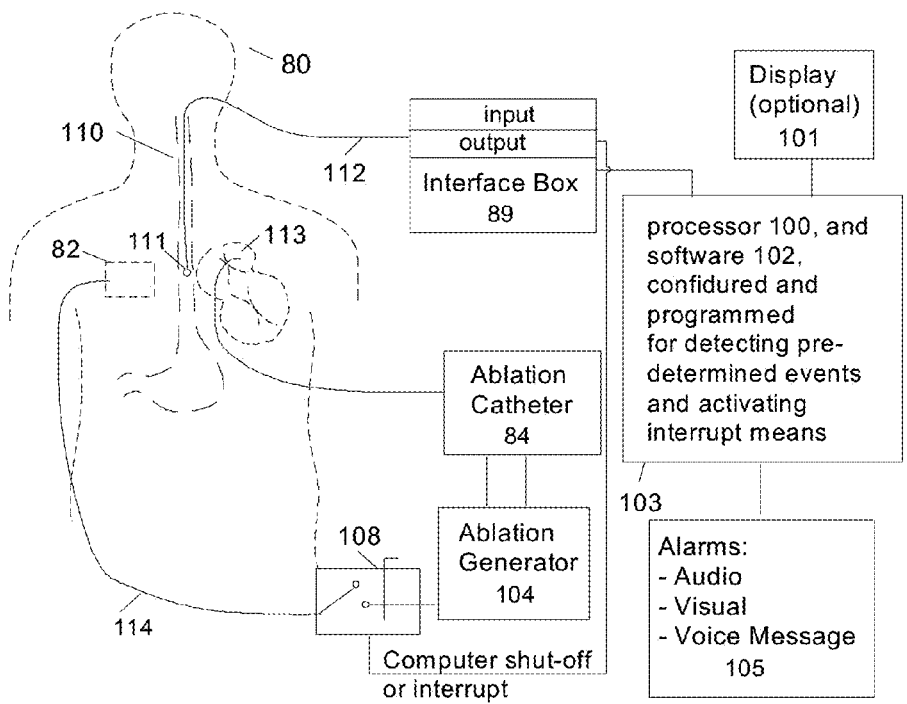
FIG. 4 depicts a general setup of the concept where the esophageal signals are brought into a computer for monitoring without using the patient monitoring system.
Figure 5:
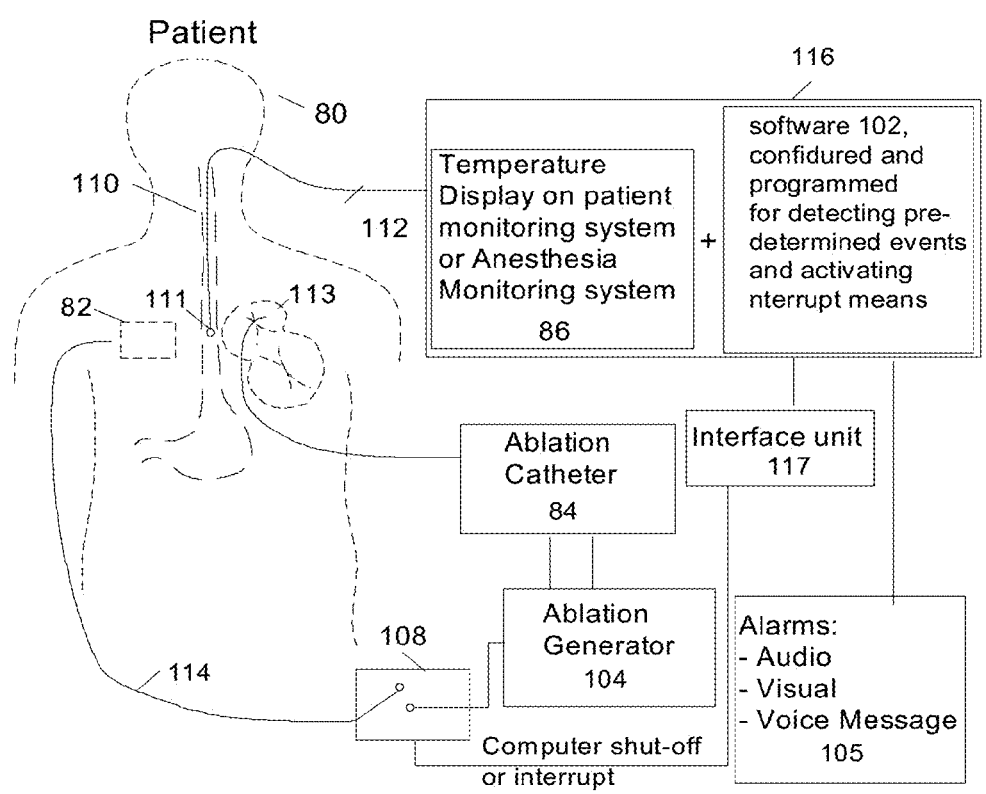
FIG. 5 depicts a general setup of the concept where the esophageal signals are monitored by the patient monitoring system and the logic for alarms and automatic interrupt is incorporated into the patient monitoring system.

As was shown in FIG. 3, the computer 103 has a display 101. This is shown in conjunction with FIGS. 8A & 8B as display 126. There is both a digital display 128, and an analog display 130. At the beginning of the atrial fibrillation ablation procedure the baseline temperature 142 is updated. Following that, the computer program tracks the temperature relative to the baseline 142. First alarm (Alarm 1) 132 can be turned ON or OFF. In one example, there is a simple sliding scale to program the threshold level for the first alarm provided it is turned ON. Similarly, a second alarm (Alarm 2) 134 (shown in FIG. 8B) can be turned ON or OFF. If Alarm 2 is turned ON, the threshold level for Alarm 2 is greater than Alarm 1, and can be adjusted simply by the sliding scale in this example.

In addition to the first and second alarms, there is an Auto shut-off feature 136 also. The Auto shut-off 136 feature may be used in conjunction with Alarm 1 and Alarm 2, or the two alarms may be turned OFF and Auto shut-off 136 may used alone by itself. The threshold criteria for the Auto shut-off 136 can be entered in a similar manner by adjusting the sliding scale. There is a Reset button 138 for bringing all the values to default values, and adjusting the parameters again. As shown in the figure, there is a Bypass button 140, to take the computer and system out of the loop from the ablation procedure, if an operator so desires for any reason.

Figure 8B:
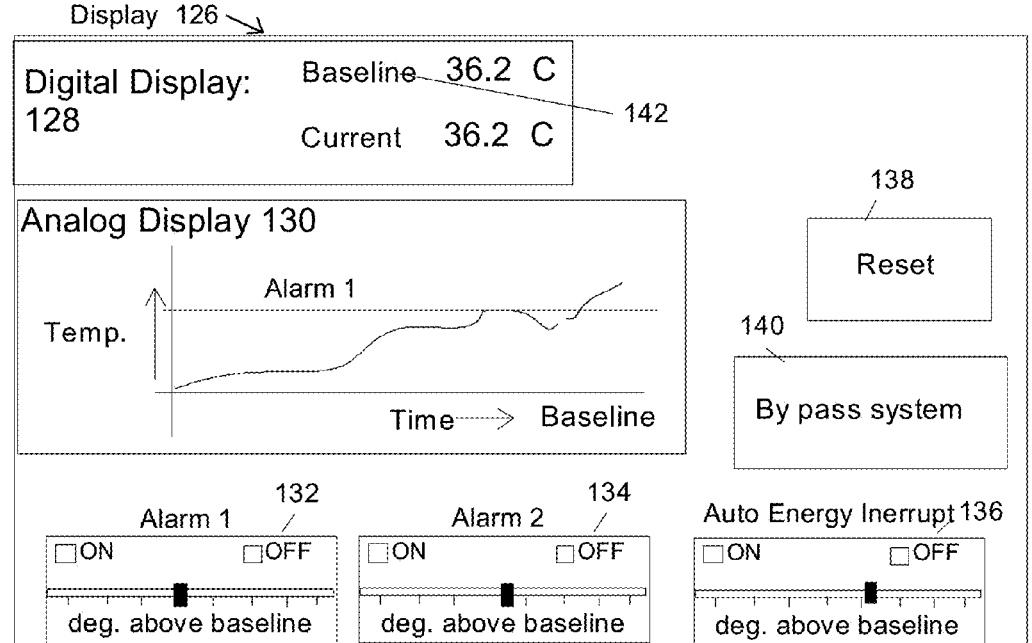
FIG. 8B shows an example of graphical display and graphical interface of the concept with adjustable time delay.

FIG. 8B shows an example of graphical display and graphical interface of the concept with two levels of alarms, alarm 1 and alarm 2.

It will be clear to one skilled in the art that various different software's may be used in implementing this concept and methodology. Program code can be written using one of several commercially available software packages. The software that can be used for this purpose is LAB WINDOWS/CVI, LABVIEW (National Instruments Corp.), C+, Microsoft Visual C++, Dot Net framework, MATLAB, and Microsoft Visual Basic, among others. Use of these or other comparable languages for this purpose that are available now or developed in the future, is considered within the scope of the disclosure. Testing of applicant's prototype has been performed using Microsoft visual C++, LabView and MATLAB.

Figure 9A:
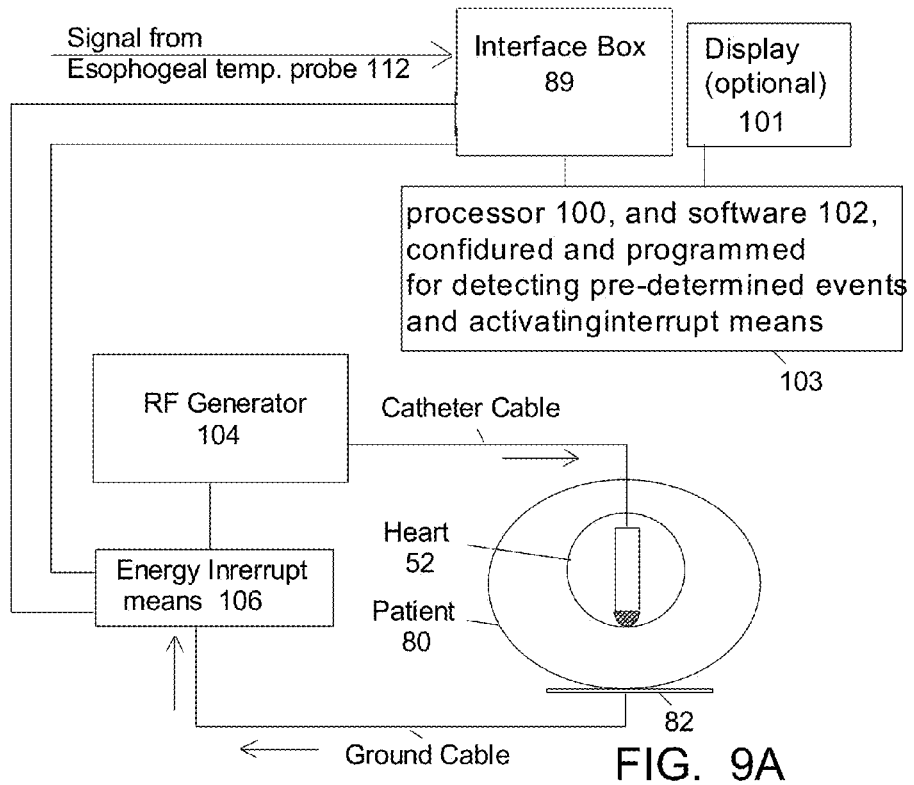
FIG. 9A depicts schematically the overall concept of the system, with the circuit interrupt in the ground loop portion of the circuit.

FIG. 9A summarizes schematically the ablation circuit and its relation to esophageal temperature monitoring circuit and automatic interrupt of ablation energy delivery. Signal from the esophageal probe 112 is brought into the computer 103 via the interface box 89. Computer 103 comprises software configured and programmed with algorithms 102 capable of detecting pre-determined events and computer based interrupt of energy delivery. When a pre-determined threshold criteria is met, the control switch will interrupt the ablation energy delivery to the circuit. As shown in the figure, energy interrupt means 106 is placed in the return path of the ablation circuit. Alternatively, the energy interrupt means 106 can also be placed on the catheter side of the circuit.

In one aspect of the disclosure, instead of just indicating alarms and interrupting energy delivery, active attempt is made to cool the esophagus. In one aspect active cooling of the esophagus is performed by itself. In another aspect of the disclosure active cooling of the esophagus is performed in conjunction with various alarm(s) and automatic interrupt.

Figure 9B:
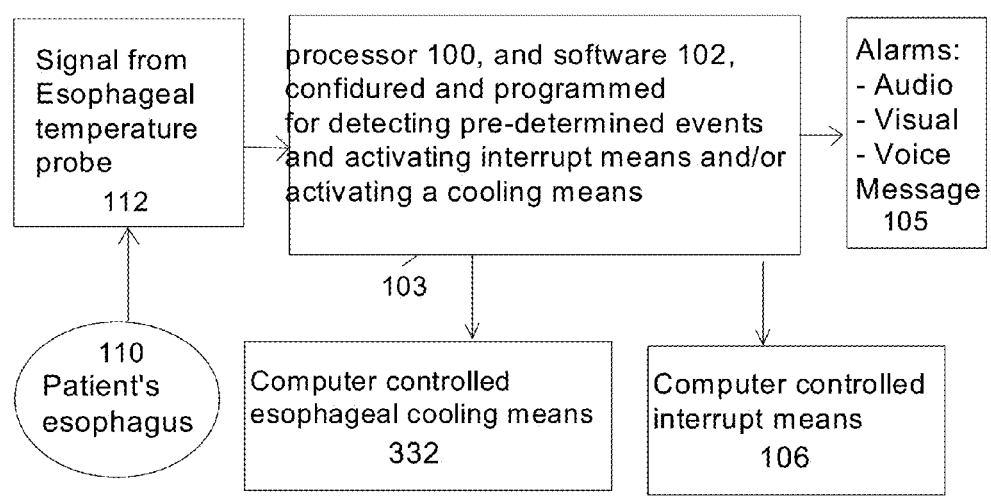
FIG. 9B depicts in block diagram the concept with computer controlled esophageal cooling means.

Shown in conjunction with FIG. 9B, as before a temperature probe 112 is inserted into the esophagus 110. Additionally, apparatus for cooling the esophagus is also inserted. In one aspect it is a saline balloon which is flushed with cool saline from an external saline bag. For the practice of this disclosure any other means of cooling the esophagus 100 may be used. As shown in FIG. 9B the esophageal cooling apparatus is controlled by a controller based on pre-programmed algorithms.

Saline or salt water typically freezes at 39° F. Therefore, without limitation in one embodiment temperatures in the range of approximately 40° F. and 55° F. may be used. Other temperatures may also be used. The decision of the temperatures will generally be determined by the lab.

Figure 9C:
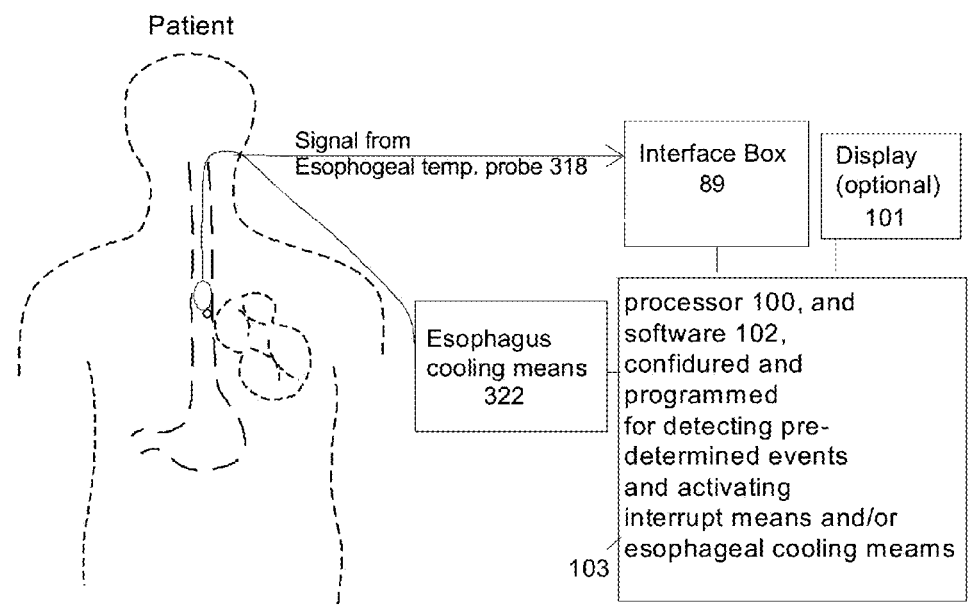
FIG. 9C depicts the embodiment where the cooling means comprises a saline bag filled with cold saline that can be used for cooling the esophagus.
Figure 9D:
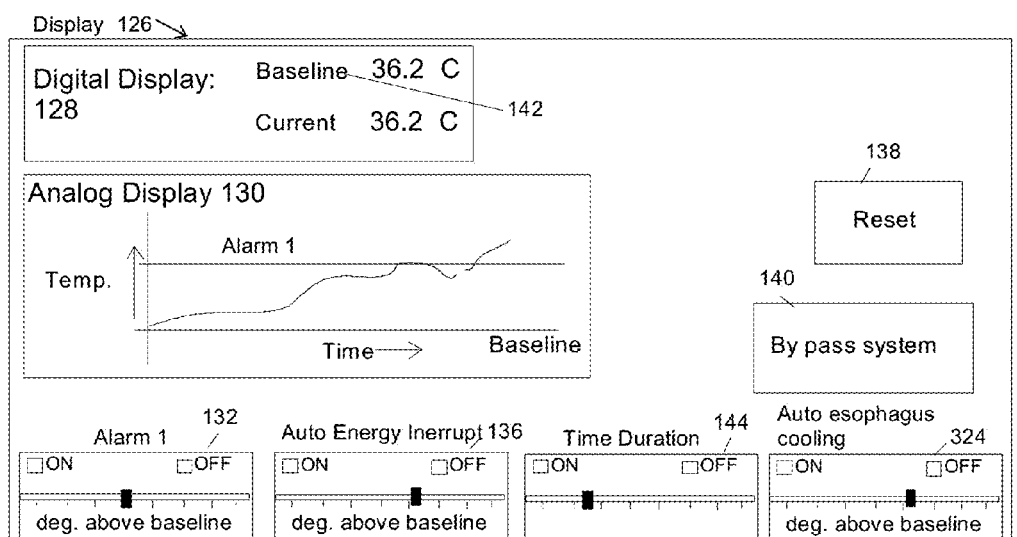
FIG. 9D shows an example of graphical display and graphical interface of the concept with Auto esophagus cooling.

Shown in FIG. 9C is one embodiment of this invention. As shown in the figure, in this embodiment a modified esophageal temperature probe 318 includes a balloon 310 which can be filled with cold saline to cool the temperature of the esophagus 110. The cold saline is supplied from a saline bag 314 which may be placed on a stand similar to a saline drip, which is common in procedure rooms. As also shown in the figure, the flow of cold saline is controlled by controller 103, which receives its input from the temperature probe based on the programmed values. It may also be controlled by a separate controller. Therefore in one embodiment as the esophageal temperature reaches a pre-determined level, an alarm may be activated. Additionally, as the esophageal temperature reaches the next pre-determined level, cool saline may be deposited in a balloon or pouch 310 which is located adjacent to the temperature probe 111 inside the esophagus. Further, if the temperature increases further to a next pre-determined level, the ablation energy may be interrupted. All of the above events will be activated according to the program setting as entered by the operator. FIG. 9E shows the display for this embodiment.

It will be clear to one skilled in the art that pre-determined event(s) can trigger alarm(s), an energy interrupt, or esophageal cooling means or any combination of these.

Figure 10:
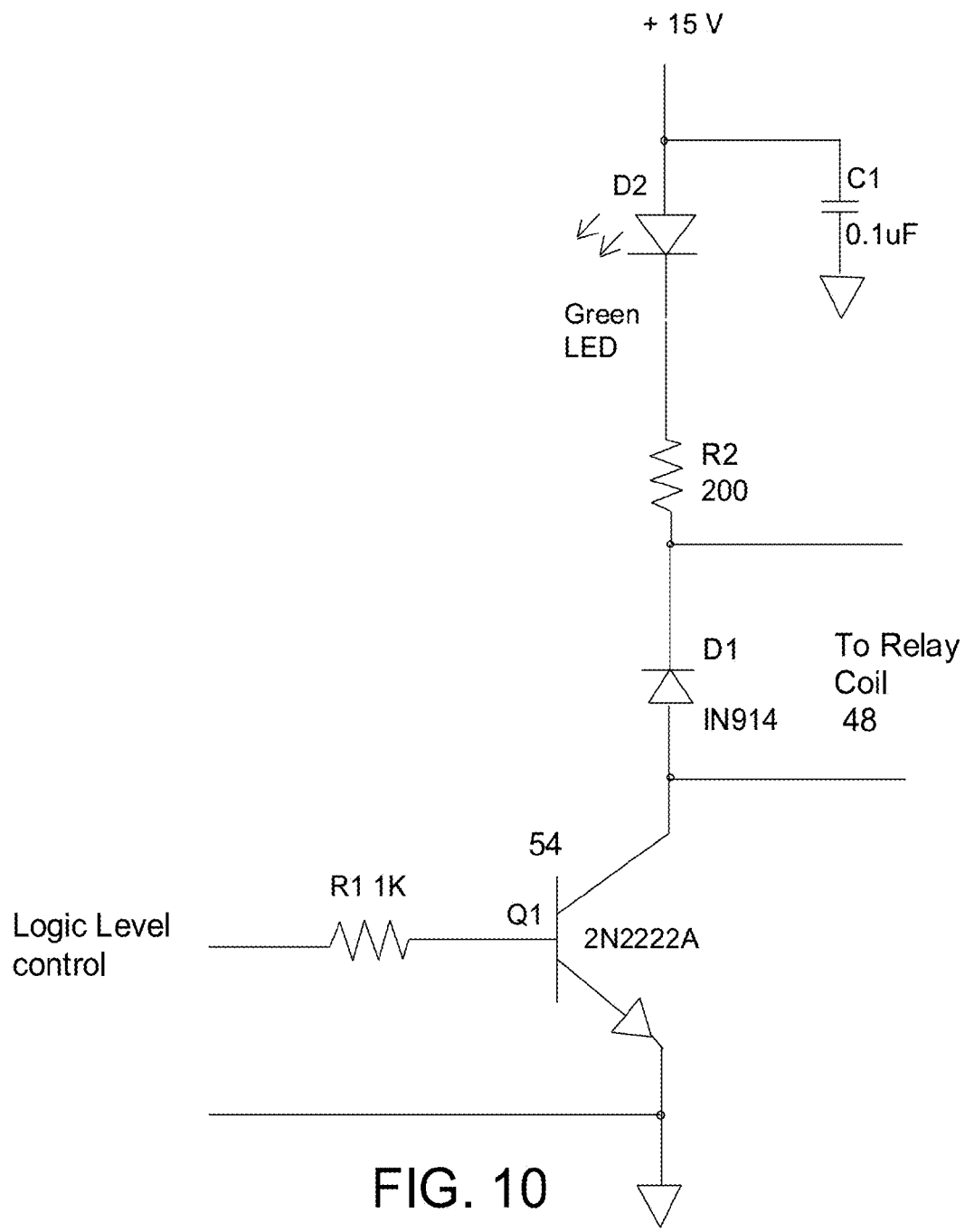
FIG. 10 is an electrical schematic for the control of the relay switch.
Figure 11:
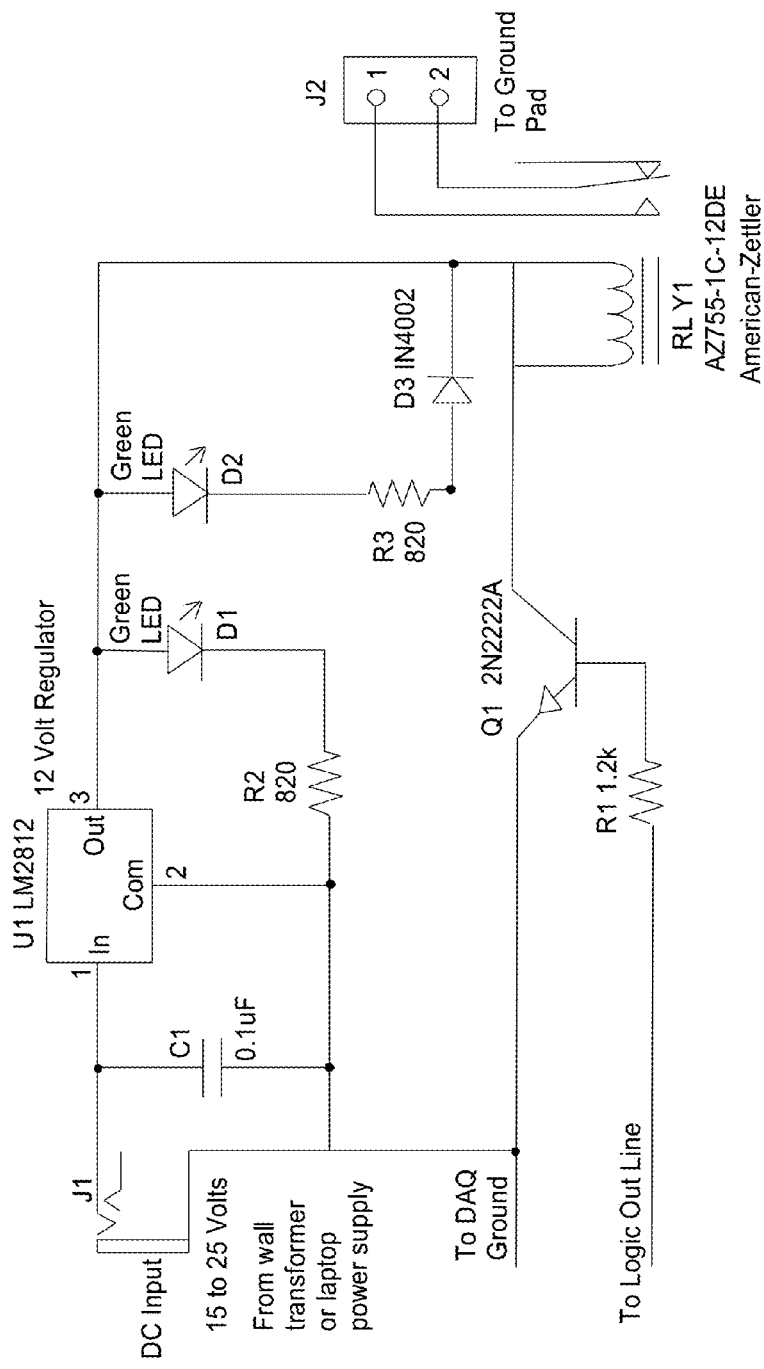
FIG. 11 shows one example of the relay switch.

The circuitry for one example of the control switch is shown in conjunction with FIGS. 10 and 11. FIG. 10 shows a simplified circuit to drive a relay coil 48, which interrupts the ground loop side of the ablation circuit. As shown in the figure, when the logic level control 54 goes high, there is current flow at the base of transistor Q1 (54), and transistor Q1 conducts, energizing the Relay coil 48. The logic level control 54 is high only when certain pre-determined conditions are met. The pre-determined conditions are derived by analysis of signals and are based on safety conditions for esophageal temperature change.

Most ablation generators on the market have maximum impedance cut-off and delta impedance cut-off features. In this feature, when the impedance increases over the adjusted maximum cut-off value or is infinite (e.g. if the connection to the catheter is broken) the ablation generator will switch off automatically and an error message "Imped. too high" will be displayed in one example.

Using this feature of the ablation generator, shown in FIG. 11 is one implementation for practicing this method. In this embodiment, Logic High energizes the relay, thereby shutting off the ablation generator.

As shown in conjunction with FIG. 11, a relay switch circuitry is connected in the ground patch electrode 23. In this configuration, a transistor Q1 54 performs the switching. When the Logic Out Line from the DAQ goes "high", the relay is energized. Power to the circuit may be supplied by a wall transformer or laptop power supply. The logic out line from DAQ is controlled by the software.

Figure 12:
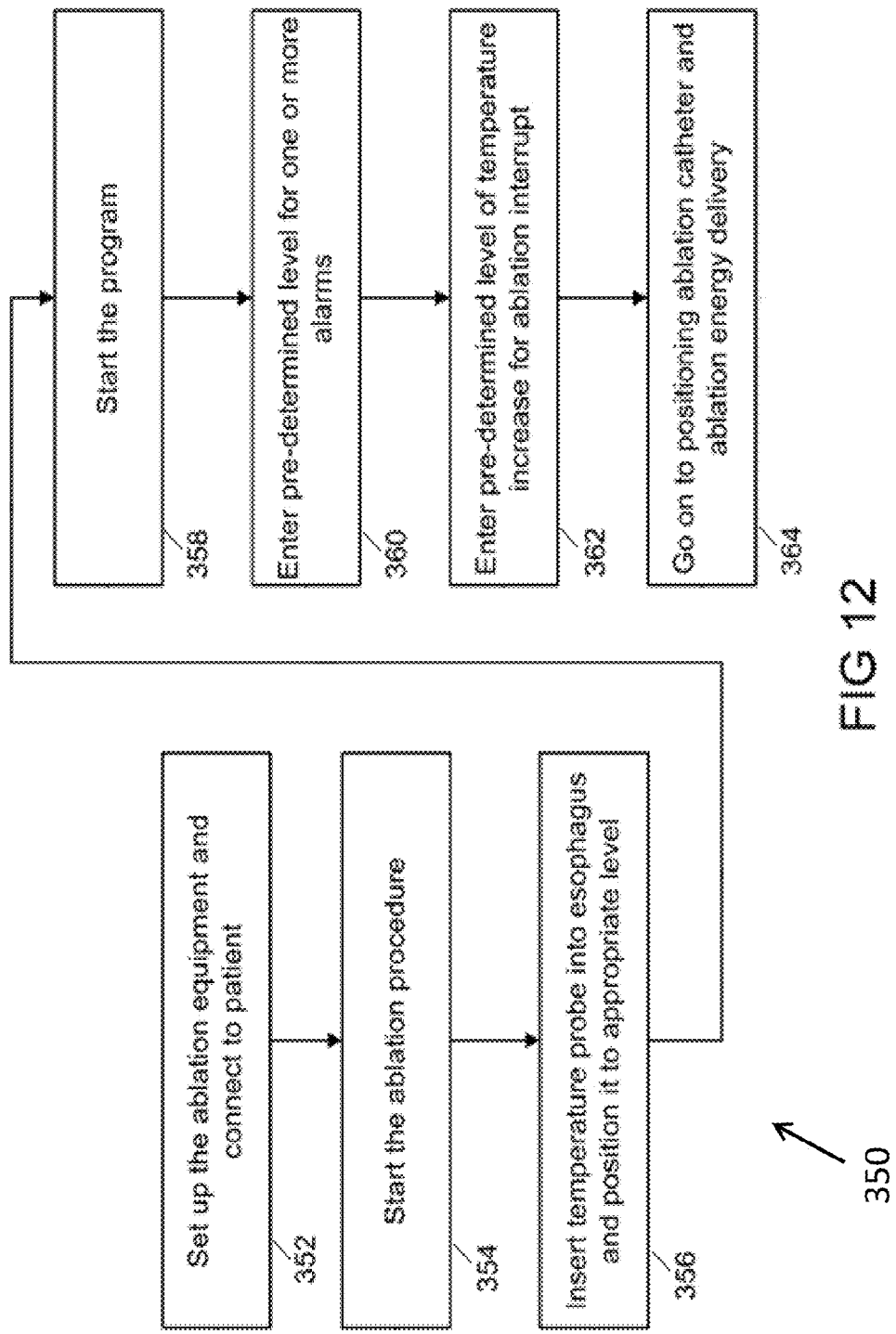
FIG. 12 is an overall flow diagram of the method of the concept for temperature monitoring and ablation interrupt.

FIG. 12 depicts a flowchart of a typical procedure. The flowchart 350 begins at block 352 where the equipment is set up and connected to the patient. The procedure begins as shown in block 354. The temperature probe is positioned in the esophagus, block 356 and the program is started block 360. The operator enters pre-determined levels for one or more alarms 360 as determined by the physician. The operator also enters per-determined level of temperature increase for ablation interrupt 362, also as determined by the physician. The ablation catheter is then positioned and ablation energy is started as shown in step 364.

In one aspect, a temperature probe comprising multiple thermisters is utilized. Any number of thermistors on an esophageal probe may be utilized. An advantage of multiple thermistors is that it covers a relatively larger area of the esophagus, as opposed to a small segment with just one thermistor. Advantageously, the temperature probe with multiple thermistors does not have to be moved, or re-positioned less often once it is initially placed in the esophagus. Further, it will even protect patients with large left atrial sizes. The overall concept utilizing esophageal probe with multiple thermistor (or thermocouples) is shown in conjunction with FIG. 13. In this disclosure, even though examples are shown with 10 and 12 thermistor probes (sensors) on the esophageal probe, it will be clear to one skilled in the art, that with slight modification of the hardware and software, any number of thermistors (or thermocouples) may be utilized.

Figure 13:
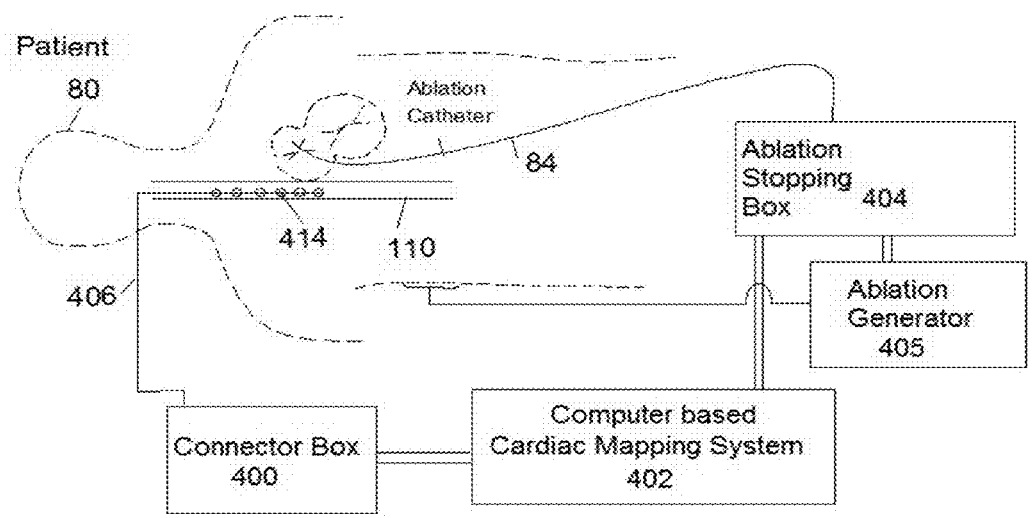
FIG. 13 is a block diagram of overall concept showing monitoring of temperature from an esophageal probe and processing temperature information in a cardiac mapping system.
Figure 14:
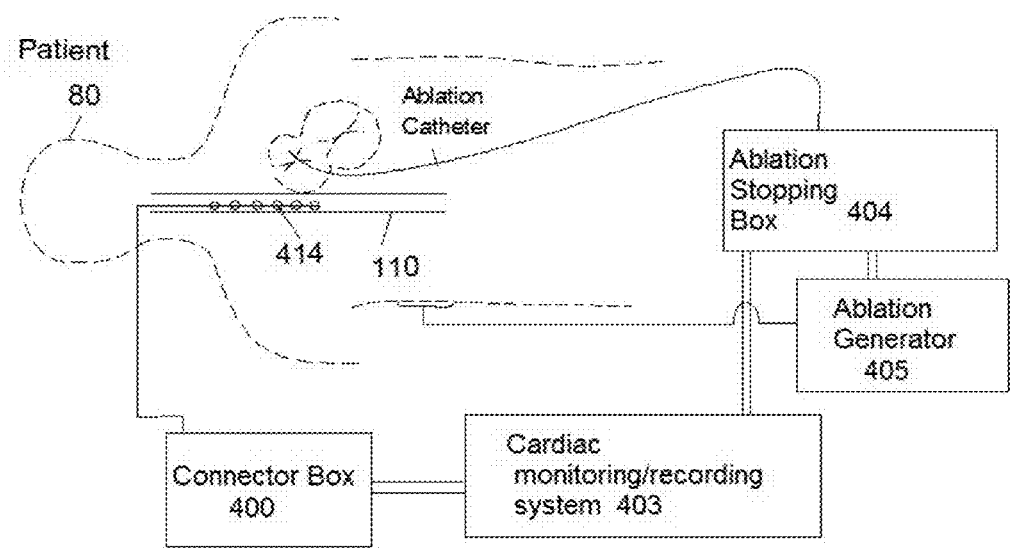
FIG. 14 is a block diagram of overall concept showing monitoring of temperature from an esophageal probe and processing temperature information in a cardiac monitor/recording system.

As shown in FIG. 13, patient 80 is inserted with a multiple thermistor esophageal probe 414. The temperature information from the esophageal probe 414 is brought into a cardiac mapping system 402 (or cardiac monitoring/recording system 403, shown in FIG. 14) via an interface connector box 400.

The cardiac mapping system 402, may also be connected to an ablation stopping box 404 (or energy interrupt box 404). The ablation interrupt box 404 is connected in-between the ablation catheter 84 and the ablation generator 405. Based on a command signal from the cardiac mapping system 402, the ablation stopping box 404, which is between the ablation catheter 84 and the ablation generator 405, interrupts the energy delivery of the ablation catheter 84 during the procedure, based on reaching the criteria of pre-determined conditions set by the operator or the physician, before the ablation starts.

Figure 15:
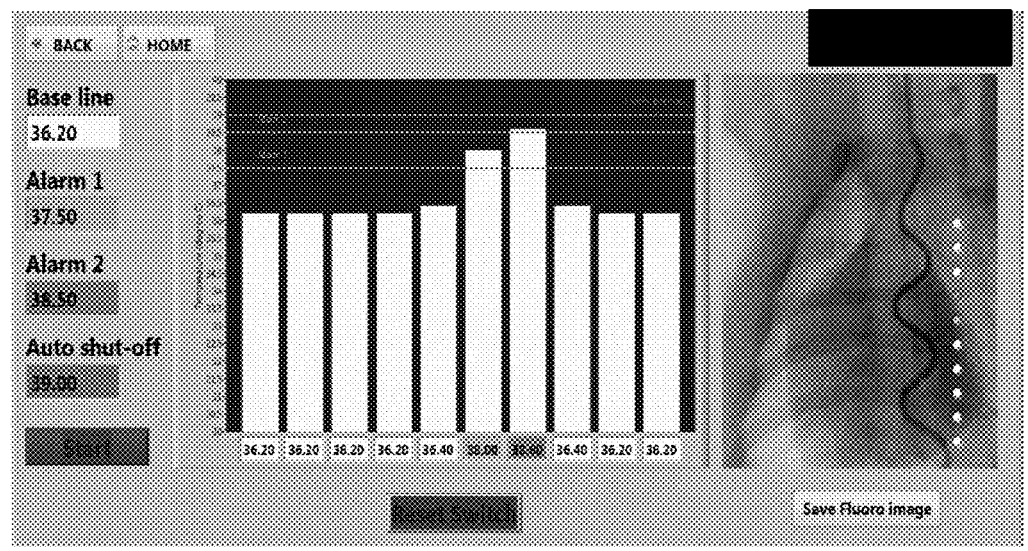
FIG. 15 is a picture of graphical unit interface (GUI) of the cardiac mapping system showing temperature readings from multiple sensors, as well as placement of multiple of the multiple sensors.

The graphical unit interphase (GUI) of applicant's cardiac mapping system of one embodiment is shown in FIG. 15. This esophageal temperature monitoring functionality and GUI is incorporated and integrated with other functions of the cardiac mapping system (or monitoring/recording system) such as "electro-antomical mapping".

The details of esophageal probe 414, connector box 400, cardiac mapping system 402, and ablation stopping box 404 are described below.

Figure 16:
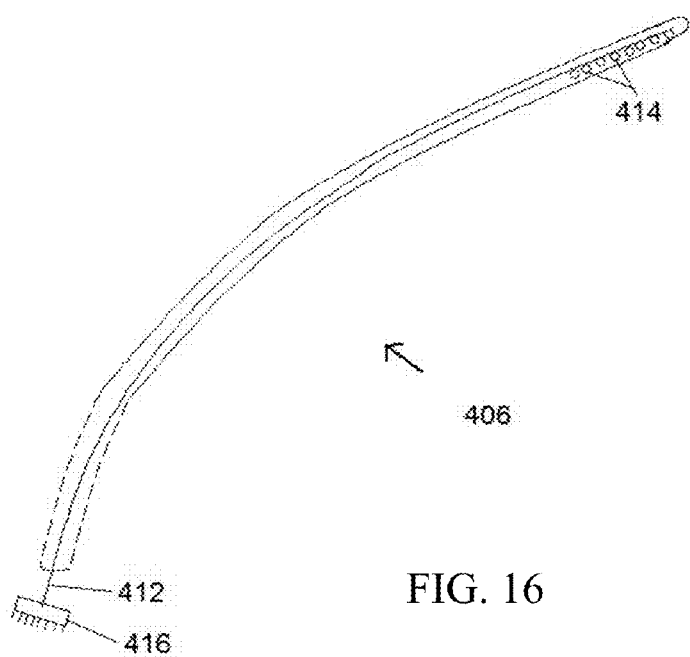
FIG. 16 is one embodiment of an esophageal probe with multiple sensors (thermistors), which is straight in shape.

In one aspect of the disclosure, any esophageal temperature probe may be used. In one embodiment, the esophageal probe may have one thermistor or thermocouple (sensor). In another embodiment, the esophageal probe may have more than one thermistors (or thermocouples). These may comprise any number of thermistors (or thermocouples). Shown in FIG. 16 is an exemplary esophageal probe 406 that may be used. This esophageal probe has a number of thermistors 414. Various thermistors have conductor wires which travel through the body of the lumen 412, and are connected to terminal connector(s) 416. The terminal connector 416 (on the proximal end) of the esophageal probe 406 connects to a connector box 400 (FIGS. 13 and 14) to get sensor information into a cardiac mapping system 402 (or cardiac monitoring/recording system 403).

In one aspect of the disclosure, the esophageal probe 406a, 406b may have a pre-built memory or pre-defined shape. This pre-defined shape may be in the form of "S" shape or any other pre-built shape. Two examples (without limitation) of these shapes are shown in conjunction with FIG. 17A and FIG. 17B. The only thing different in this embodiment is the pre-defined (or pre-built) shape. The body or shaft of the esophageal probe 406, 406a, 406b may comprise a lumen or space for inserting a straight stylet. The straight stylet is used for straightening the esophageal probe for insertion and generally withdrawn after the placement of the esophageal probe in the esophagus 110. Same method of straightening the probe may be used to take the esophagus probe out.

In one embodiment, the esophageal probe 406 comprises an inflatable balloon, and the thermistor sensors are embedded in, or over the balloon. Examples of esophageal probe with inflatable balloon are shown in conjunction with FIGS. 18A and 18B. In the embodiment shown in FIG. 18A, the thermistors are encased in a covering of a sheath. In FIG. 18B, the thermistors are on top of the balloon and are exposed, giving the probe greater sensitivity and exposure. As previously stated, there may be any number of thermistors. The objective of the thermistors being on an inflatable balloon is that they will be in closer contact to the esophagus 110 wall for monitoring esophageal temperature.

Figure 19:
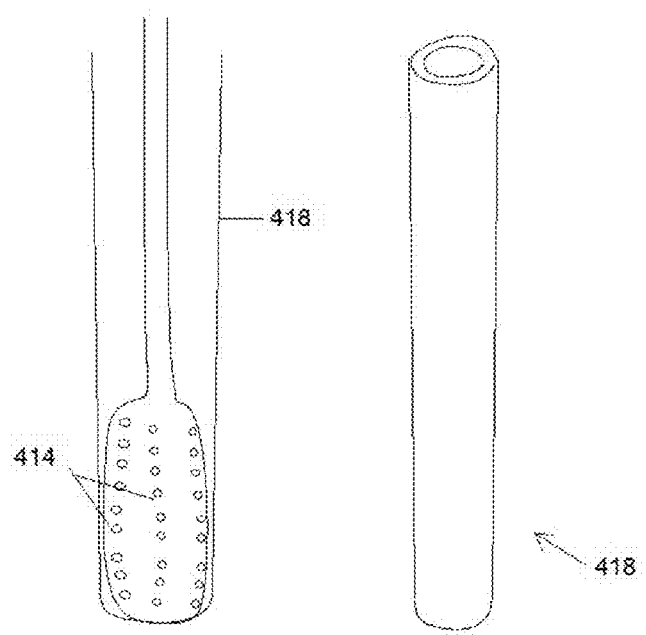
FIG. 19 depicts an esophageal probe with multiple sensors which is encased in a sheath or membrane.

The esophageal probe including the inflatable balloon comprising the thermistors may be enclosed in a sheath or membrane. This is shown in FIG. 19 where a sheath 418 is encased over the esophageal probe.

The connector box 400 (FIG. 13) houses the circuitry and is the interface between the esophageal probe 406 and the cardiac mapping system 402.

Figure 20:
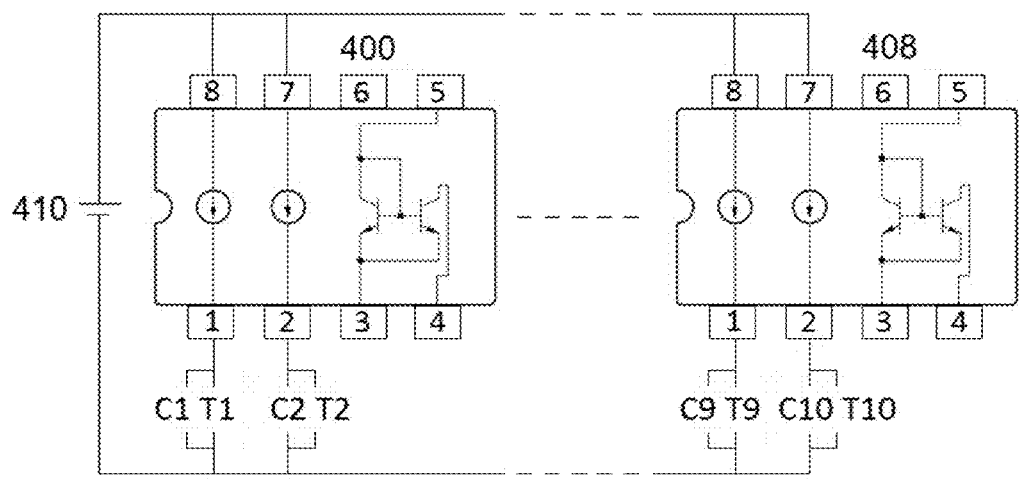
FIG. 20 shows an electrical diagram of circuitry for temperature measurements from ten thermistors.

Details of the circuitry are shown in conjunction with FIG. 20. To measure the temperature, ten of 2-wire thermistors are used (T1 to T10). Generally the thermistors are sensitive semiconductors in that their resistance varies with the temperature according to a linearized approximation. Also, thermistors generally have a fast response rate and their nominal resistance makes them the best option for precise measurements in lower-temperature applications like tissue temperatures while ablating (32 to 40° C.) for atrial fibrillation ablations.

Shown in conjunction with FIG. 20, to take temperature measurements, thermistors are supplied with current excitation source and the produced voltage across them (based on the ohms' law) is scaled into temperature by using the Steinhart-Hart thermistor third-order approximation as follow:

$$\frac{1}{T} = A + BR^{-1} + CR^{-3}$$

where T is the temperature in Kelvin, R is the thermistor's measured resistance, and A, B, and C are constants provided by the thermistor manufacturer.

Also, as shown in FIG. 20 in one embodiment for implementation of the excitation, five Texas Instruments Integrated Circuits called "REF200" (400-408) can be used. This 8-pin IC is a dual current source/current sink with three sections on a single chip. The three sections are two 100 μA current sources and a current mirror. Sections are dielectrically isolated which makes them completely independent. Since the current sources are two terminal devices, they can be used equally well as current sinks. The performance of each section is individually measured and laser-trimmed to achieve high accuracy at low cost. Pins 1 and 8 form the first 100 μA constant current source and pins 2 and 7 the second one. The current flows from pin 8 to 1 and from pin 7 to 2. Pins 3, 4 and 5 are also used for the current mirror. The sections can be pin-strapped for currents of 50 mA, 100 μA, 200 μA, 300 μA or 400 μA. External circuitry can be used to obtain virtually any current. Pin 6 is connected to a defined circuit potential to assure rated DC performance. The preferred connection is to the most negative constant potential in the system. In most analog systems this would be −VS. For best AC performance, pin 6 should be left open and unused sections unconnected. The IC can be powered from −6 V to +40 V (412).

Figure 21:
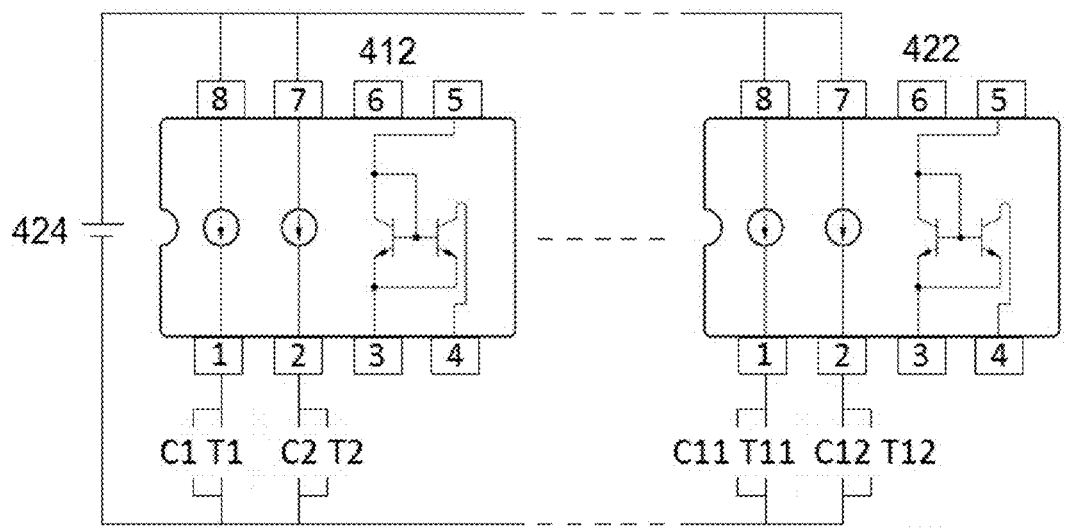
FIG. 21 shows an electrical diagram of circuitry for temperature measurements from twelve thermistors.

The voltages produced across the thermistors are acquired by an FPGA for reliable and continues real-time measurements (C1 to C12) and the voltage to temperature conversion is done in real-time by the system software. FIG. 21 shows an example of one implementation where six ICs are used for 12 thermisters on the esophageal probe.

Cardiac Mapping Systems

Cardiac mapping systems are well known in the art and are generally used during cardiac ablation procedure in atrial fibrillation procedures where temperature monitoring is needed.

The role of these mapping systems has been to keep a log of and make manageable and interpretable the vast amount of information obtained during an electrophysiology study. These systems have made possible the extensive intracardiac mapping that can now be performed and applied during electrophysiologic procedures. This enhanced mapping capability has been especially useful in the treatment of complex arrhythmias that require extensive ablation in the cardiac chambers, e.g., atrial fibrillation and ventricular arrhythmias.

The two of the commonly used mapping systems are CARTO (Biosense Webster) and NavX EnSite (St. Jude Medical, Inc.). CARTO uses a low-level magnetic field measured by a catheter location sensor, whereas NavX registers electrode impedance sensor in relation to skin patches that apply a low-level electrical current.

Electromagnetic Based Mapping System

Systems such as CARTO (Biosense Webster, Diamond Bar, Calif.) use the electromagnetic position of the catheter tip relative to an electromagnetic locator pad which is placed below the patient, and a reference catheter at a fixed external (usually posterior) location. The CARTO system provides electroanatomic mapping based upon the premise that an electrical current is generated when a metallic coil is placed in a magnetic field. The magnitude of the current depends on the strength of the magnetic field and the orientation of the coil in the field. The CARTO system consists of,

- a magnetic field emitter mounted under the patient; the external magnetic field emitter has 3 coils that generate ultra-low-intensity magnetic fields (between 5×10−6 and 5×10−5 T) that code the surrounding space with spatial information sensed by the field sensor at the tip of the mapping catheter
- a location sensor inside the mapping and ablation catheter tips, and
- a data processing unit and graphical display unit to generate and display the 3D model of the cardiac chamber of interest.

Data on the amplitude, frequency, and phase of the magnetic field are gathered and analyzed by the processing unit and displayed on the display unit. The CARTO mapping system uses a triangulation algorithm in which a sensor in the catheter tip allows the determination of its distance from each coil. In addition to the x, y, and z coordinates of the catheter tip, the CARTO mapping system can determine three orientation determinants—roll, pitch, and yaw. The position and orientation of the catheter tip can be seen on the screen and monitored in real-time as it moves within the electroanatomic model of the chamber being mapped.

Since the CARTO mapping system is not an imaging technique, fluoroscopy is initially used to establish orientation by using generally known anatomic locations in the heart as references for the later creation of the model of the mapped chamber. An electromagnetic anatomical reference patch is placed on the back of the patient and is used to track the mapping and ablation catheter. For activation mapping, an electrical reference such as an ECG signal or an intracardiac recording is used. For intracardiac recordings, coronary sinus recordings are often selected because they are usually stable. For activation, points taken by the catheter are color-coded red, orange, yellow, green, blue and purple for progressively-delayed activation areas. Similarly, the voltage map is also color-coded and superimposed on the anatomic model. Using these techniques, both the mechanism of the arrhythmia and the 3D anatomy can be created. However, creation of an electroanatomic map may be a lengthy process involving the tagging of many points, depending upon the spatial details needed to analyze a given arrhythmia. Lack of accurate ECG and respiration gating and non-real-time data are other limitations of this technique. Furthermore, the catheters used are very expensive and fluoroscopy is always used as a backup to identify the location of catheters.

Electrical Impedance Electroanatomic Mapping

The concept underlying the use of electrical impedance to calculate a spatial locations is based on the following: A very low-voltage alternating current of a particular localization frequency is applied across a patient's body using two skin electrodes confers a relatively linear voltage gradient across the tissues in the axis of the electrodes. The voltage can be detected by a sensing electrode and can then be converted to the axial location of the sensor. Three such orthogonal electric currents applied separately and detected by a sensor can thus be used to triangulate the 3-dimensional (3D) location of the sensor.

Mapping using this concept requires fulfillment of the following 4 conditions: 1) 3 orthogonal currents with the heart at the center need to be used to allow triangulation in 3-dimensional space; 2) the externally applied electric current should be easily detectable but benign to the patient and not interfere with the recorded electrograms; 3) the voltage gradient need to be calibrated to interpret recorded voltages for localization; and 4) spatial variations associated with the cardiac and respiratory cycles need to be accounted for. Thus stabilization of the whole localization apparatus throughout the mapping and ablation procedure is important to limit inaccuracies.

The EnSite NavX (St. Jude Medical, Inc. St. Paul, Minn.) was first described for electroanatomic mapping and navigation in atrial flutter ablation in 2004. A low electric current at 5.68 kHz is multiplexed with each of these pairs of electrodes to create the navigational electric field across the heart. A fixed intracardiac catheter (e.g., in the coronary sinus) or a surface electrode serves as the reference. The electrode position is averaged over 1 to 2 cardiac cycles to reduce cyclic cardiac variation. However, because of the long excursion of the respiratory cycle, eliminating respiratory variations by averaging becomes impossible without compromising the real-time localization and display.

Fluoroscopy Based Mapping System

In the method and system of fluoroscopy based mapping system, a cardiac mapping system has been disclosed where existing cardiac image or multiple images are utilized, and electrical parameter(s) information is/are superimposed on them to provide an "electro-anatomical" map. The existing cardiac image(s) may be a fluoroscope image or combined images such as a 3D computed tomography (CT) image overlaid or registered on a fluoroscope image, or other images as described later. This may also be referred to as a "sensor-less" cardiac mapping system, as the prior art systems comprise sensors that are impedance based or electromagnetic based, and the current disclosure describes a method and system that can perform electro-anatomical cardiac mapping without the impedance or electromagnetic based sensors.

Figure 22:
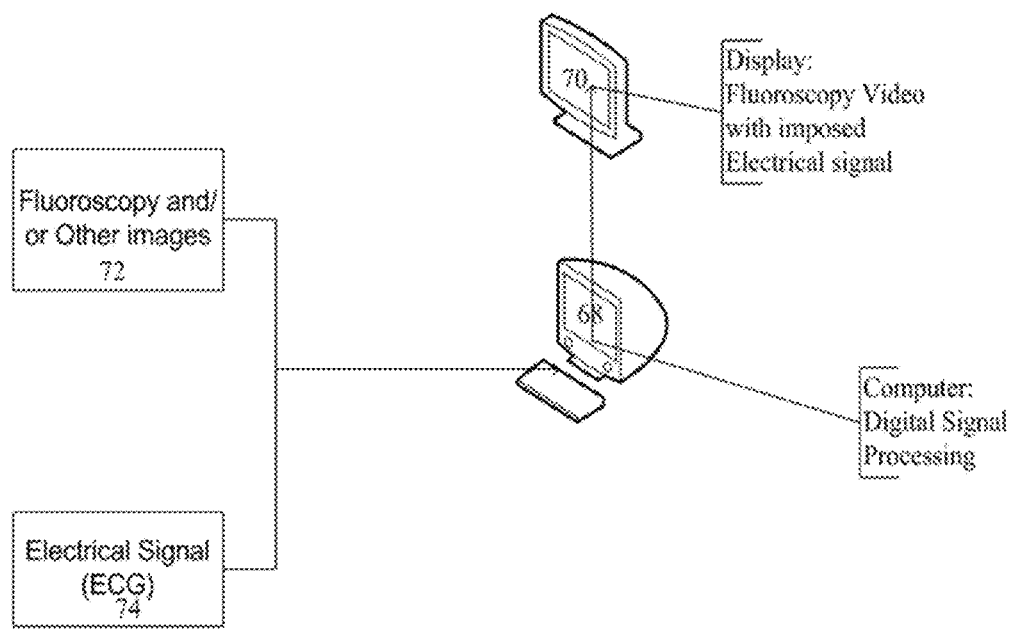
FIG. 22 is a block diagram showing energy interrupt for the procedure based on a command signal from a cardiac mapping (or cardiac monitoring/recording) system.

In the concept of this disclosure, a computer 68 is configured to receive multiple channels of electrical signals including 12-lead EKG and various intracardiac signals, shown in a simplified form in conjunction with FIG. 22. A computer, is generally a desktop workstation 68 (or a laptop 66—not shown) is configured to receive fluoroscopy 72 and/or other images into the computer 68. Additionally, there may be an output from the computer for feedback control of various things, for example interrupting energy delivery in certain situations. The interruption of energy delivery may be based on electrical signals and/or other parameters. One example would be interrupting energy delivery for AVNRT ablation based on timing relationships of the acquired atrial and ventricular signals. Another example would be interrupting ablation energy delivery based on esophageal temperature monitoring.

Ablation Stopping Box

Figure 23:
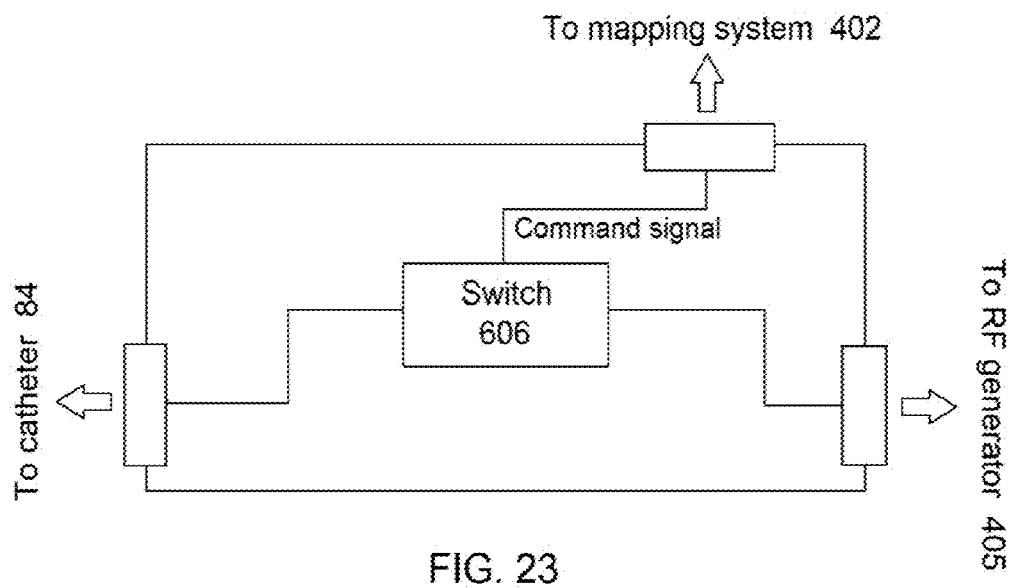
FIG. 23 shows electrical circuitry for energy interrupt (or stopping) of procedure based on temperature parameter(s) measurements.

The functioning of the stopping box is shown in conjunction with FIG. 23. The stopping box 404 is connected to the ablation catheter 84 on one end, an to the RF generator 602 on the other end. The stopping box 404 is also connected to the mapping system computer 402 (or cardiac monitoring/recording system 403). Based on meeting pre-determined criteria, selected by the physician or operator, the cardiac mapping system computer 402 sends a command signal to activate switch 606, to interrupt energy delivery to the ablation catheter 84.

Figure 24:
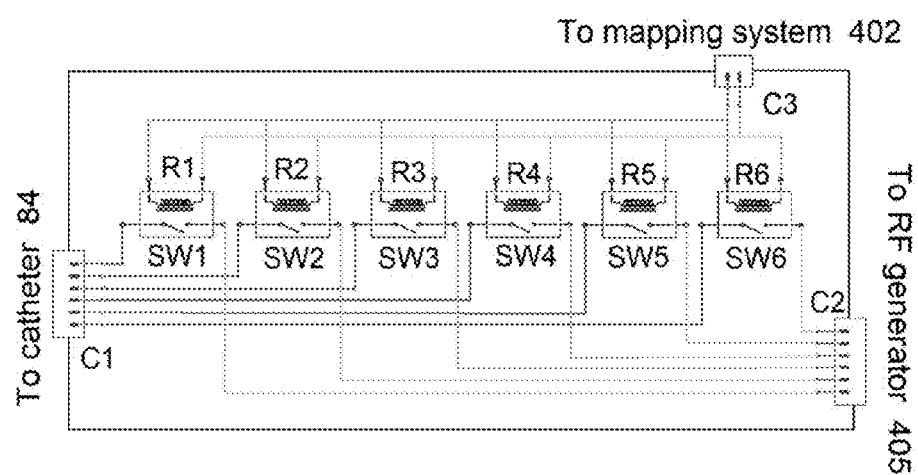
FIG. 24 shows implementation of electrical circuitry for energy interrupt (or stopping) of procedure based on temperature parameter(s) measurements.

In order to interrupt the RF energy delivery automatically during a procedure (based on pre-determined criteria) the system employs a stopping box 404. In one embodiment, the stopping box consists of six normally-closed DC voltage relay switches (SW1 to SW6) with 3 input/output connectors (C1 to C3). The schematic of the stopping box is shown in FIG. 24.

The numbers of relays are based on the specificity and brand of ablation catheter which goes to the patient's heart (600). In one embodiment two wires are used for measuring the temperature and the other four are for acquiring the intra-cardiac signals (from the distal pair and proximal pair). While ablating, one of the wires will conduct the RF signal from an RF signal generator instrument (602) and this wire is the one that is to be controlled by the stopping box for on-time energy interruption. The interruption command is generated from the mapping system (402).

Typically, the RF signal is 2 Watts with 0.5 Mega Hertz frequency and maximum 2 volts peak to peak voltage and 1 ampere electrical current. The rest of the signals are low voltage signals which barely exceed 1 volt. Thus, the relay switches should be able to tolerate the signals.

As mentioned earlier, we are just interested in interrupting the RF signal. But in order to prevent any unexpected damage to the RF generator instruments due to any current or voltage induction leakage via the returning wires, it is prudent to disconnect the whole path from the RF generator instrument and the ablation catheter by using six individual relay switches to be disconnected simultaneously. For this reason, as shown in FIG. 24, this embodiment has paralleled the relay part (R1 to R6) of all the switches and then connected to the mapping system (402). For the ease of implementing the design, we have used 6 identical relay switches with maximum RF signal tolerance.

The mapping system of this embodiment is able to provide 24 volt constant DC voltage for disconnecting the whole six relay switches simultaneously. Using DC voltage relay (instead of other switches like MOSFET transistors) generally increases the patient safety because in relay switches the coil part is completely isolated from the switch part and any unwanted frequency like the ones that harms the patient will not be transferred to the switch and won't mix the signals passing through. Additionally, in DC signals the harmful frequencies are already filtered.

Since the relay switches are normally closed, and after some processing and meeting some criteria in the mapping system they should open the circuit, there's no need for any impedance match between them and the ablation catheter 84 or RF generator 405.

The only important parameter in the switches (sw 1 to sw 6) is their closed state impedance which should be the minimum in order not to affect the ablation catheter working conditions.

The resetting process is done by the operator and by the absence of RF or any other signals and which makes the design simpler for other electrical issues.

The stopping box will be an interface between the ablation catheter and the RF generator instrument. So, regardless of the number of the wires used for the ablating process, the connectors on the stopping box where it is connected to the catheter and the RF generator should match the proper ones. These connectors could be two 14 pin female REDEL connectors on two opposite sides of the box corresponding to the color of the connectors on the catheter and the RF generator (C1 and C2). The other 2 pin connector which delivers the 24 volts DC voltage from the mapping system (C3), could be any reliable connector used for medical applications.

Use with Cryoablations

It will be clear to one skilled in the art, that the temperature monitoring system may be used for both radiofrequency (RF) ablations and cryoablations. In RF ablations the concern is injury due to heating. In cryoablation, the concern is injury due to cooling. In Cryoablations with cryoballoons, the temperatures are typically brought to −40° C. Potentially, the injury due to freezing could be carried over to the esophagus. In this embodiment, the alarm(s) and/or interrupt are due to reaching the limit of the decrease in temperature as opposed to increase in temperature in RF ablation. In either case, the intent is to avoid or minimize the injury to the esophagus.

Cryotherapy or use of cold temperatures to elicit a specific tissue response, has a history of effective medical use and cryoablation systems utilizing cryoballoons are also used routinely for atrial fibrillation ablations. The ultimate purpose of cryoablation is to freeze tissue in a discrete and focused fashion to destroy cells in a precisely targeted area. The application of cryothermal energy results in the formation of an ice ball. Cooling first occurs at the distal catheter tip in contact with endocardial tissue. Freezing then extends radially into the tissue, establishing a temperature gradient. The lowest temperature and fastest freezing rate are generated at the point of contact, with slower tissue cooling rates at the peripheral regions. The mechanism of tissue damage are complex and still debated, but involve freezing and thawing, hemorrhage and inflammation, replacement fibrosis, and apoptosis.

Generally in cryoablations tissue hypothermia causes cardiomyocytes to become less fluidic as metabolism slows, the ion pumps to lose transport capabilities, and the intracellular pH to become more acidic. These effects may be transient, depending on the interplay between temperature and duration. The shorter the exposure to a hypothermic insult and/or the warmer the temperature, the faster the cells recover. As a clinical correlate, this characteristic feature of cryoenergy permits functional assessment of putative ablation sites (i.e., cryomapping) without cellular destruction.

By contrast, the hallmark of permanent tissue injury induced by hypothermia is formation of ice crystal. As cells are rapidly cooled to freezing temperatures, ice crystals are first formed within the extracellular matrix, and then formed intracellularly. The size of ice crystals and their density are dependent on the combination of the following proximity to the cryoenergy source, the local tissue temperature achieved, and the rate of freezing, initially, ice crystals are formed exclusively in the extracellular space as the tissue temperature drops below −150 C. Progressive cooling to below −400 C results in the formation of intracellular ice crystals in the extracellular space results in it becoming relative hypertonic. In an attempt to reestablish osmotic equilibrium, there is a compensatory egress of water from the intracellular to the extracellular space, with subsequent cellular shrinkage, resulting in intracellular desiccation Further, the newly established osmotic gradient precipitates a diffusion gradient between extracellular and intracellular spaces, resulting in the net movement of H+ ions out of the cell, and the migration of solute ions into the cell. Concomitant increase in the intracellular saline concentration with a reduction in intracellular pH results in cellular protein damage, enzyme system impairment, and adverse effects on lipoprotein components of the plasma membrane. Of all the cytoplasmic components, the mitochondria are particularly sensitive and are the first structures to suffer irreversible damage.

Upon completion of the freezing phase, the tissue passively returns to body temperature resulting in a thawing effect. This second phase induces cellular damage through a combination of two mechanisms. First, recrystallization and coalescence of intracellular and extracellular ice crystals increase the osmotic damage and generate shear forces, which further disrupt tissue architecture. Second, restoration of microcirculatory function is associated with a hyperemic vascular response characterized by hemorrhage and inflammation (coagulation necrosis). Specifically, blood vessel walls become porous leading to increased capillary permeability and subsequent interstitial edema. This vascular congestion, combined with endothelial injury induces platelet aggregation and microthrombi formation, and culminates in vascular obliteration and ischemic cellular necrosis. As such, while the central region subjected to the coldest freezing temperature undergoes direct cellular damage, the surrounding microvascular injury results in the extension of tissue destruction.

The final phase of cryoinjury begins concurrent to thawing and is characterized by reactive inflammation, followed by tissue repair and replacement fibrosis. Over the subsequent weeks, these processes culminate in the generation of a mature lesion, which has a distinct, well-circumscribed central region of dense fibrosis surrounded by a narrow border zone of viable cellular death (due to microvascular injury and apoptosis).

Generally, a cryocatheter consists of a hollow shaft with a closed distal end containing a cooling electrode tip, integrated thermocouple device and three proximal ring electrodes for recording and pacing. A console that contains the cryorefrigerant fluid. The cooling liquid travels through the inner delivery lumen to the catheter tip, where the cryorefrigerant is pressurized and released. This accelerated liquid-to-gas phase change results in rapid cooling of the distal tip. The gas is then conducted away from the catheter tip through a second coaxial return lumen maintained under vacuum and evacuated in the hospital medical gas disposal system.

The console allows the operator two different modes of operation. The first is the cryomapping mode in which the tip is cooled to a temperature not lower than −300 C for a maximum of 80 seconds so as to prevent irreversible tissue damage. The second mode is cryoablation, which results in cooling of the catheter tip to at least −75° C. for a programmable period (nominally 4 minutes), producing the permanent lesion. The cryomapping mode can be used for an indefinite number of times before cryoablation. Cryoablation may be initiated at any time during a cryomapping application or, from the onset, if the operator wishes to forego the cryomapping function.

One of the most exciting and truly remarkable characteristics of cryothermal energy is the ability to dynamically and prospectively asses the ability to safety and efficacy of a potential ablation lesion site, because a period of reversible electrophysiologic tissue inhibition obligatorily precedes permanent tissue destruction (a process that that can be dynamically manipulated by varying the temperature and/or time of application). While extreme freezing (i.e., tissue temperature colder than −50° C.) results in near instantaneous permanent tissue injury, a functional effect may be obtained at some lethal temperatures (i.e., −10° C. to −25° C.), but complete recovery of all electrophysiologic properties and no histologically identifiable damage. Prior mapping is not theoretically possible, but the broad temperature/time window between reversible and irreversible effects renders this feature readily clinically applicable. This by identifying the desired substrate before definitive ablation, the appropriate catheter placement site may be confirm to be efficacious (i.e., efficacy cryo mapping) and/or safe i.e., safety cryo mapping). Reversible cryo mapping may be of particular importance when ablating with myogenic substrates located near critical sites such as the AV node, where images target lesion may have major consequences. Reversibility observed with cryotherapy oh energy contrasts starkly with RF energy. With RF ablations, hydrothermal tissue energy leading to reversible loss of excitability occurs at a median tissue temperature of 48° C., as reversible tissue destruction occurs at tissue temperatures greater than 50° C. The reversibility window is, therefore, too narrow for safe clinical applications.

Even though the disclosure is described primarily with cryoballoon catheter for atrial fibrillation, such as the Arctic Front® available from Medtronic. It will be clear to one skilled in the art, that other balloon catheters are also available or will soon be available. The method and system also applies to any balloon catheter for pulmonary vein isolation and/or ablation for atrial fibrillation.

One such catheter is a balloon catheter where laser energy is applied from inside the balloon, for sioating the pulmonary vein in a point-by-point type of ablation.

Another catheter being tested in clinical trials, also applies energy though the balloon for "single shot" pulmonary vein isolation, but heats up the tissue instead of freezing the tissue as with cryoballoon catheter.

The method and system described in this disclosure can also be used for any balloon based catheter utilized for atrial fibrillation ablations, and is considered within the scope of this invention.

Fluoroscopy and/or Medical Images (Including 3-D Images) Based System for Cryoballoon Ablations A fluoroscopy and/or medical images based system for cryoballoon ablations has been disclosed in Applicant's provisional application No. 62/346,539 having a filing date of Jun. 6, 2016 entitled "FLUOROSCOPY AND CARDIAC IMAGE(S) BASED MAPPING SYSTEM FOR GUIDING CRYOBALLOON ABLATIONS FOR ATRIAL FIBRILLATION WITH AUTOMATIC FLUOROSCOPIC RECORDING MECHANISM". The disclosure of the provisional application is also summarized below for convenience.

The mapping system of the current disclosure is designed to facilitate the cryoballoon ablation procedure by providing an actual patient's cardiac image based mapping system, as opposed to sensor based geometry on a computer model. These medical images may include any combination of images including Fluoroscopy, Ultrasound, Intra-cardiac Echo (ICE), Computed Tomography (CT), Magnetic Resonance Image (MRI) or any other type of medical images. A combination of medical images may also be used for example a combination of fluoroscopy and ICE may be used, or any other combination of medical images may be used. The general concept of the mapping system is shown in conjunction with FIGS. 1A, 1B, 1C and 25.

In one aspect of the system and method, live fluoroscopy 558 images are brought into the computer workstation of the Mapping System 550. Several computer boards are available for this purpose and are well known in the art. Also, as shown in FIG. 25, electrical signals 566 of the patient including both surface and intracardiac are brought into the computer 550 of the mapping system.

Figure 25:
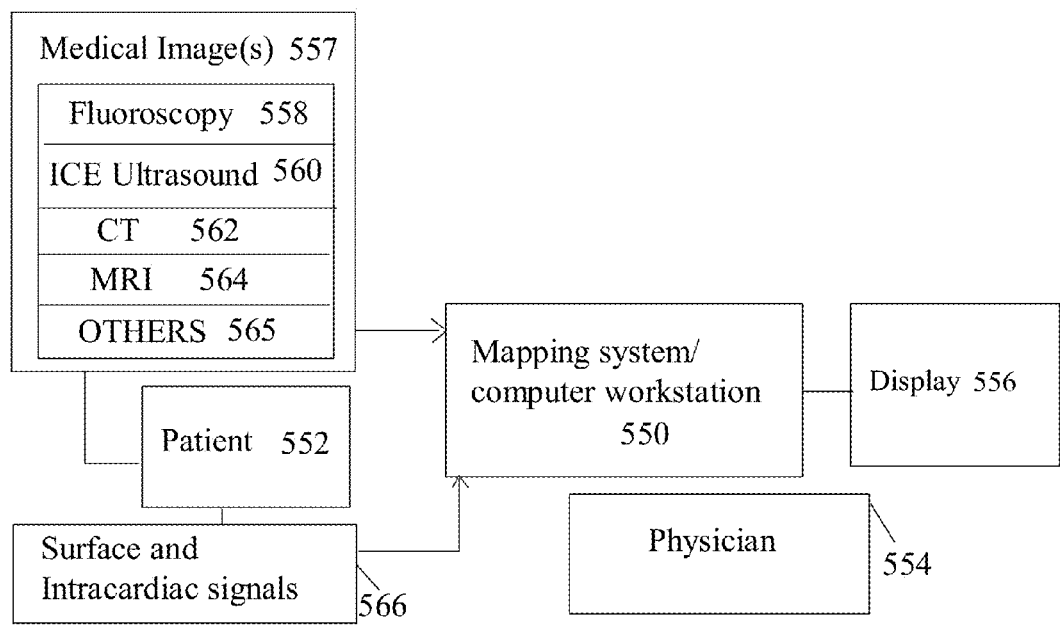
FIG. 25 is a generalized block diagram showing fluoroscopy or medical images based cardiac mapping system for cryoballoon ablations or for radiofrequency (RF) ablations.

As shown in FIG. 25, Intracardiac Echo (ICE) 560, computed tomography (CT) 562, Magnetic Resonance Imaging (MRI) 564 may also be used. Additionally, a combination of images may be used. For example, cryoballoon may be localized both on fluoroscopic 558 and ultrasound (ICE) 560 images. Further, the fluoroscope and ICE images may be registered to each other in method and system of the current disclosure.

Figure 26A:
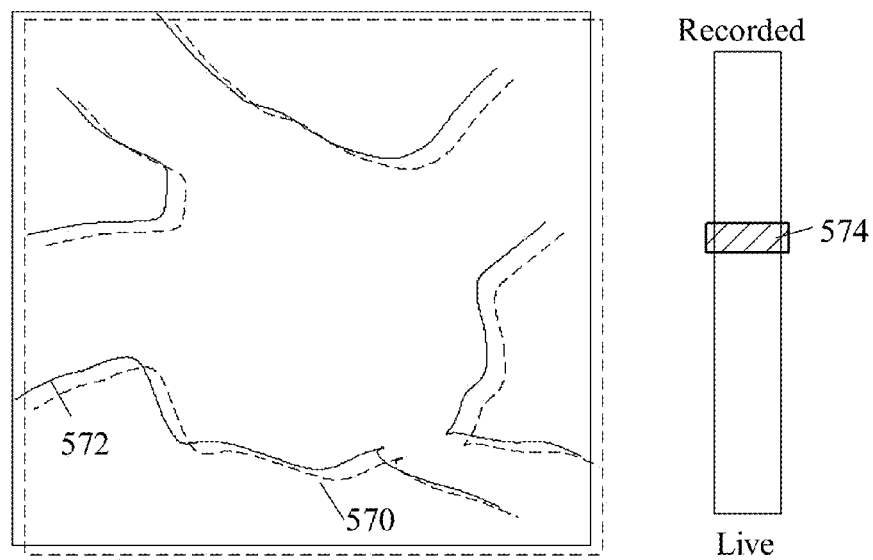
FIG. 26A depicts a live image and recorded image superimposed on each other with a way to adjust the transparency factor between the live and recorded image.
Figure 26B:
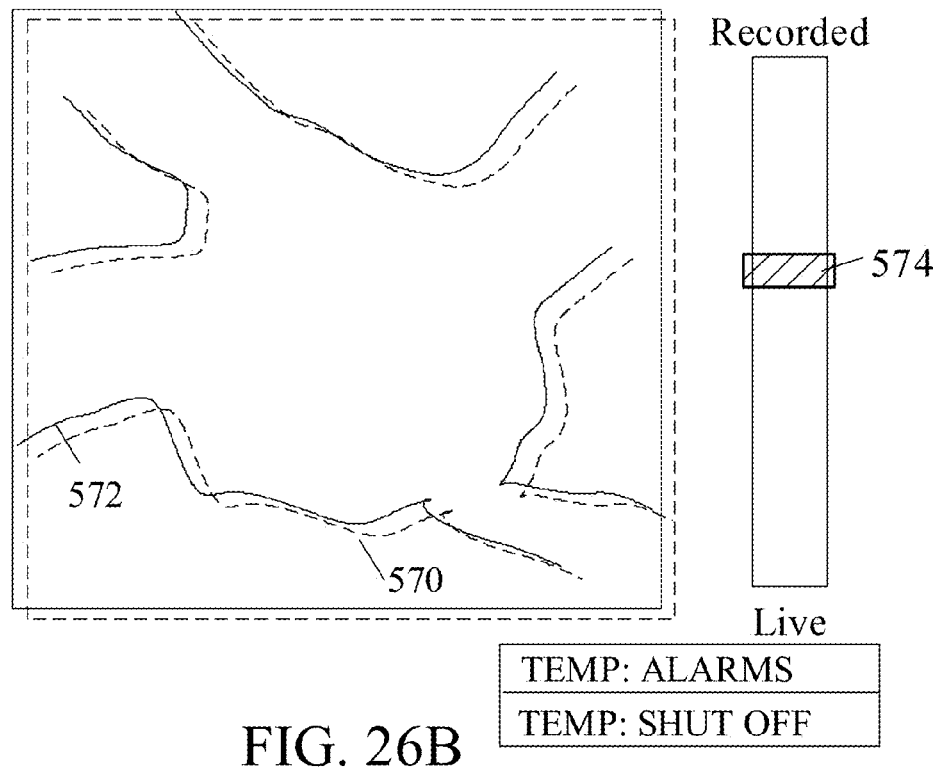
FIG. 26B depicts a live image and recorded image superimposed on each other with a way to adjust the transparency factor between the live and recorded image with temperature module interface.

In one preferred embodiment, shown in conjunction with FIGS. 26A and 26B, a high resolution, high clarity image, i.e. with contrast medium or "dye" injection is recorded. These images will generally be recorded with a rotation of the fluoroscope. The advantage of rotation is that it provides 3-dimensional (3D) information. Additional recordings without rotation may also be recorded in one view such as an AP view for example.

Generally, in fluoroscopy high image quality is obtained by increasing radiation dose level. In the typical workflow of the method, highest resolution setting (Cine loop—30 frames/sec) is used for the recording. In addition, a contrast medium or "dye" is injected for the recording. The combination of highest exposure and contrast medium provides a high quality image which clearly delineates the left atrium (LA) and pulmonary vein anatomy. The high resolution recording will generally be very brief so the patient is exposed to the high radiation level for only less than 10 seconds, more typically 5 seconds or less. For the purposes of injecting contrast medium or "dye" injection, a pump is preferably utilized but is not essential, as the injection may also be done by hand. In another aspect, less than the highest radiation level may also be utilized, based on the discretion of the physician and is within the scope of this disclosure.

Figure 27:
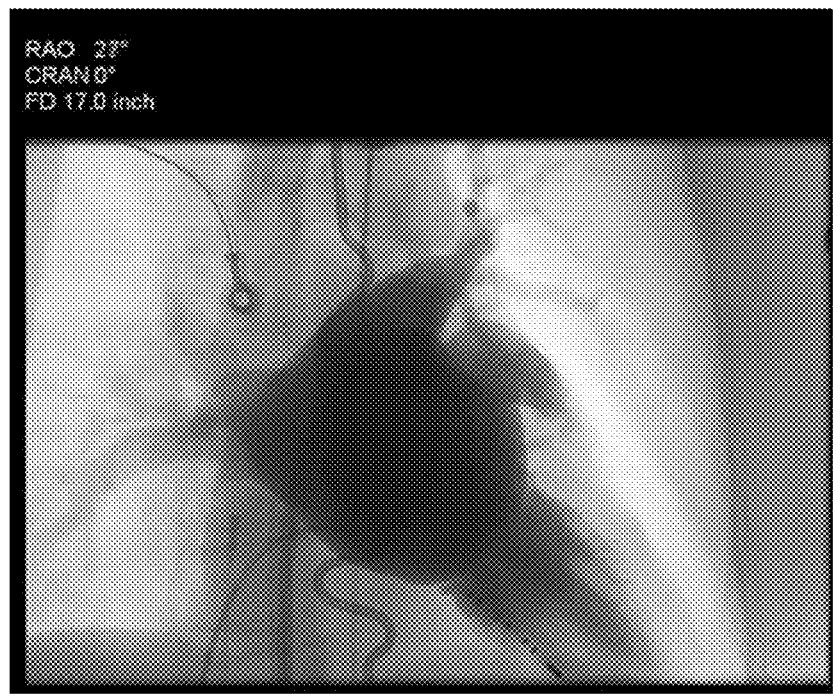
FIG. 27 shows an example of a recorded high resolution image of the left atrium recorded with "dye" injection.

Therefore in the first step, at the maximum 30 frames/sec (cine loop) resolution, a "dye" injection is performed and a rotation is recorded in the mapping system. This rotation will generally show a clear outline of the left atrium and the pulmonary veins at different angles. One example of a high resolution image is shown in FIG. 27.

There is a general need for a method and system to record a procedure that uses fluoroscopy, on a computer based system and for the recording to occur only when the physician pushes the pedal and the fluoroscope (or radiation) is ON. Further, automatically stopping the recording when the physician takes the foot off the pedal, and the fluoroscope is turned OFF.

This is true for any situations where it is desirable to record the fluoroscopy from a procedure. This has application for any cases that require fluoroscopy in fields of cardiac electrophysiology, interventional cardiology, or any fields of medicine that require fluoroscopy for a medical procedure. One application of this is in the current application, but the method and system can be used for any application or procedure requiring fluoroscopy.

In the method and system of this disclosure, for the current application more than one recording is generally made from the fluoroscope in the beginning part of the procedure. In one aspect of this disclosure, the software is configured and programmed such that the recordings from the fluoroscopy may be activated manually, or the ON-OFF switching process for the fluoroscopic recordings may be automated via the software utilizing optical character recognition (OCR).

In the manual portion of the software coding, a software button may be programmed and configured such that an operator starts the recording from the fluoroscope while the physician has activated the fluoroscope (generally by pressing a foot paddle). Similarly the operator stops the recording after the physician has taken the foot off the paddle.

Since this method is very inefficient and for many types of procedures it is not practical, it is highly desirable to program and configure the software such that the recording automatically starts when the physician pushes the paddle, and the fluoroscope is ON. Similarly in this methodology, the computer automatically stops recording when the physician takes the foot off the paddle. Generally, the fluoroscope is ON only when the physician has the foot on the paddle.

In one aspect of this disclosure, the method and system utilizes optical character reader (OCR) technology to trigger as an automatic ON-OFF switch for recording in the mapping system only while the fluoroscopy is ON.

Figure 28:
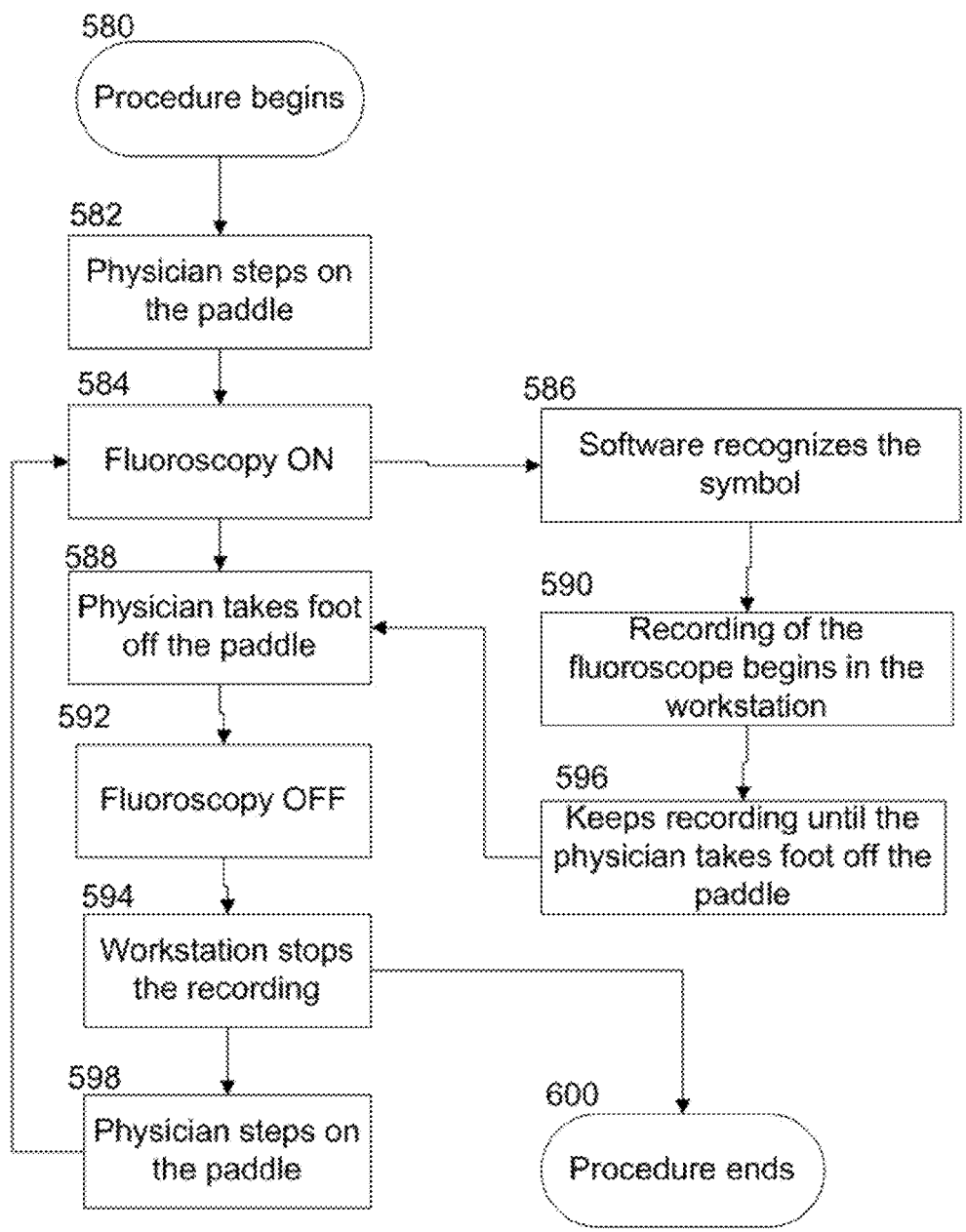

Generally, when the physician pushes on the paddle and fluoroscopy goes ON, a symbol appears on the fluoroscopy to show that the fluoroscope (or radiation) in ON. The symbol element is generally shown on the top left corner of the fluoroscopy screen, and the symbol stays there while the fluoroscopy is ON. The exact symbol and placement is dependent on the specific company that manufactures the fluoroscopy equipment. Since, the (radiation) symbol appears on the screen, the software is coded and trained to recognize when the symbol appears and disappears utilizing OCR training and algorithms. This may be done utilizing one of various software languages as is known in the art. Further, in this disclosure the appearance and disappearance of the symbol is used as a switch to turn the recording ON and OFF. This is summarized with the help of a flow diagram in FIG. 28.

In step 580 the procedure begins. At some point the physician needs fluoroscopy for visualization and in step 582 the physician steps on the paddle. This causes the fluoroscopy to turn ON which is step 584. Once the fluoroscopy is ON, the software recognizes the symbol (step 586), and starts the recording in the computer workstation or the mapping system (step 590). In step 596, the recording stays on until the physician takes the foot OFF the peddle (step 588). Once the physician takes foot off the paddle, the fluoroscopy is turned OFF. This triggers step 594 where the workstation stops the recording. If the physician steps on the paddle again, the fluoroscopy is turned ON again as seen in step 584. This ON and OFF continues, and each time the segment is recorded and saved in a separate file, until the procedure ends (step 600)

Figure 29:
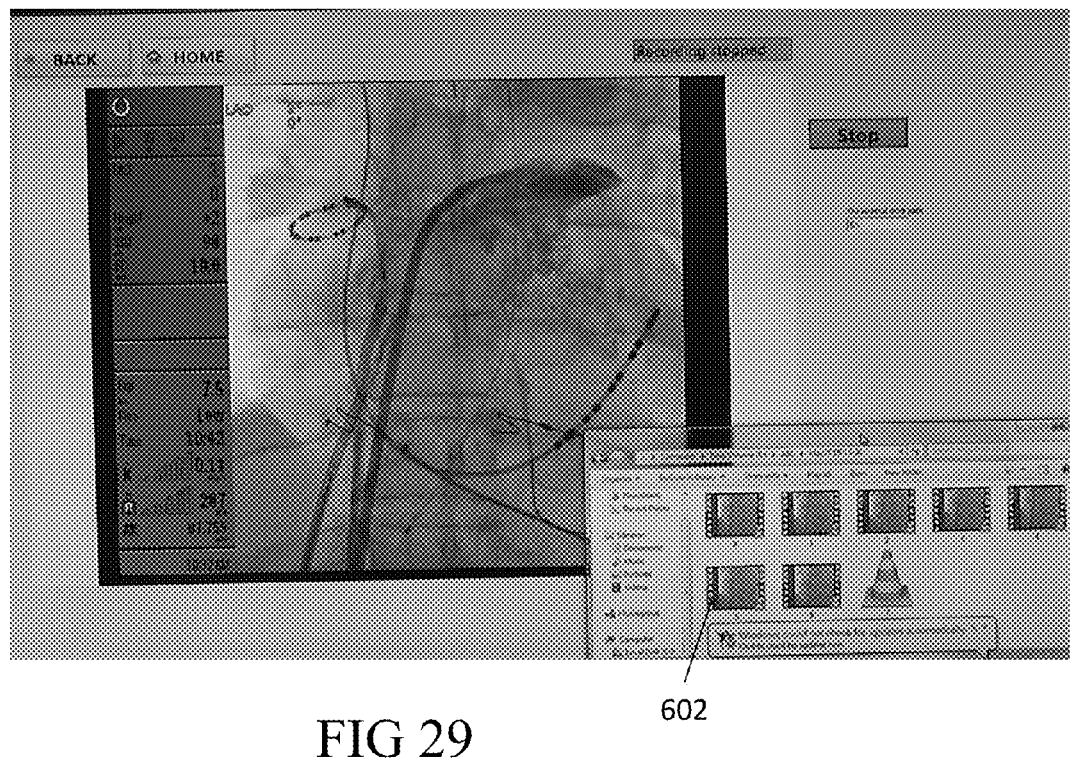
FIG. 29 shows an example of implementation of automatically recording only while the fluoroscopy is on, and saving videos in a folder.

In our implementation, once the recording is started, every time the physician presses on the foot paddle and then releases it, the segment is stored in a separate file at a path specified in the code. The folder keeps on accumulating the files until the operator is ready to use them. This is shown in conjunction with FIG. 29. The panel on the lower right corner 602 shows that, every time the physician goes ON and then OFF, a file is stored of the fluoroscope recording for that particular duration which is variable.

The software is configured and programmed such that when symbol appears, it acts as a switch for the system to start recording, and when the symbol disappears the system is commanded to stop recording. The implementation of this may be done utilizing various different software's, as is known in the art.

In the implementation, the coordinates of the area where the symbol appears is regionalized and stored in the code. The software is then trained to recognize the symbol when it appears and trigger the recording mode.

Going back to FIG. 26, the recorded high resolution image 570 and live fluoroscope image 572, which is generally in lower resolution are displayed and adjusted in a way such that they are layered exactly on top of each other on the screen, shown as 570 and 572 in the figure. Further, the software is configured and programmed such that a transparency factor between the two said images can be adjusted. This is depicted in our implementation in conjunction with FIG. 26, via a slider bar 574, which can be adjusted for the transparency factor which is variable.

The transparency factor is generally a level of transparency between the recorded image and the live image. The relative transparency level can be adjusted with a slider bar 574 in our implementation. At one extreme of transparency only the recorded image is visible and live image is masked. At the other extreme only the live image is visible and the recorded image is masked. At any level in-between the relative weight between or clarity between recorded or live image shifts and is adjustable.

By adjusting the transparency level, the physician can utilize the outline of the pulmonary veins highlighted with contrast medium injection, and appropriately place the catheter utilizing the combination of live fluoroscopy and recorded images. As known to one skilled in the art, this can be implemented utilizing a number of different softwares, as is well known in the art.

Typically, the transparency factor is adjusted somewhere in the middle based on physician preference and choice. Advantageously, the physician gets the benefit of the recorded and stored high resolution image while being exposed to only low level of radiation.

Figure 30:
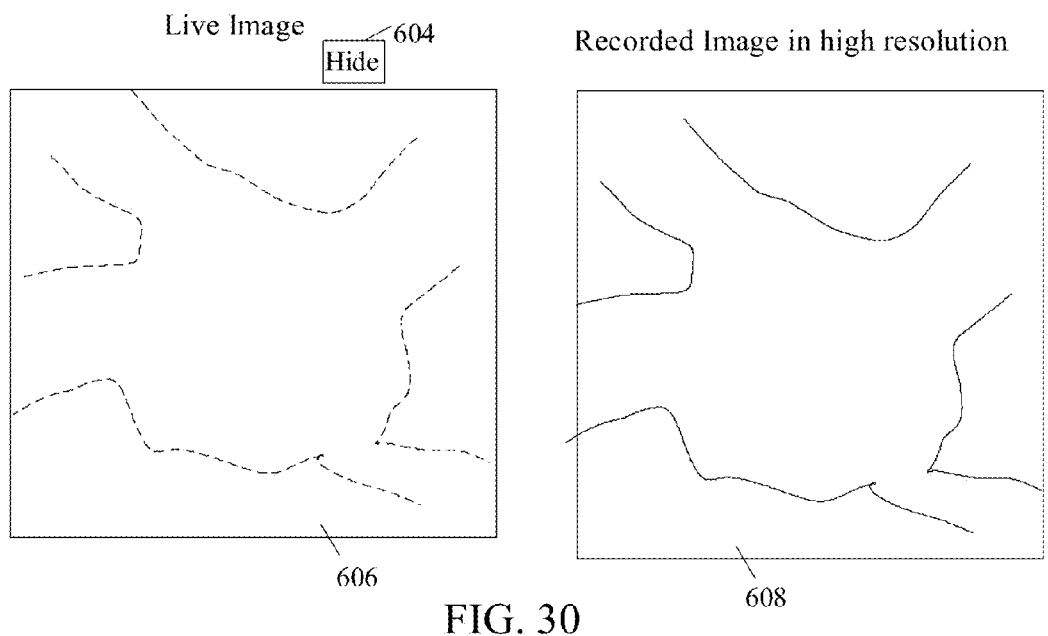
FIG. 30 depicts side by side images where one image is a recorded high resolution image with contrast medium ("dye") injected, and the other image is live fluoroscopy image.

In another embodiment, as depicted in FIG. 30, the recorded high resolution image 608 and live fluoro images 606 are depicted next to each other. Based on the high resolution image 608 with contrast medium, the outline 603 of the four pulmonary veins can appear drawn on the live fluoroscope, as a guide for cryoballoon placement.

Figure 31:
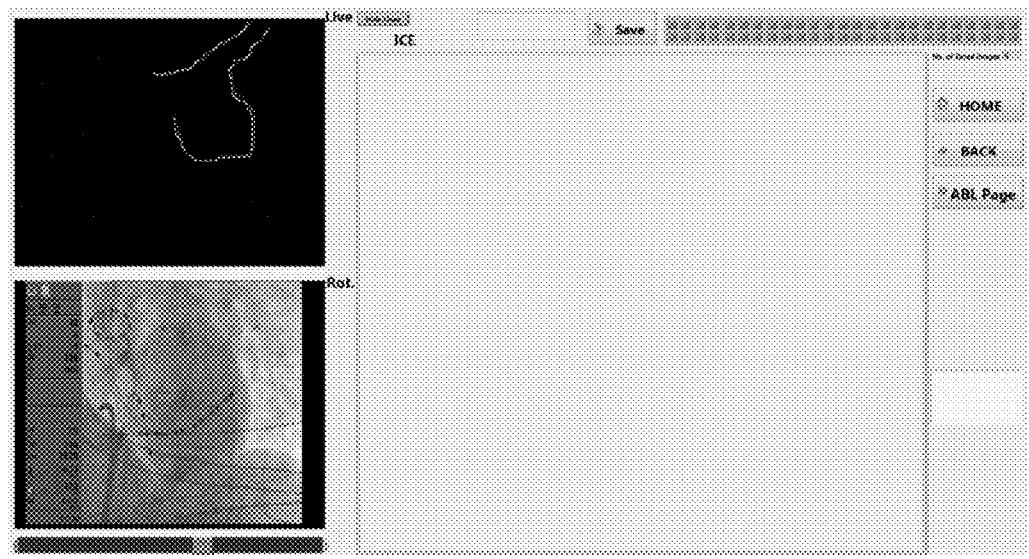
FIG. 31 shows one screen in the implementation of the mapping system where recorded high resolution image, live fluoroscopy image and intra-cardiac echo (ICE) is shown in one screen.
Figure 32:
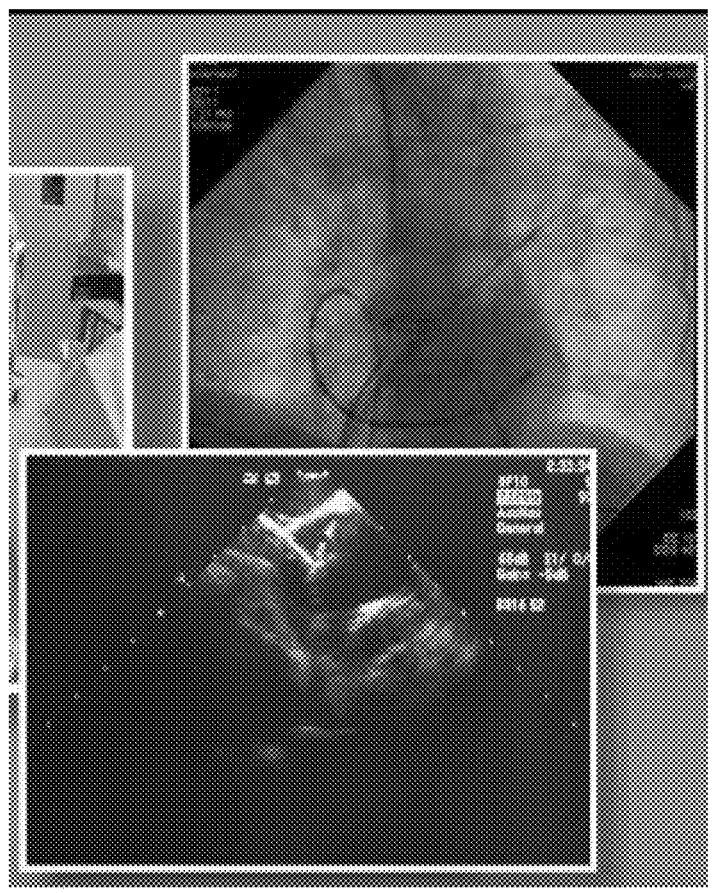
FIG. 32 shows another example of implementation where fluoroscopy and ICE are shown for placement of the cryoballoon for cryo ablations.

In one aspect live fluoroscopy, recorded enhanced fluoroscopy and ICE images are displayed, as is shown in conjunction with FIG. 31. In one aspect, fluoroscopy and ICE may be used in conjunction with each other (shown in FIG. 32) for the optimal positioning of the cryoballoon.

Cryoablation using cryoballoon is generally performed utilizing a freeze, thaw, freeze technique. As previously stated, the goal is to render the tissue between pulmonary veins and the left atrium (LA) to be electrically inactive by the ablation procedure, for all the pulmonary veins. Generally, one pulmonary vein is done at a time.

Figure 33:
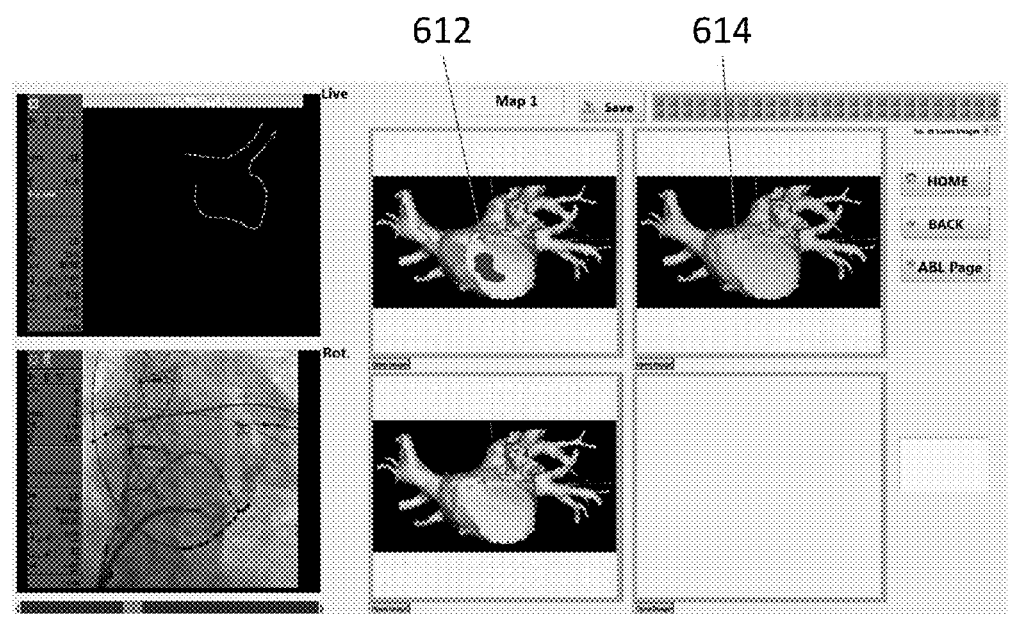
FIG. 33 shows another example of implementation where, recorded high resolution fluoroscopy, live fluoroscopy and CT images are displayed on the same screen.

In one aspect, CT scans if available are also displayed in addition to enhanced fluoroscopy image and regular fluoroscopy image. One example of an implementation of this is shown in FIG. 33. In this example, CT images 612, 614 are displayed next to fluoroscopy.

Figure 34:
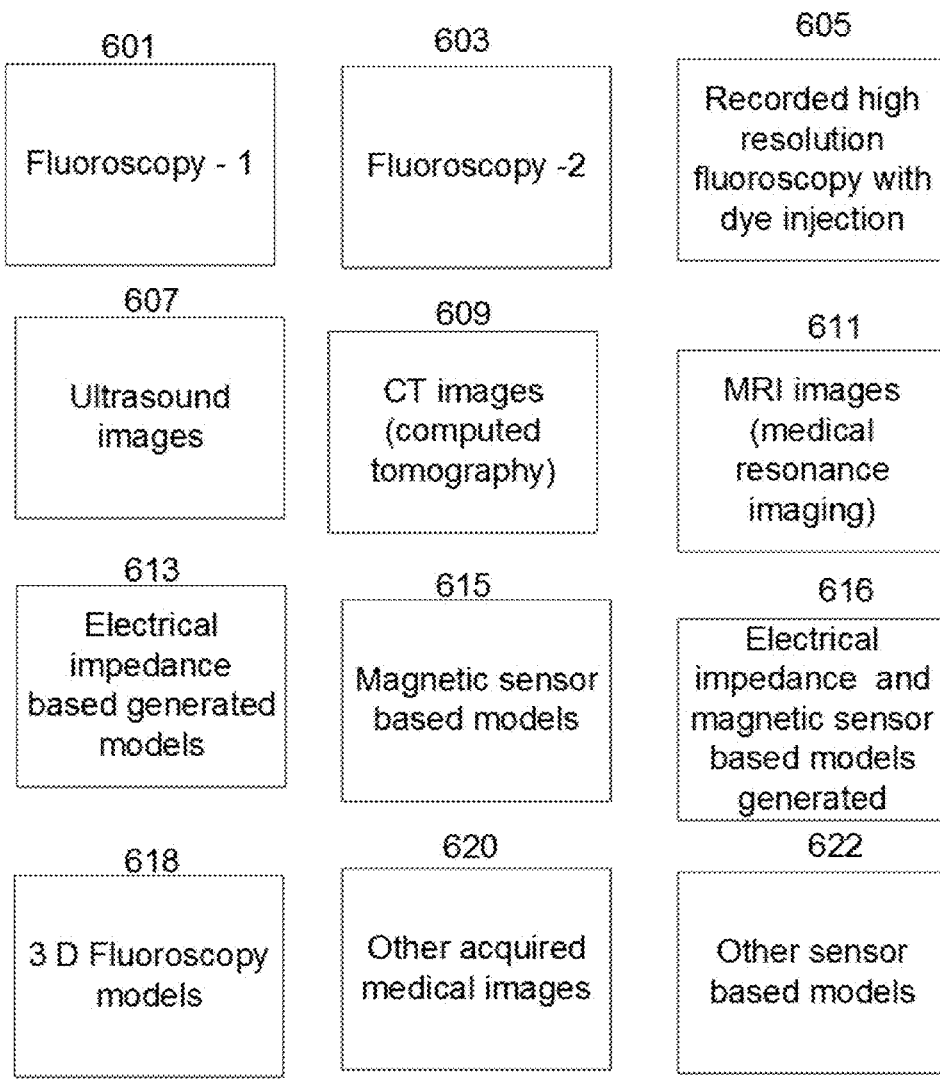
FIG. 34 is a block diagram showing different types of medical images that may be utilized or used in any combination in the mapping system of this disclosure.

Further, in the method and system of this disclosure, various different types of medical images are utilized. These are shown in FIG. 34. These include fluoroscopy image(s) or various layers of fluoroscopy images 601, 603. The fluoroscopy image(s) include mono-plane or bi-plane fluoroscopy, fluoroscopy rotations, fluoroscopy rotations with dye injections or fluoroscopy based 3D models. Live fluoroscopy image(s) may be superimposed or overlaid on top of (or bottom) a recorded fluoroscopic video or image which has been recorded in high resolution with contrast medium (or "dye") injections.

Other images include ultrasound images 607, CT (computed tomography) images 609, MRI (magnetic resonance imaging) images 611, electrical impedance based generated models 613, magnetic sensor based models 615, electrical impedance and magnetic sensor based models 616, 3D fluoroscopy models 618, other acquired medical images 620, and other sensor based models 622.

In the method and system of this disclosure, any combination of image modalities shown in FIG. 34 may be used by the mapping system for Cryoballoon ablation mapping system, or any other balloon based catheter based mapping for atrial fibrillation ablations. It may also be utilized in radiofrequency (rf) ablations and placement of a circular catheter around pulmonary veins.

Some of these combinations, without limitation are shown in FIGS. 35-42.

Figure 35:
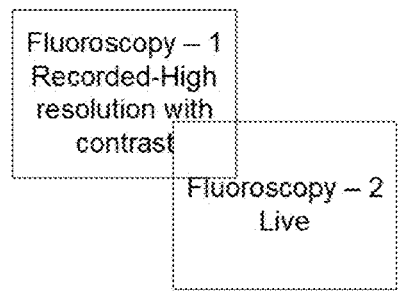
FIG. 35 is a block diagram showing two layers of fluoroscopy images overlaid/stacked on top of each other.

In one aspect as shown with FIG. 35, live fluoroscopy may be aligned and superimposed or overlaid on top (or bottom) of a recorded high resolution fluoroscopy, which is recorded with contrast medium injection. The software is configured and programmed in a way, that a transparency factor adjusts the relative transparency between the recorded and live images. The recorded image is generally recorded in high resolution, with contrast medium (dye) injection. Provided the fluoroscope C-arm view and magnification factors are not changed, this technique offers the advantage that the live fluoroscopy manipulation or placement of leads or Cryoballoon catheter can take advantage of the high resolution and contrast medium (dye) injection.

In applicant's clinical testing this has shown to be of significant help in placing of the Cryoballoon catheter in each of the four pulmonary veins. The same methodology also applies to any balloon based catheter as an aid for the proper placement of the catheter in the left atrium or around pulmonary veins.

One implementation is shown with FIGS. 46-48. In the first part of the implementation shown with FIGS. 46 and 47, a recording is made with contrast medium (dye) injection. FIG. 46 shows contrast medium in the superior pulmonary vein 636. A lumen catheter 634 is inserted in the left atrium close to left superior pulmonary vein 636, and the dye (or contrast medium) is injected. A recording is made of the dye injection.

Following that, as is shown in FIG. 47 in our implementation, the recorded image (with dye injection) 640 is placed underneath the live fluoroscopy image 642. A transparency factor bar 644 is adjusted by an operator to have the right ratio of recorded image vs live fluoroscopy image. Utilizing this methodology, the physician is able to place the Cryoballoon catheter in appropriate pulmonary vein for the ablation procedure.

Figure 36:
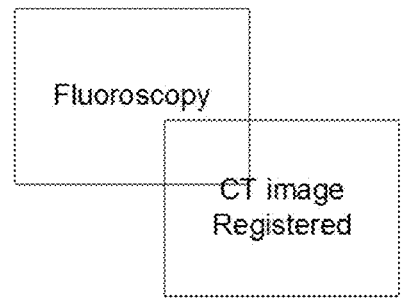
FIG. 36 is a block diagram showing CT images registered with fluoroscopy images.
Figure 37:
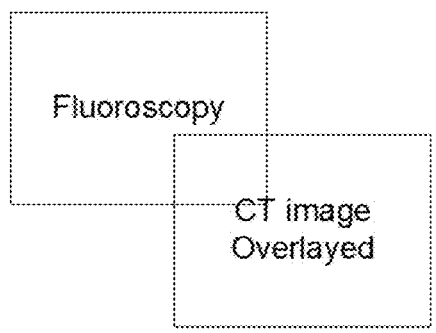
FIG. 37 is a block diagram depicting CT images overlaid/stacked on top of fluoroscopy images.
Figure 38:
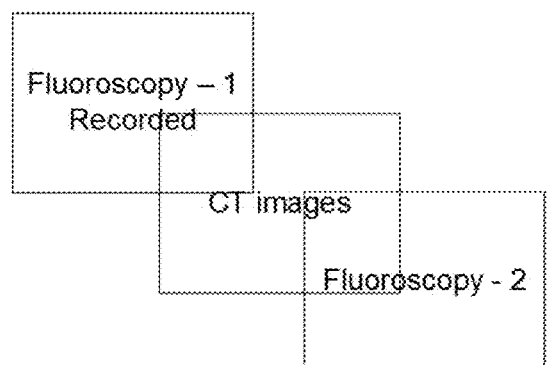

In another aspect, as shown with FIGS. 36 and 37, computed tomography (CT) images may be combined with fluoroscopy. It will be clear to one of ordinary skill in the art, that the CT image(s) may be registered or just overlaid on the fluoroscopic image(s). Registering the images involves some extra steps such as matching known anatomical points on both of the images. This is shown with FIG. 36. FIG. 37 shows an embodiment, where the CT images are combined or matched and overlaid on fluoroscopy, but are not registered. In Applicant's clinical testing this is still very useful. In this aspect, an operator visually matches the structures of the CT image with the structures on the fluoroscope. This is aided by the contrast medium (dye) injection.

Transparency

When a picture-1 (image or video) is placed on top of another picture-2 (image or video), the picture on the bottom (picture-2) is normally completely hidden. By utilizing software, a transparency factor (which can be gradual and continuous) can be configured and programmed. At one extreme of the transparency factor, the picture-2 at the bottom is completely hidden, and picture-1 is at full view. At the other extreme, picture-1 on top can be completely masked and picture-2 on bottom is in full view. This would be similar or equivalent to the top picture becoming transparent like clear glass. Utilizing software, the relative transparency between the two pictures can be easily adjusted such that the picture on the bottom is visible enough to show and take advantage of, while the picture on top (picture-1) can be used for any purposes.

In one application of this disclosure, the picture-1 can be live fluoroscopy image or video and the other (picture-2) can be a recorded fluoroscopy image of video, which was recorded with contrast medium injection ("dye") preferably in the highest resolution. By placing the live fluoroscopy on the recorded image or video with contrast, and adjusting the relative transparency between the live and recorded images, both can be utilized in a meaningful way. That is, live fluoroscopy can be used for catheter manipulation and placement, utilizing the recorded detailed anatomy and structure boundaries that are available from the contrast medium injection and which is placed underneath. The live and recorded images can also be interchanged, i.e. the recorded image can be placed on top and live fluoroscopy can be on bottom.

Similarly in another application, a CT model can be placed on top of, with structures aligned and matched with a recorded dye injected fluoroscopy, then in turn live fluoroscopy can be placed on top of these two images. By adjusting the transparency factor between the three images, all the images can be utilized. For example, the catheter can be manipulated and placed utilizing live fluoroscopy, while using the anatomic details of recorded "dye" injection, and the detailed anatomy of the CT scan.

The same methodology can be applied to different types of images shown in FIGS. 35 to 42.

Figure 49:
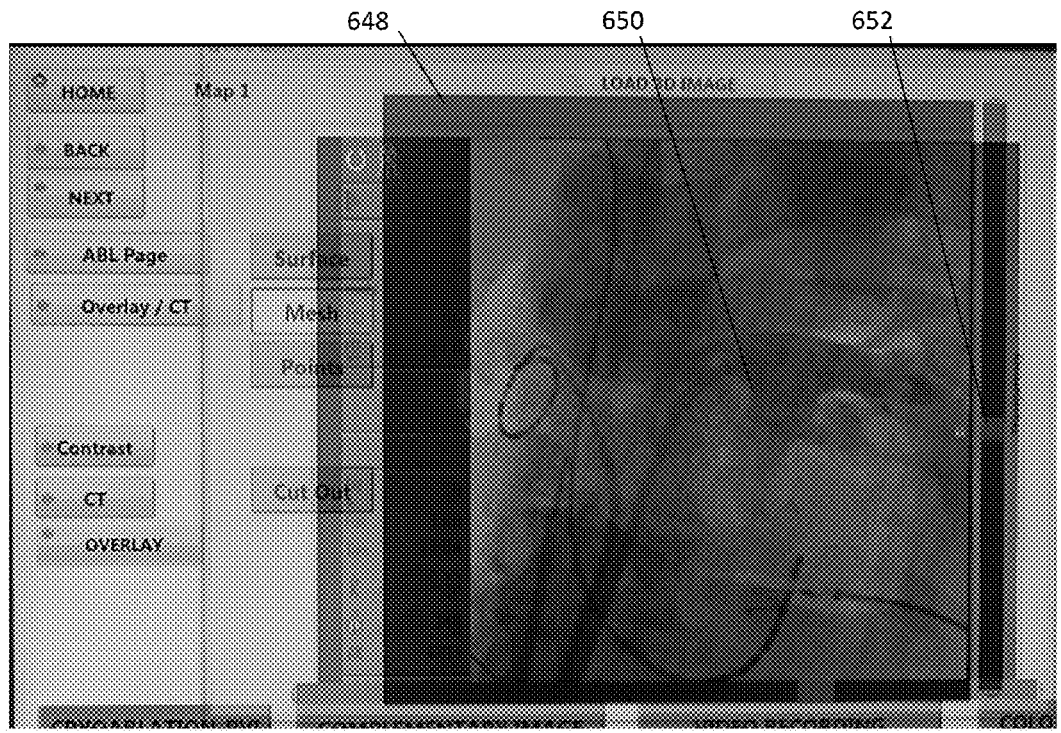
FIG. 49 is a diagram showing one implementation where a CT image is overlaid on a recorded fluoroscopy image with contrast medium ("dye") injection, and the structures are matched.
Figure 50:
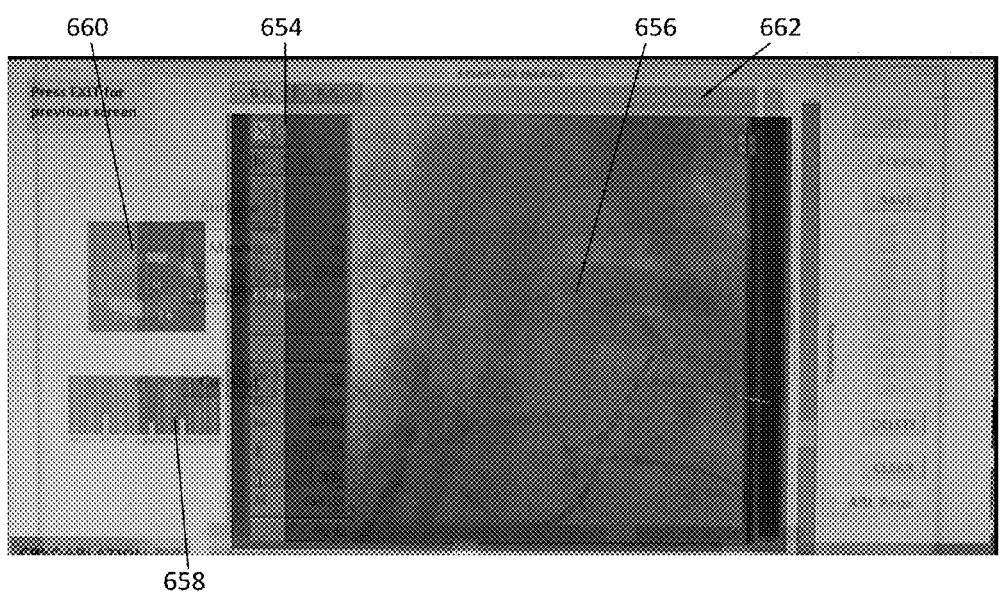
FIG. 50 is an implementation of the concept shown in FIG. 38, i.e where CT image is overlaid on a recorded fluoroscopy image and live fluoroscopy is overlaid on top of that. Further, electrical signals are also displayed on top fluoroscopy layer.

An implementation of this is shown with FIGS. 49 and 50. In the first step shown in FIG. 48, a volume rendering is done of the CT image 646. This volume rendering may be done on the mapping system via an appropriate software, or may be done on separate computer. The volume rendered 3D CT image 646 is then brought into the mapping system workstation. In the next step shown in FIG. 49 the volume rendered 3D CT image is superimposed on the recorded fluoroscopy image. As previously mentioned, this superimposition may be performed by registering the CT image on the fluoroscopy image or via the operator aligning the CT image with the recorded or live fluoroscopy image. Of course, for performing the registration process, points or tags will have to be specified on the both the fluoroscopy image and the CT image.

A transparency factor bar is generally adjusted by the operator, to show the relative weight of the fluoroscopy image vs the CT image.

In another aspect, two layers of fluoroscopy may be combined with the CT image. This is shown in conjunction with FIG. 50. In this aspect, high resolution fluoroscopy with contrast (dye) medium injection is recorded and stored in the computer (of the mapping system). In the next step, the appropriate images are brought on the monitor screen. Following that, the CT image which is 3-D is overlaid or registered on the recorded or high resolution with dye image.

It will be clear to one skilled in the art, that for the CT image to be registered approximately three common points on the each structure will need to be identified and tagged. Then via known algorithms, the images are registered when the algorithms are executed.

As an alternative, the images are matched by an operator. By utilizing the outline of the contrast medium, the CT image is matched to the outline of the fluoroscopy structures by the operator manually. This can be done, as the operator is manually able to pan, zoom and rotate the CT model on the monitor manually using a mouse. Since the placement of the Cryoballoon catheter is done only one vein at a time, the operator only needs to match only one vein at a time. The advantage is that this can be done quickly and is relatively simply.

Applicant's implementation and testing of this aspect is shown in conjunction with FIG. 50. In this figure, the first (bottom) image on the screen is a high resolution recorded fluoroscopy segment with dye injection, which has a nice outline of the left atrium and at least one of the pulmonary veins. The CT image 656, is placed and aligned by the operator on the outline of the heart, which is aided by the "dye" or contrast medium injection. On top of these two layers (recorded fluoroscope and CT image) is a live fluoroscopy layer. This gives a physician the advantage of the contrast medium (dye) injection and the detailed anatomy from the CT scan.

This aids the physician in the proper placement of the Cryoballoon catheter and/or the electrode catheter in and/around the pulmonary vein. After placing the Cryoballoon catheter, and appropriate placement of the balloon, the ablation or freezing is performed. Generally, the physician may inject a small amount of dye from the Cryoballoon catheter to check the seal of balloon with the pulmonary vein ostium (os).

The above procedure will be repeated at least four times to isolate all four pulmonary veins, as is generally done to complete the procedure.

In one implementation, the software is configured and programmed such that visual indicator of voltage levels from each pulmonary vein are shown as bar graphs indicating peak-to-peak voltage levels from different areas of the pulmonary vein. Actual signals are also shown below the bar graph.

In one embodiment, the bar colors are color coded to display the voltage levels. In this embodiment, the color coding guide is shown above the fluoroscopy image.

As is known to one skilled in art, far-field signals from the left atrium (LA) are frequently recorded from electrodes placed in the pulmonary vein. To separate the far-field signals from the pulmonary vein recordings, physicians may perform pacing from the coronary sinus (CS) level. Alternatively, the signals may be displayed in the frequency domain. As the frequency content of the pulmonary vein potentials is different than the frequency content of left atrial signals.

Figure 39:
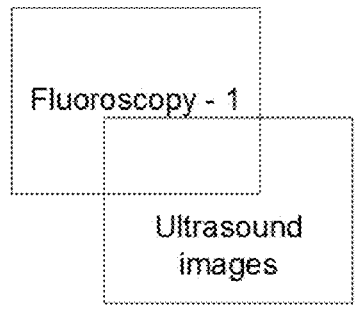
FIG. 39 is a block diagram showing combining ultrasound imaging with fluoroscopy for the purposes of the current mapping system.

In one embodiment, the ultrasound images are combined and superimposed on fluoroscopy. This is depicted in FIG. 39. Generally, ultrasound images have many advantages, and are routinely utilized during atrial fibrillation procedures performed in the United States. The ultrasound technology utilized is generally in the form of Intracardiac echocardiography (ICE). The advantages of ICE includes features where the images actually show the anatomic structures and unlike fluoroscopy or x-ray, ultrasound does not emit ionizing radiation.

Figure 41:
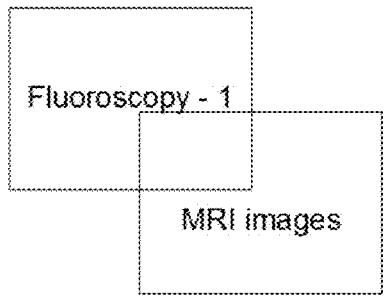
FIG. 41 is a block diagram depicting combining MRI images with fluoroscopy imaging.

In one embodiment, depicted in FIG. 41 fluoroscopy and MRI images are combined together. MRI images may be either registered or overlaid on fluoroscopy images. The MRI images also provide detailed 3D imaging, much like the CT images. As was mentioned previously, if the MRI images are registered then several tags will be placed on both the structures that are being registered. Alternatively, the MRI images may be placed or overlaid on fluoroscopy as a guide to place the Cryoballoon catheter in the proper vein.

Figure 42:
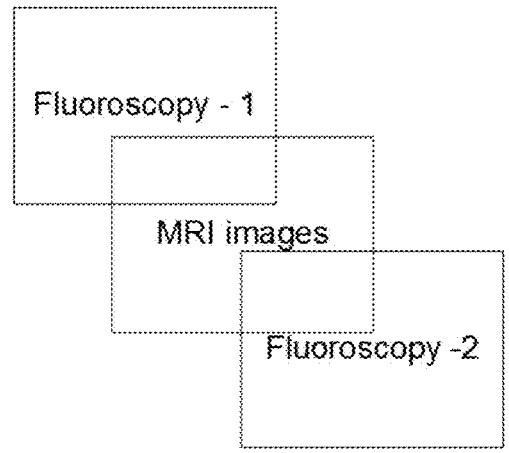

In one embodiment, two layers of fluoroscopy and MRI images may also be displayed on the monitor to guide the physician, this is shown with FIG. 42. In one aspect, high resolution fluoroscopy with contrast medium (dye) injection is recorded and used as an outline for the chamber geometry and for pulmonary vein(s). Based on the outline of the recorded images, the MRI images are positioned to the appropriate location. As with the case of CT, the MRI images may be registered with fluoroscopy based on placing common landmark tags on the recorded high resolution fluoroscopic images and the MRI. Alternatively, the MRI images may be placed by an operator (or overlaid) on the outline of the heart and/or pulmonary veins utilizing tools such as pan, zoom and rotate. Following that, a live fluoroscopy image layer is placed on the first two layers. The physician then positions the Cryoballoon catheter based on the real-time fluoroscopy layer, taking advantage of the recorded fluoroscopy and the high resolution anatomy of the 3D MRI images which are in the background.

Figure 40:
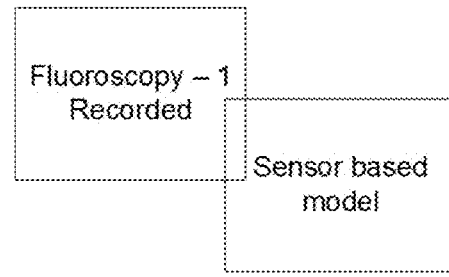
FIG. 40 is a block diagram depicting a sensor based model imaging combined with fluoroscopy imaging for the purposes of the current mapping system.

In one aspect shown with FIG. 40, a sensor based model of the heart geometry is created and registered or overlaid on fluoroscopy. The rationale for doing this is that since the Cryoballoon catheter does not communicate with sensor based mapping systems, fluoroscopy will be utilized for the placement of the Cryoballoon catheter. It will be clear to one skilled in the art that many different types of sensor based catheters are available for creating geometry. The most popular ones are electrical impedance based sensors, magnetic sensors or combination of electrical impedance and magnetic based sensors. The left atrial chamber geometry may also be made utilizing an ultrasound based catheter.

In one aspect, while recording a contrast medium ("dye") injection, a rotation of fluoroscope C-arm may be recorded. If a complete rotation is recorded, the software is programmed and configured such that any angle of fluoroscopy is available and may be used.

Figures 43, 44:
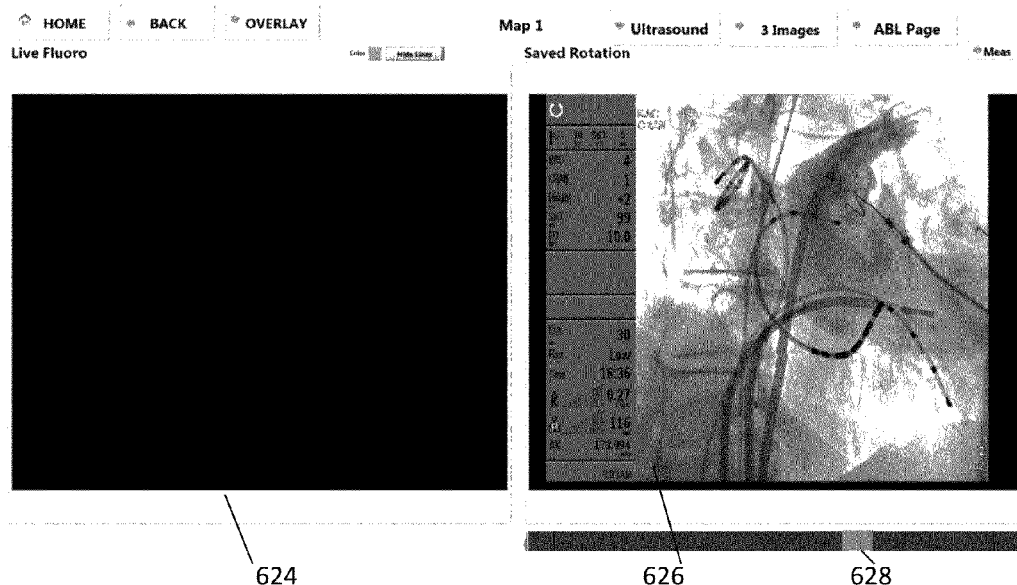
FIG. 43 is a diagram showing one implementation where live fluoroscopy and recorded fluoroscopy are displayed side-by-side.
FIG. 44 is a diagram showing one implementation where live fluoroscopy and recorded fluoroscopy are displayed side-by-side and outline of the chamber and pulmonary veins are outlined on live fluoroscopy.

One example of implementation is shown with FIG. 43. As shown in FIG. 43, a live fluoroscopy and a saved fluoroscopy rotation is displayed side-by-side. The saved rotation 626 is on the right side of the figure and the live fluoroscopy 624 is on the left side. Since the whole rotation is saved with contrast medium (dye) injection, as the live fluoroscopy angle is changed by the physician, the recorded "dye" injection fluoroscope image can be changed to the same angle as the live (or real-time) fluoroscope angle. In this implementation, a slider bar 628 is used to adjust the angle of the fluoroscope to match the angle of the live fluoroscope (shown on the left side of the figure).

In one aspect, as is shown with FIG. 44, the recorded contrast medium ("dye") injection image may be used to mark the outline of the atrium and pulmonary veins on the live fluoroscopy. This is then used by the physician to guide a catheter, such as a cryoballoon catheter or any other catheter into the pulmonary veins or the os of the pulmonary veins.

Of course, the physician has control over the amount of contrast medium ("dye") to inject and where to inject the contrast medium ("dye"). Generally, one of two methods are used. In one method, the contrast medium ("dye") is injected with a power injector in the right side of the heart. In this case the contrast medium ("dye") will go through the lungs and return to the pulmonary veins and the left atrium. At the point the "dye" starts to show up in the pulmonary veins (in approximately 5-8 seconds), a recording is generally made. An example of the image obtained with this method is shown in FIG. 27. The second method is to inject the "dye" straight into the left atrium and/or pulmonary veins, with or without a power injector.

In our implementation, FIG. 45 shows an example of "dye" injected into the left atrial chamber 632 via a lumen catheter 630. This is also substantiated with the "dye" being above the coronary sinus (CS) catheter 629 shown in the picture. Anatomically, the coronary sinus (CS) runs between the left atrium and left ventricle.

Also, for our implementation FIG. 46 shows an example of "dye" injection, this time in the left superior vein 636 via a lumen catheter 634 close to the os of the pulmonary veins.

FIG. 47 shows our testing of the concept shown in FIG. 35, where two fluoroscopy images are overlaid on top of each other. Once the two layers of fluoroscopy, high resolution images with contrast medium ("dye") and live fluoroscopy are overlaid on top of each other, one of the images may be manually moved to align the structures such that they are overlaid on top of each other and aligned and adjusted appropriately. The software is configured and programmed such that the transparency between the recorded and stored image(s) and live images can be adjusted by the operator. This is implemented with the aid of transparency bar 644, as shown in the figure. At one extreme of the transparency bar, only the recorded image(s) are visible. At the other extreme, only the live fluoroscope is visible. The transparency is adjusted by the operator such that the physician can manipulate the catheter on the live image, but at the same time have the benefit of the clear anatomic details from high resolution images with contrast medium ("dye") injection.

Further, as the catheter is placed in the appropriate pulmonary vein, the electrical signals are also recorded. The software and hardware is configured such that each pair of electrode picks up the peak-to-peak voltage signals, color codes the signals according to the size of the voltage levels and display's them in the form of a real-time bar graph 641 or ring graph 643. The ring graph 643 is configured and programmed such that the ring 643 is a 3D structure which can be rotated or moved in any angle.

In one aspect, a volume rendered 3D image if available can also be utilized in the placement of the catheter for atrial fibrillation ablation. A patient's CT scan is processed and a 3D volume rendering of the region of interest is obtained using software and techniques well known in the art. An example of this is shown in FIG. 48. The 3D volume rendering of the image 646 is done either using the mapping system computer, or is done on a separate computer and brought into the mapping system computer. The CT image 646 (in FIG. 48) can be panned, zoomed, moved or rotated such that it can be properly aligned with other images such as the fluoroscope image for example.

In one aspect, as was mentioned earlier and shown with FIG. 38, the CT image may be used with recorded fluoroscopy image (high resolution with contrast medium or "dye" injection) and live fluoroscopy for aiding the placement of the catheter such as balloon catheter or any other catheter which needs to be placed around the pulmonary veins.

In our implementation, shown in FIG. 49, in the first part the CT image 646 is aligned with recorded fluoroscopy image which may be in high resolution along with contrast medium injection or "dye" injection. The purpose of this is to show the details of the appropriate anatomy and to match the structures of the CT image with the fluoroscopy image.

In one aspect, the CT image may be registered with the fluoroscopy image. For the registration process several points (at least three) need to be defined that are common to both structures.

In one aspect, instead of registering the CT image with fluoroscopy, the CT image is overlaid on the fluoroscopy. The size, orientation and position of the CT image to match fluoroscopy structures are manually performed by the operator. This involves approximation and operator judgment, but for the current application, it works well.

Shown in FIG. 49, is one implementation which we have tested and found to work well. The operator adjusts and overlays the CT image on the fluoroscope after it has been properly resized and properly oriented. Further, the transparency is adjusted such that when live fluoroscopy is overlaid on top of the CT image, it will be useful.

FIG. 50 shows, the final layer of live fluoroscopy which is placed at the top layer for visualization and placement of a cryoballoon catheter or any other catheter. Once the catheter is placed in the proper position, the signals may also be recorded as is shown in bargraph 658 or in the form of a 3D ring 660 as is shown in the figure.

As the Cryoballoon catheter is placed in the appropriate pulmonary vein, an electrode catheter with multiple electrodes is generally advanced and placed in the pulmonary vein more distal to the balloon.

Referring again to FIG. 50, as the Cryoballoon catheter is placed in each of the pulmonary veins and the multiple electrode catheter is placed in the pulmonary veins, the signals recorded from the electrodes are displayed on the monitor along with the fluoroscope image. In the method and system of this disclosure, the underlying signals from each electrode are recorded and displayed on the monitor screen. This is shown in the form of a bar graph 658, which are the peak-to-peak voltage signals. In one aspect the software is configured and programmed such that the bars are color coded based on the underlying peak-to-peak voltage. Additionally, in one implementation the underlying signal measurements are converted to color based on a color coding scheme and are displayed in the form of a ring 660 which adds a three dimensional element, as the ring can be manipulated in 3D.

In the method and system of this disclosure, after the balloon is inflated and the catheter is appropriately placed in the pulmonary vein, ablation is performed by freezing the tissue. The length or duration of freezing is determined by the physician. In one aspect of the disclosure, the ablation (freezing) areas' are marked or "tagged" for aiding the procedure and also stored for documentation purposes. In the method and system of this disclosure, various ways are disclosed for this and are shown with FIGS. 51-53.

The software is configured and programmed in a way such that every time there is an ablation, the area representative of the ablation contact area of freezing is marked ("tagged"). Generally, in RF ablation the ablation area is relatively small because the ablation is point by point ablation. With Cryoballoon ablation, the whole pulmonary vein is typically freeze ablated in a single shot. Therefore, the ablation tagging ideally needs to be such that it captures that.

Figure 51:
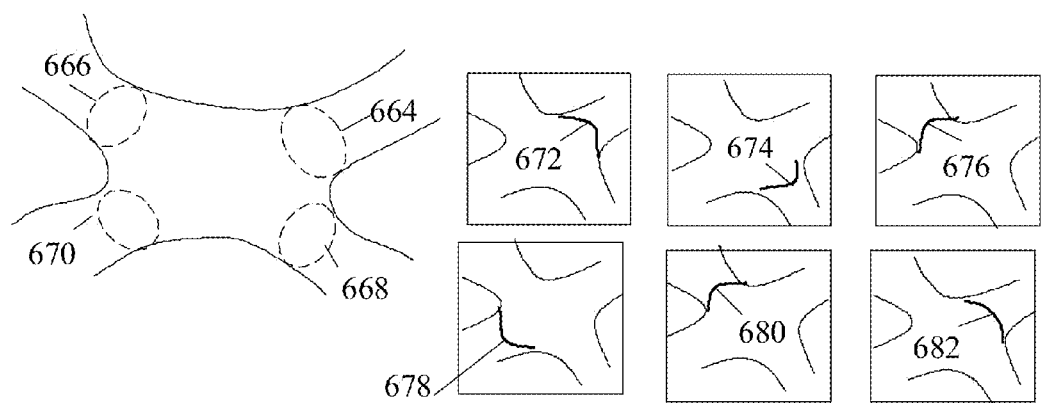
FIG. 51 is a diagrammatical representation showing marked sites of individual cryoballoon catheter freezes or cryo-ablations.

In one aspect, shown in conjunction with FIG. 51 the software is configured and programmed such that the ablation contact area is marked with the aid of a computer mouse by drawing a series of lines or circles or other markings. In one embodiment, each freeze is saved as separate picture or frame. Therefore, if there are six freezes (ablations) for example, then six pictures are saved. In the review screen, all of the screens are shown next to each other, for the physician to visualize where ablations have occurred.

As shown in FIG. 51, in the planning of the Cryoballoon ablation procedure at the level of left superior pulmonary vein os 664, left inferior pulmonary vein os 668, right superior pulmonary vein os 666, right inferior pulmonary vein os 670 are shown in the top portion of the figure. The bottom portion of the figure shows ablation markings or ablation "tags" 672, 674, 676, 678, 680, and 682 at various ablation sites. When the operator retrieves the review tag screen, the physician is able to visualize where the ablations have been performed.

Figure 52:
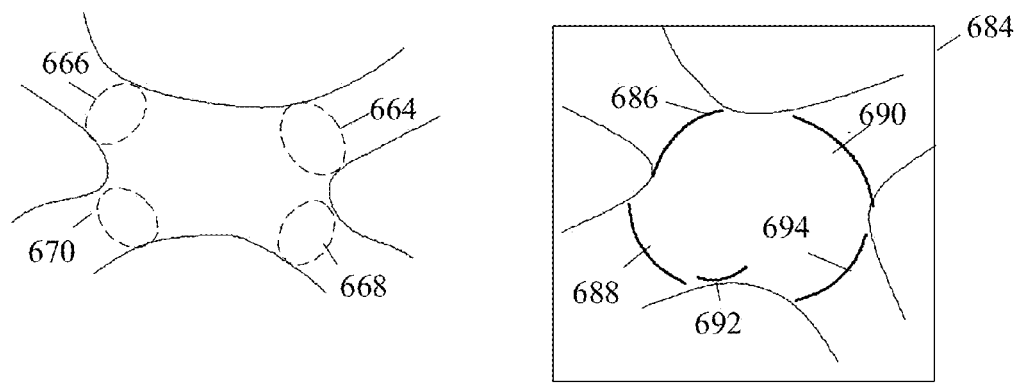
FIG. 52 is a diagram showing various cryo-ablations in one picture.

In another aspect, the various images comprising the ablation tags are merged together utilizing software coding and manipulation and are displayed in one figure. This is depicted in FIG. 52, where ablation tags 686, 688, 690, 694 and 692 are merged into one figure. As is well known to one skilled in the art, various software packages are available for this purpose. One such software for example is Photoshop, available from Adobe. MATLAB is another package which has built-in function libraries specifically for this. Many other software packages are also available and may be used. This may also utilize the process of registration in 2D.

Figure 53:
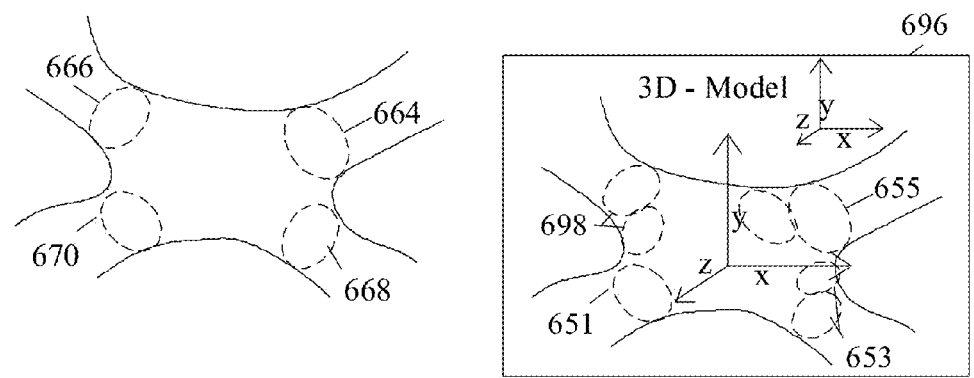
FIG. 53 is a diagram depicting various cryo-ablation lesions on a three dimensional (3-D) image, such as a CT image which can be rotated in 3-D (3 dimensions).
Figure 54:
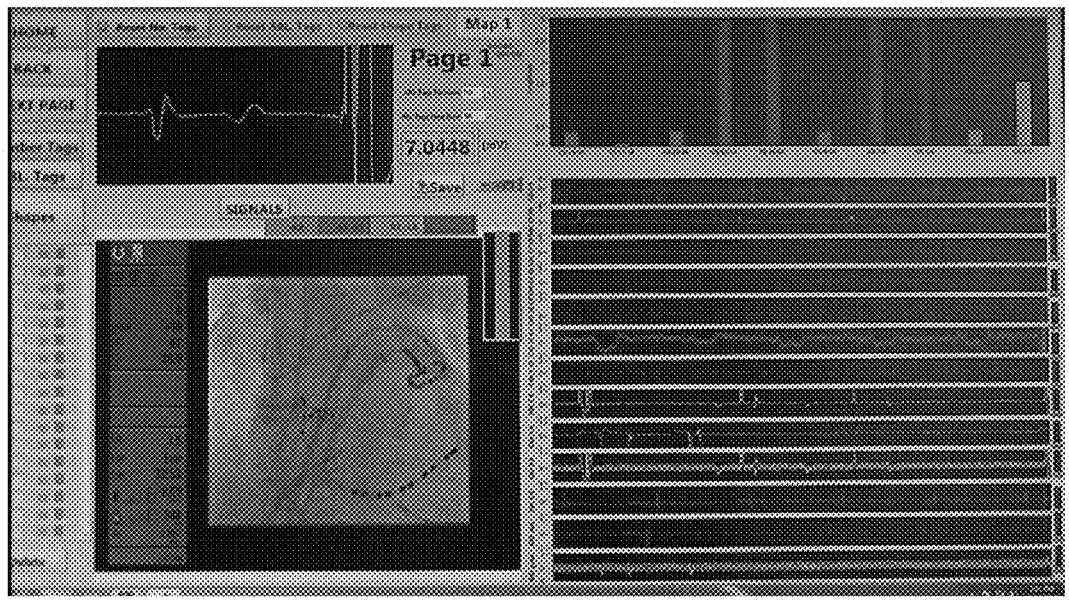
FIG. 54 is diagram showing one page from the implementation where fluoroscopy and electrical signals are displayed on the screen.
Figure 55:
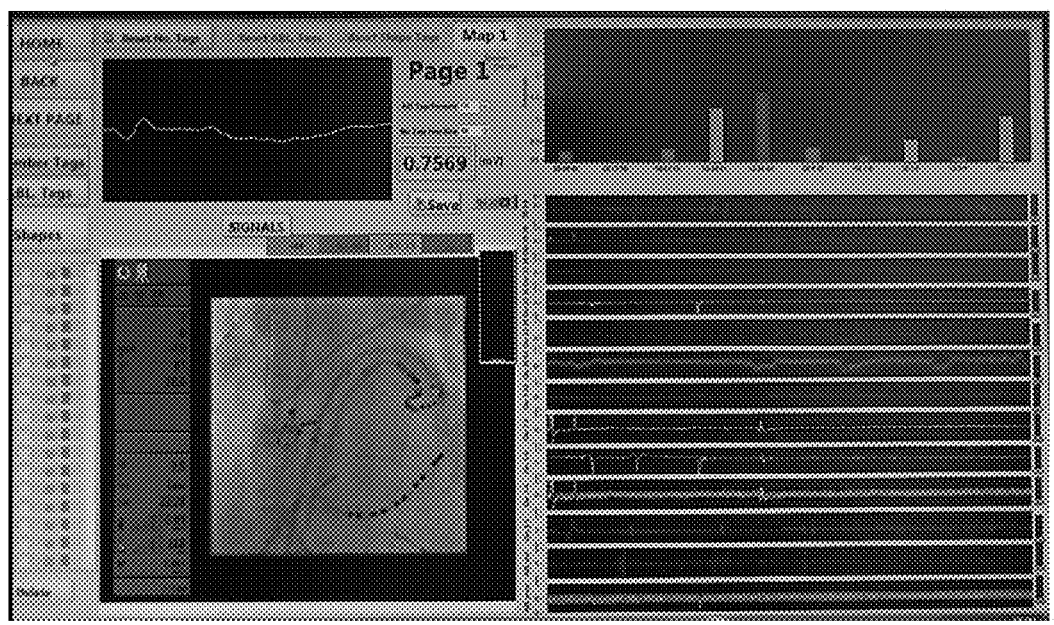
FIG. 55 is another diagram showing one page from the implementation where fluoroscopy and electrical signals are displayed on the screen.
Figure 56:
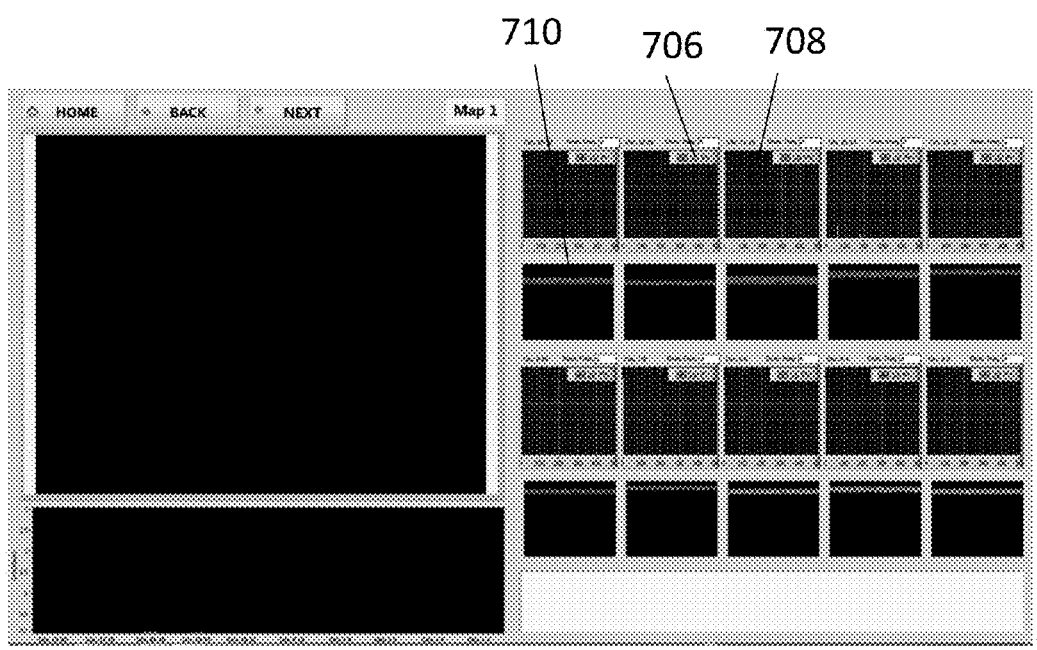
FIG. 56 is diagram showing one page from the implementation where fluoroscopy and electrical signals, both in time domain and frequency domain are displayed on the screen.

In another aspect, various ablation tags are placed on a 3D model, such as a 3D CT model or a 3D MRI model which is registered or overlaid on the fluoroscopy image, as described earlier in this disclosure. This embodiment is depicted in FIG. 53, where tags 651, 653, 655,696 and 698 are marked on a 3D model which can be rotated in 3D.

It will be clear to one skilled in the art that the 3D model may be one that is created using a sensor such as impedance, magnetic or any other type of sensor.

In one aspect, the ablation markings or "tags" may also be correlated with the length of the ablation freeze. For example, the ablation "tags" or markings may be color coded depending on the length of the freeze. In another example the "tag" markings may be larger or be more dense depending on the length of the freezing time.

While this disclosure has been described with reference to preferred embodiments, it will be understood by those skilled in the art that various changes may be made without departing from the scope of the invention. In addition, many modifications may be made to adapt a particular situation or material to the teaching of the invention with departing from the essential scope thereof. Therefore, it is intended that the disclosure not be limited to the particular embodiments disclosed for carrying out this invention, but that the invention will include all embodiments falling within the scope of the appended claims.

The invention claimed is:

1. A method of cardiac mapping for balloon based catheter ablations comprises the steps of:
    gathering and displaying fluoroscopy and/or medical image(s) wherein, said fluoroscopy and/or medical image(s) capable of being displayed in various combinations;
    monitoring an esophageal temperature wherein, said monitoring an esophageal temperature can trigger alarms or ablation energy cutoff, based on pre-determined values of the esophageal temperature;
    acquiring a patient's cardiac signals utilizing an interface electronics;
    overlaying two or more of said fluoroscopy and/or medical image(s) and adjusting transparency between said image(s); and
    placing a balloon based catheter at an appropriate location for ablation/freezing in left atrium and/or around pulmonary veins utilizing said overlaying two or more of said fluoroscopy and/or medical image(s) and adjusting said transparency between said image(s).

2. The method of claim 1 wherein, said fluoroscopy and/or medical images may be one or more from the group comprising, stored fluoroscopy image, or stored fluoroscopy video, or recorded high resolution fluoroscopy with contrast medium injection, or CT (computed tomography) images, or MRI (magnetic resonance imaging) images, or ultrasound images, or 3D (three dimensional) fluoroscopy models, or ultrasound catheter based image model.

3. A mapping system for balloon based catheters comprises:
    a computer based cardiac mapping system comprising software and hardware, and capable of utilizing fluoroscopy and/or medical image(s) wherein, said mapping system further capable of monitoring esophageal temperature;
    an interface electronics connected to said computer based cardiac mapping system, for acquiring a patient's electrical signals and said fluoroscopy and/or medical image(s);
    said mapping system further comprises capability for monitoring of esophageal temperature and triggering of alarms or ablation energy cutoff based on pre-determined values of the esophageal temperature, and said software in said computer based cardiac mapping system configured and programmed for overlaying two or more of said fluoroscopy and/or medical image(s) on top of each other, wherein a transparency factor between said two or more images of said fluoroscopy and/or medical images(s) can be adjusted for aiding in placing a balloon based catheter(s) in an appropriate location in left atrium and/or around pulmonary vein(s).

4. The system of claim 3 wherein, said fluoroscopy and/or medical image(s) may be one or more from the group comprising, stored fluoroscopy image, or stored fluoroscopy video, or recorded high resolution fluoroscopy with contrast medium injection, or CT images, or MRI images, or ultrasound images, or 3D fluoroscopy models.

5. The system of claim 3 wherein, said overlaying of two or more image(s) includes a recorded fluoroscopy image(s) with contrast medium injection and a CT image model.

6. The system of claim 3 wherein, said overlaying of two or more image(s) includes a recorded fluoroscopy image(s) with contrast medium injection, a CT image model, and live fluoroscopy image(s).

7. The system of claim 3 wherein, said computer based cardiac mapping system is used for atrial fibrillation ablation.

8. The system of claim 3 wherein, the software coding may utilize a software which is one from a group comprising LAB WINDOWS/CVI, LABVIEW® (National Instruments Corp.), C, C+, Microsoft Visual C++, Dot Net framework, MATLAB®, and Microsoft Visual Basic, or any functional equivalent software language.

9. A method of cardiac mapping for balloon based catheter ablations comprises the steps of:
   gathering and displaying a fluoroscopy and/or medical image(s);
   acquiring and displaying a patient's cardiac signals through an interface electronics;
   placing a computed tomography (CT) image next to two layers of fluoroscopy images on top of each other; and
   placing a balloon based catheter at an appropriate location for ablation/freezing in left atrium and/or around pulmonary veins utilizing said two layers of fluoroscopy images on top of each other and adjusting a transparency between said two layers of fluoroscopy images.

10. The method of claim 9 wherein, said adjusting a transparency between said two layers of fluoroscopy images is such that at one extreme only the bottom image(s) is visible or at the other extreme only the top image(s) is visible, or all different levels in-between the two extremes where both the top and bottom image(s) are visible.

11. The method of claim 9 wherein, said balloon based catheter comprises a cryoballoon catheter, or laser balloon, or other balloon catheter used in cardiac ablation for atrial fibrillation ablation.

12. The method of claim 9 wherein, said fluoroscopy and/or medical images may be one or more from the group comprising, stored fluoroscopy image, or stored fluoroscopy video, or recorded high resolution fluoroscopy with contrast medium injection, or CT (computed tomography) images, or MRI (magnetic resonance imaging) images, or ultrasound images, or 3D (three dimensional) fluoroscopy models, or ultrasound catheter based image model.

13. The method of claim 9 wherein, said two layers of fluoroscopy images on top of each other includes a recorded fluoroscopy images with contrast medium injection and a computed tomography (CT) image model with electrical signals displayed next to images.

14. The method of claim 9 wherein, the coding may utilize software which is one from a group comprising LAB WINDOWS/CVI, LABVIEW (National Instruments Corp.), C, C+, Microsoft Visual C++, Dot Net framework, MATLAB, and Microsoft Visual Basic, or any functional equivalent software language.

* * * * *